US012778925B2

(12) United States Patent
Beyrath et al.

(10) Patent No.: US 12,778,925 B2
(45) Date of Patent: Nov. 3, 2026

(54) TREATMENT OF MITOCHONDRIAL DISEASES

(71) Applicant: Khondrion IP B.V., Beuningen (NL)

(72) Inventors: Julien David Beyrath, Nijmegen (NL); Johannes Albertus Maria Smeitink, Beuningen (NL)

(73) Assignee: Khondrion IP B.V., Beuningen (NL)

( * ) Notice: Subject to any disclaimer, the term of this patent is extended or adjusted under 35 U.S.C. 154(b) by 322 days.

(21) Appl. No.: 18/679,619

(22) Filed: May 31, 2024

(65) Prior Publication Data

US 2024/0390321 A1 Nov. 28, 2024

Related U.S. Application Data

(62) Division of application No. 17/672,731, filed on Feb. 16, 2022, now Pat. No. 12,226,394, which is a division of application No. 16/500,437, filed as application No. PCT/EP2017/072172 on Sep. 5, 2017, now Pat. No. 11,285,130.

(30) Foreign Application Priority Data

Apr. 5, 2017 (EP) .................................... 17165012

(51) Int. Cl.
*A61K 31/355* (2006.01)
*A61K 9/00* (2006.01)
*A61K 45/06* (2006.01)

(52) U.S. Cl.
CPC .......... *A61K 31/355* (2013.01); *A61K 9/0053* (2013.01); *A61K 9/0095* (2013.01); *A61K 45/06* (2013.01)

(58) Field of Classification Search
CPC .................................................... A61K 31/355
See application file for complete search history.

(56) References Cited

U.S. PATENT DOCUMENTS 12,226,394 B2 * 2/2025 Beyrath ............... A61K 31/355
2009/0118257 A1 5/2009 Jankowski

FOREIGN PATENT DOCUMENTS

| | | | |
|---|---|---|---|
| WO | WO2012/019029 | A2 | 2/2012 |
| WO | WO2012/019032 | A1 | 2/2012 |
| WO | WO2014/011047 | A1 | 1/2014 |
| WO | WO2014/098586 | A1 | 6/2014 |
| WO | WO2017/060432 | A1 | 4/2017 |

OTHER PUBLICATIONS

Laursen, Morten, et al. "Characterization of cardiac repolarization in the Göttingen minipig." Journal of Pharmacological and Toxicological Methods 63.2 (2011): 186-195.

Swart, Daniël H., et al. "Safety, tolerability and toxicokinetics of the novel mitochondrial drug SUL-138 administered orally to rat and minipig." Toxicology Reports 12 (2024): 345-355.

Ich Harmonised Tripartite Guideline E14. The Clinical Evaluation of QT/QTc Interval Prolongation and Proarrhythmic Potential for Non-Antiarrhythmic Drugs (CHMP/ICH/2/04), dated Nov. 2005.

Anonymous: The Khenergy Study—Full Text View—ClinicalTrials. gov, (Sep. 21, 2016), Retrieved from the Internet: URL:https://clinicaltrials.gov/ct2/show/NC.

Anonymous: Khenergy: completion of recruitment and first-in-patient dosing, (Oct. 24, 2016), Retrieved from the Internet:URL:http://WWW.khondrion.com/News-detai l/4053/38990/KHENERGY-completion-of-recruitment-and-first-in-patient-dosing.html?publicationdate=True [retrieved on Nov. 2, 2017].

W. J. Koopman et al: Mitochondrial disorders in children: toward development of small-molecule treatment strategies, EMBO Molecular Medicine, vol. 8, No. 4, (Apr. 1, 2016), pp. 311-327.

Ji, Junfeng, et al. Antioxidant Supplementation Reduces Genomic Aberrations in Human Induced Pluripotent Stem Cells; Stem Cell Reports vol. 2 44-51 Jan. 14, 2014.

Koopman, Werner JH, Peter HGM Willems, and Jan AM Smeitink. "Monogenic mitochondrial disorders." New England Journal of Medicine 366.12 (2012): 1132-1141.

Koene, S., et al. "Natural disease course and genotype-phenotype correlations in Complex I deficiency caused by nuclear gene defects: what we learned from 130 cases." Journal of inherited metabolic disease 35.5 (2012): 737-747.

Gorman, Gráinne S., et al. "Prevalence of nuclear and mitochondrial DNA mutations related to adult mitochondrial disease." Annals of neurology 77.5 (2015): 753-759.

Bénit, Paule, et al. "Genetic background influences mitochondrial function: modeling mitochondrial disease for therapeutic development." Trends in molecular medicine 16.5 (2010): 210-217.

Klopstock, Thomas, et al. "A randomized placebo-controlled trial of idebenone in Leber's hereditary optic neuropathy." Brain 134.9 (2011): 2677-2686.

Angelin, Alessia, et al. "Mitochondrial dysfunction in the pathogenesis of Ullrich congenital muscular dystrophy and prospective therapy with cyclosporins." Proceedings of the National Academy of Sciences 104.3 (2007): 991-996.

Merlini, Luciano, et al. "Cyclosporin A corrects mitochondrial dysfunction and muscle apoptosis in patients with collagen VI myopathies." Proceedings of the National Academy of Sciences 105.13 (2008): 5225-5229.

Pfeffer, Gerald, et al. "New treatments for mitochondrial disease-—no time to drop our standards." Nature Reviews Neurology 9.8 (2013): 474.

Distelmaier, Felix, et al. "Trolox-sensitive reactive oxygen species regulate mitochondrial morphology, oxidative phosphorylation and cytosolic calcium handling in healthy cells." Antioxidants & redox signaling 17.12 (2012): 1657-1669.

(Continued)

*Primary Examiner* — Rei Tsang Shiao
(74) *Attorney, Agent, or Firm* — Ipsilon USA—NLO

(57) ABSTRACT

The current invention concerns an innovative treatment for mitochondrial disorders and diseases or conditions associated with mitochondrial dysfunction. In particular, effective and safe dosages of compounds suitable for the treatment of mitochondrial disorders have been established, providing for new treatment regimens and patient populations.

18 Claims, 18 Drawing Sheets

(56) References Cited

OTHER PUBLICATIONS

Ich Harmonised Tripartite Guideline: Safety pharmacology studies for human pharmaceuticals, S7A, dated Nov. 8, 2000; International conference on harmonisation of technical requirements for registration of pharmaceuticals for human use.

Ich Harmonised Tripartite Guideline: The non-clinical evaluation of the potential for delayed ventricular repolarization (QT interval prolongation) by human pharmaceuticals, S7B, dated May 12, 2005; International conference on harmonisation of technical requirements for registration of pharmaceuticals for human use.

Rohatagi et al. (2009). Is a Thorough QTc Study Necessary? The Role of Modelling and Simulation in Evaluating the QTc Prolongation Potential of Drugs. The Journal of Clinical Pharmacology, 49(11), 1284-1296.

Malik et al. (2008). Near-Thorough QT Study as Part of a First-In-Man Study. The Journal of Clinical Pharmacology, 48(10), 1146-1157.

Anonymous: "A Dose-escalating Clinical Trial With KH176—History of Changes (Side-by-Side) for Study: NCT02544217—Sep. 4, 2015 (v1)—Feb. 5, 2016 (v2)—ClinicalTrials.gov", Sep. 9, 2015 (Sep. 9, 2015).

FDA Concept Paper Drug Interaction Studies—Study design, Data Analysis, and Implications for Dosing and Labelling, Oct. 1, 2004.

Guideline on the investigation of drug interactions, Jun. 21, 2012, CPMP/EWP/560/95/Rev, Committee for Human Medicinal Products (CHMP), European Medicines Agency (EMA).

Vogelaar et al. (2022). Towards prevention of ischemia-reperfusion kidney injury: Pre-clinical evaluation of 6-chromanol derivatives and lead compound SUL-138. Eur. J. of Pharmaceutical Sc. 168: 106033. (D19A original article; D19B supplemental material).

Hajmousa et al. (2016). The 6-chromanol derivative SUL-109 enables prolonged hypothermic storage of adipose tissue-derived stem cells, Biomaterials (2017) 119:43-52.

Garrido et al. (2020). hERG toxicity assessment: Useful guidelines for drug design, Eur. J. Med. Chem. 1:195:112290.

* cited by examiner

TREATMENT OF MITOCHONDRIAL DISEASES

FIELD OF THE INVENTION

The invention relates to the field of human, plant and animal diseases. The invention in particular relates to amide-derivatives of vitamin E for treating conditions that are associated with oxidative stress, mitochondrial dysfunction or mitochondrial deficiencies, including the establishment of the effective and safe doses in humans.

BACKGROUND ART

Reactive oxygen species (ROS) are involved in a broad spectrum of cellular processes, such as cell signalling, apoptosis and homeostasis. This implicates a crucial role for ROS in normal cellular function. However, (too) high levels of ROS may cause significant damage to cell structures, which is known as oxidative stress. Oxidative stress is thought to be involved in the development of many different diseases, such as Asperger syndrome, ADHD, cancer, Parkinson's disease, Lafora disease, Alzheimer's disease, atherosclerosis, heart failure, myocardial infarction, fragile X syndrome, Sickle Cell Disease, lichen planus, vitiligo, autism, infection, congenital muscular dystrophies, dystrophinopathies and chronic fatigue syndrome. Furthermore, it has recently been shown that supporting the cellular redox homeostasis is also important in many ex vivo techniques, such as during the induction of pluripotent stem cells (Ji et al, Stem cell reports (2014) vol. 2:44-51).

A major source of reactive oxygen species is mitochondria. Mitochondria are essential organelles that constitute the 'powerhouses' of the cell. Defects in these organelles often lead to a variety of severe metabolic disorders affecting the organs that have a high-energy demand, such as muscle and brain. With an incidence of at least 1 in 5000 individuals it is recognized as the most common group of inborn errors of metabolism. Moreover, because programmed cell death (apoptosis) is triggered by mitochondria, defects in these organelles have consequences far beyond the diseases, which brought them initially to our attention and involvement in cancer and neurodegenerative diseases like Alzheimer and Parkinson has been demonstrated. Many commonly used drugs like the NRTIs, certain antibiotics, statins and anti-epileptic drugs, may cause mitochondrial dysfunction. So far no effective treatment is available to cure or improve these disease conditions.

One of the primary functions of mitochondria is oxidative phosphorylation (OXPHOS). The molecule adenosine triphosphate (ATP) functions as an energy "currency" or energy carrier in the cell, and eukaryotic cells derive the majority of their ATP from biochemical processes carried out by mitochondria Mitochondrial oxidative phosphorylation is a major cellular source of reactive oxygen species (ROS), as approximately 1-2% of oxygen consumed during physiological respiration is converted into superoxide ($O_2^-$) when electrons prematurely leak from the electron transport chain and are aberrantly transferred to molecular oxygen. However, under specific metabolic or stress conditions, more electrons can prematurely exit the respiratory chain to further augment mitochondrial superoxide generation.

Over 1,150 genes have been identified to encode for proteins located in the mitochondria. Mutations in these genes, like those involved in oxidative phosphorylation, can cause mitochondrial disease. This genetic heterogeneity is one of the numerous factors explaining the phenotypic variability seen in mitochondrial diseases, including many mono-, and multisystem phenotypes in childhood and adulthood (Koopman W J et al, *Engl J Med* 2012, 366:1132-1141). Although the rate of deterioration is variable, the disease course is often progressive and the prognosis of some of the childhood diseases is even very poor (Koene S et al, *J Inherit Metab Dis* 2012, 35:737-747). With a minimal prevalence rate of about 1 in 4,300-5,000 (Gorman et al, *Ann Neurol* 2015, 77:753-759), there is a clear need for therapy for these devastating disorders.

The contribution of mitochondrial dysfunction to human disease was already recognised in the late 1980s, when maternally inherited point mutations, as well as deletions arising spontaneously during development, were found to be associated with rare neurological syndromes. Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), dominant optic atrophy (DOA); mitochondrial myopathy, encephalopathy, lactic acidosis, and stroke-like episodes (MELAS), Myoclonus Epilepsy Associated with Ragged-Red Fibers (MERRF) syndrome, Leigh syndrome, and oxidative phosphorylation disorders. Mitochondrial diseases involve children and adults who manifest the signs and symptoms of accelerated aging, including neurodegenerative diseases, stroke, blindness, hearing impairment, diabetes, and heart, liver and kidney failure and myopathies.

Very few treatments are available for patients suffering from these mitochondrial diseases. The drug idebenone (a CoQ10 variant) has been approved for the treatment of Friedreich's ataxia (Bénit et al., 2010, Trends Mol Med, 16:210-7; Klopstock et al., 2011, Brain, 134:2677-86) and LHON. A successful treatment strategy has been developed for patients with a secondary mitochondrial disorder involving Ullrich's congenital muscular dystrophy and Bethlem's myopathy. The pathogenic mechanism in these myopathies involves inappropriate opening of the mitochondrial permeability transition pore. This action was prevented in patients treated with the permeability-transition-pore desensitizer CSA (cyclosporin A; Angelin et al., 2007, Proc Natl Acad Sci USA, 104:991-6; Merlini et al., 2008, Proc Natl Acad Sci USA, 105:5225-9).

However, Pfeffer et al (Pfeffer et al, Nat Rev Neurol (2013), 9 (8): 474-481)_concluded that despite an increase over the past two decades in the number of published studies reporting treatment effects in mitochondrial disease, a systematic review of the literature found no evidence of an effective intervention for any mitochondrial disorder. Pfeffer et al, supra, further shows that the outcome of clinical studies are highly unpredictable (see Table 1 of Pfeffer et al) and that none of the clinically relevant primary endpoints were statistically significant in high-quality studies. Hence, a novel well-tolerated treatment for mitochondrial disorders is warranted.

WO 2012/019032 discloses methods of treatment, prevention, or suppression of symptoms associated with a mitochondrial disorder and/or modulating, normalizing, or enhancing one or more energy biomarkers, whereby vitamin K analogues are administered.

WO 2012/019029 discloses methods of treatment, prevention, or suppression of symptoms associated with a mitochondrial disorder and/or modulating, normalizing, or enhancing one or more energy biomarkers, whereby naphtoquinones and derivatives thereof are administered.

Distelmaier et al. (2012, Antioxid Redox Signal. 17 (12):1657-69) disclose that Trolox™ (6-hydroxy-2,5,7,8-tetramethylchroman-2-carboxylic acid) reduces the levels of ROS, increased mitofusins-mediated mitochondrial filamentation and expression of mitochondrial complex I, activity of citrate synthase and OXPHOS enzymes and cellular O2 consumption in cultured healthy human skin fibroblasts.

WO 2014/011047 discloses novel compounds which can be useful for the treatment or prevention of mitochondrial disorders, conditions associated with mitochondrial dysfunction and/or neoplastic diseases, using Trolox-derivatives. In particular, these derivatives are useful in modulating mitochondrial morphology and/or expression of OXPHOS enzymes and/or cellular ROS. WO 2014/011047 discloses Trolox derivatives, wherein the carboxylic acid moiety is replaced by an amide moiety and wherein the nitrogen atom of the amide moiety is connected via a linker to a cationic nitrogen atom. There is however still a need in the art for a safe and effective treatment of mitochondrial disorders or diseases and conditions associated with mitochondrial dysfunction. In particular, there is a need in the art for treatment regimens that lead to an effective and safe administration of compounds that have previously shown potential for the treatment of mitochondrial disorders or conditions associated with mitochondrial dysfunction

SUMMARY OF THE INVENTION

In a first aspect, the invention pertains to a compound represented by general structure (I):

(I)

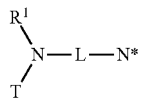

wherein,

- T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;
- N* is represented by structure (IIa) or (IIb)

(IIa)

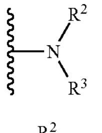

(IIb)

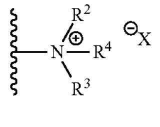

- $R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
- $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; and
- $R^4$ is selected from hydrogen (H) or $C_1$-$C_6$ alkyl, wherein the alkyl moiety may be substituted with one or more halogen atoms or (halo) alkoxy moieties;
- X is an anion, preferably a pharmaceutically acceptable anion, for use in treating, preventing, or suppressing symptoms associated with a mitochondrial disorder or with a disease or condition associated with mitochondrial dysfunction by administration of a total daily dose in the range of about 10 to 1000 mg.

Preferably, the compound is represented by structure (VI):

(VI)

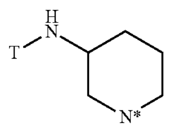

wherein, N* is —$N^+R^3$ or —$N^+R^3R^4X^-$.

Preferably, T is represented by structure (IIIa) or (IIIb):

(IIIa)

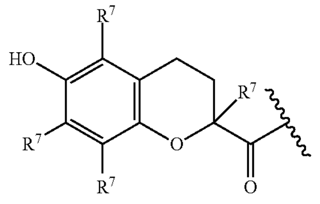

(IIIb)

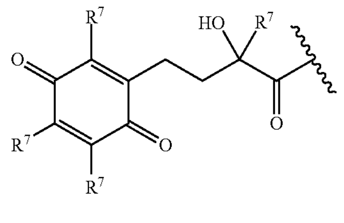

wherein $R^7$ is individually a $C_1$-$C_6$ alkyl moiety, preferably each $R^7$ is methyl.

In a further preferred embodiment, the invention concerns a compound for use as defined herein, wherein the total daily dose that is administered is in the range of about 20 to 800 mg, wherein preferably the total daily dose is in the range of about 30 to 700 mg, and wherein more preferably the total daily dose is in the range of between about 30 to 400 mg and wherein even more preferably the total daily dose is in the range of between about 30 to 300 mg and wherein most preferably the total daily dose is in the range of about 150 to 250 mg. Most preferably, the total daily dose that is administered is about 200 mg.

The invention further preferably relates to a compound for use as defined herein, wherein the mitochondrial disorder is a disorder selected from the group consisting of: Myoclonic epilepsy; Myoclonic Epilepsy with Ragged Red Fibers (MERRF); Leber's Hereditary Optic Neuropathy (LHON); neuropathy ataxia and retinitis pigmentosa (NARP); Mitochondrial Myopathy, Encephalopathy, Lactic acidosis, Stroke-like episodes (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); myopathy; mitochondrial myopathy; cardiomyopathy; and encephalomyopathy, SURF1 (COX deficient Leigh syndrome due to complex IV surfeit protein deficiency) and isolated or combined OXPHOS deficiencies with so far unsolved genetic defect including disturbed pyruvate oxidation and ATP plus PCr production rates. Preferably, the mitochondrial disorder is associated with a m.3242A>G mutation of the mitochondrial tRNA(leu) gene.

In a further preferred embodiment, the invention concerns a compound for use as defined herein, wherein the disease or condition associated with mitochondrial dysfunction preferably is a disease or condition selected from the group consisting of: Friedreich's Ataxia (FRDA); renal tubular acidosis; Parkinson's disease; Alzheimer's disease; amyotrophic lateral sclerosis (ALS); Huntington's disease; developmental pervasive disorders; hearing loss; deafness; diabetes; ageing; and adverse drug effects hampering mitochondrial function.

Preferably, the invention relates to a compound for use as defined herein, wherein a measurable biomarker is used to assess the efficacy of the therapy. More preferably, the biomarker is selected from the group consisting of FGF21, GDF15, PRDX1 and oxidized glutathione/reduced glutathione ratio, wherein preferably the biomarker is measured ex vivo in serum.

The invention further preferably pertains to a compound for use as defined herein, wherein the compound is administered orally.

In a further preferred embodiment, the invention concerns a compound for use as defined herein, wherein the compound is administered in a solid form or in a liquid form. Preferably, the compound is admixed with an aqueous solution prior to administration, wherein preferably the aqueous solution is an isotonic aqueous solution and wherein more preferably the isotonic aqueous solution is saline.

In a preferred embodiment, the invention pertains to a compound for use as defined herein, wherein the compound is administered at least twice daily, preferably wherein the compound is administered twice daily. Preferably, the compound is administered twice daily in two similar or equal doses. Preferably, the interval between two administrations is at least about 1, 2, 3, 4, 5, 6, 7, 8, 9, 10, 11 or 12 hours.

The invention preferably concerns a compound for use as defined herein, wherein the subject to be treated is a primate, wherein preferably the subject is a human.

In a preferred embodiment, the invention pertains to a compound for use as defined herein, wherein the subject to be treated has a clinically relevant normal ECG and/or a normal cardiac functioning. Preferably, the subject to be treated does not have an abnormal QTc of more than 500 ms and/or an abnormal T-wave morphology. Preferably, the subject to be treated does not have a condition selected from the group consisting of cardiovascular disease, alcoholic liver disease, obesity, hypertension and electrolyte disturbances.

In a further preferred embodiment, the invention relates to a compound for use as defined herein, wherein the subject to be treated does not have a concomitant medication that is known to inhibit CYP3A4 and/or PgP.

In a preferred embodiment, the invention concerns a compound for a use as defined herein, wherein the subject to be treated is a human of 17 years or younger.

DESCRIPTION OF THE INVENTION

The current invention pertains to the discovery that compounds useful for treating, preventing, or suppressing symptoms associated with a mitochondrial disorder or with a disease or condition associated with mitochondrial dysfunction cause specific side effects in humans when administered above a certain threshold level. Moreover, the effective dose of such compounds is established and surprisingly, the effective dose is much lower than previously could have been anticipated.

In a first aspect, the invention therefore concerns a method of treating, preventing, or suppressing symptoms associated with a mitochondrial disorder or with a disease or condition associated with mitochondrial dysfunction, the method comprising administering to a subject an effective amount of one or more compounds as defined herein below. The effective amount is preferably an amount as defined herein below.

Alternatively, the invention pertains to a compound as defined herein below for use in treating, preventing, or suppressing symptoms associated with a mitochondrial disorder or with a disease or condition associated with mitochondrial dysfunction by administration of an effective dose as defined herein below.

The medical use herein described is formulated as a compound as defined herein for use as a medicament for treatment of the stated disease(s) by administration of an effective amount of the compound, but could equally be formulated as a method of treatment of the stated disease(s) using a compound as defined herein comprising a step of administering to a subject an effective amount of the compound, a compound as defined herein for use in the preparation of a medicament to treat the stated disease(s) wherein the compound is to be administered in an effective amount and use of a compound as defined herein for the treatment of the stated disease(s) by administering an effective amount. Such medical uses are all envisaged by the present invention.

The compound of the invention may be identified by general structure (I):

(I)

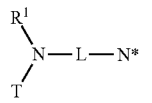

Herein,

T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;

N* is represented by structure (IIa) or (IIb)

(IIa)

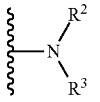

(IIb)

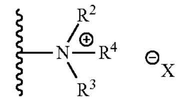

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo) alkoxy moieties, or $R^3$ is absent when the distal nitrogen atom is part of an imine moiety; and $R^4$ is selected from hydrogen (H) or $C_1$-$C_6$ alkyl, wherein the alkyl moiety may be substituted with one or more halogen atoms or (halo) alkoxy moieties;

X is an anion, preferably a pharmaceutically acceptable anion.

The compound according to structure (I) comprises at least two nitrogen atoms; the nitrogen atom to which T is connected, which is also referred to as the "amide nitrogen atom", and the nitrogen atom of the N* moiety, which is also referred to as the "distal nitrogen atom". N* may be an amino moiety, when the covalent bond between the distal nitrogen atom and the adjacent backbone atom is a single bond, or part of an imine moiety, when the covalent bond between the distal nitrogen atom and adjacent backbone atom is a double bond. The distal nitrogen atom may be a neutral or a cationic. In case N* is neutral, the compound according to the invention may also be referred to by general structure (Ia). In case N* is cationic, the compound according to the invention may also be referred to by general structure (Ib).

(Ia)

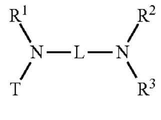

(Ib)

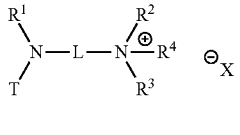

T is a water-soluble vitamin E derivative, wherein the chromanyl or chromanyl quinone framework is substituted with a carboxylic acid at the 2-position. The 2-carboxy variant of vitamin E is also known as Trolox™ (6-hydroxy-2,5,7,8-tetramethylchroman-2-carboxylic acid). Water-soluble vitamin E derivatives are known in the art and include 6-hydroxy-2,5,7,8-tetraalkyl-2-carboxy-chromanyl (general structure (IIIa), also referred to as the "closed form") and its oxidized form 2-(3-hydroxy-3-alkyl-4-oxo-pentyl)-3,5,6-trialkylcyclohexa-2,5-diene-1,4-dione (general structure (IIIb), also referred to as the "open form"). The inventors have found that the open form according to general structure (IIIb) is found as metabolite of the closed form according to general structure (IIIa), when the latter is administered.

(IIIa)

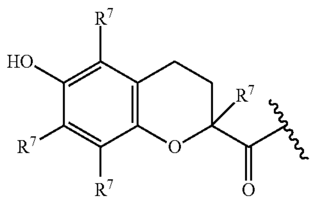

(IIIb)

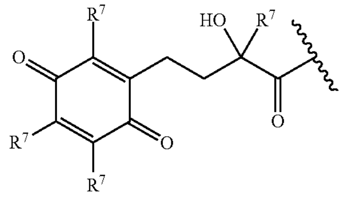

Herein, each occurrence of $R^7$ is individually selected from halogen, alkyl, amino, nitro or —NHCO-alkyl. Preferred options for $R^7$ are halogen and alkyl, most preferably alkyl. In the context of $R^7$, the halogen is preferably fluorine or chlorine, most preferably chlorine. In the context of the alkyl is preferably a $C_1$-$C_6$ alkyl moiety, preferably a $C_1$-$C_6$ alkyl moiety, most preferably methyl. In the context of $R^7$, amino is preferably —$NH_2$. In the context of $R^7$, —NHCO-alkyl is preferably —NHCOMe. Preferably, each of $R^7$ is the same substituent. Most preferably, $R^7$ is methyl. In a preferred embodiment, T is represented by structure (IVa) or (IVb). In other words, structure (IVa) is a preferred embodiment of structure (IIIa), and structure (IVb) is a preferred embodiment of structure (IIIb).

(IVa)

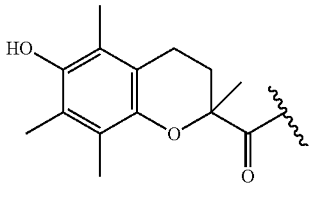

(IVb)

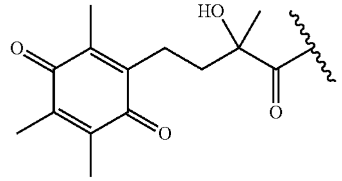

In a preferred embodiment, T is represented by structure (IIIa), preferably by structure (IVa). In an alternative preferred embodiment, T is represented by structure (IIIb), preferably by structure (IVb).

The compound identified by general structure (I) comprises at least one chiral carbon atom (stereocenter), i.e. the atom at the 2-position of T (e.g. of the oxane ring of structure (IIIa) or the butanoic acid moiety of structure (IIIa)). Both the compound having an S-configuration as the compound having an R-configuration of the carbon atom at the 2-position are encompassed in the present invention, as well as mixtures of the different stereoisomers. Such a mixture may have one of the configurations in enantiomeric excess, or may be racemic. Whenever one or more additional stereocenters are present in the compound according to the invention, for example in linker L, each may individually exist in the S-configuration, in the R-configuration, or as a mixture of both configurations. Such a mixture may have one of the configurations in enantiomeric excess, or may be racemic. In case addition stereocenters are present, all diastereomers of the compound of general structure (I), in each possible ratio, are encompassed in the present invention.

In a preferred embodiment, the solubility of the compound of the invention in water, expressed as $\log(P_{ow})$ is between 2.0 and 5.0, preferably between 2.5 and 4.5, more preferably between 3.0 and 4.0. $\text{Log}(P_{ow})$, the logarithm of the partition coefficient between 1-octanol and water, is a well-known measure of water solubility. Compounds having a $\log(P_{ow})$ value between 3 and 4 are ideally balanced between sufficient water solubility for preparation of aqueous solutions or suspensions and sufficient lipophilicity to ensure efficient transport of the compound over the cellular membrane. The skilled person will appreciate how to determine which combinations of L, $R^1$, $R^2$, $R^3$, $R^4$ and X as defined herein to afford a compound having a $\log(P_{ow})$ value between 3 and 4. Suitable tests to define the $\log(P_{ow})$ value of a compound are well-known to the skilled person, and include but are not limited to the shake-flask method, ITIES, the droplet method or using HPLC. The $\log(P_{ow})$ of a compound can also be predicted using QSPR algorithms.

$R^1$ and $R^2$ are each independently selected from hydrogen (H), $C_1$-$C_6$ alkyl or $C_1$-$C_6$ alkenyl, or one or both of $R^1$ and $R^2$ are embedded in a cyclic structure as described here below. Preferably, $R^1$ is H or $C_1$-$C_2$ alkyl or $R^1$ and $R^2$ are joined together and thus form a second linker between the amide nitrogen atom and the distal nitrogen atom, or $R^1$ is joined with a backbone atom of the linker L in a cyclic structure, more preferably $R^1$ is H or $C_1$-$C_2$ alkyl, even more preferably $R^1$ is H or methyl (Me), most preferably $R^1$ is H. Preferably, $R^2$ is H or $C_1$-$C_2$ alkyl or $R^1$ and $R^2$ are joined together and thus form a second linker between the amide nitrogen atom and the distal nitrogen atom, or $R^2$ is joined with a backbone atom of the linker L in a cyclic structure, more preferably $R^2$ is H, $C_1$-$C_2$ alkyl or joined with a backbone atom of the linker L in a cyclic structure, even more preferably $R^2$ is H, methyl (Me) or joined with a backbone atom of the linker L in a cyclic structure. In one embodiment, $R^2$ is H, methyl (Me), preferably $R^2$ is H. In an especially preferred embodiment, $R^2$ is joined with a backbone atom of the linker L in a cyclic structure, as further defined below, preferably a saturated cyclic structure, most preferably a piperidine ring.

In one embodiment, the amide nitrogen atom is connected to the distal nitrogen atom via a second linker. This second linker is defined by joining together $R^1$ on the amide nitrogen atom and $R^2$ on the distal nitrogen atom. Thus, the amide nitrogen atom, the distal nitrogen atom, the first linker and the second linker together form a cyclic structure, preferably a 4-10-membered cyclic structure, more preferably a 5-8-membered cyclic structure, most preferably a 6-membered cyclic structure. In a preferred embodiment, the second linker is a $-CH_2-CH_2-$ or $-CH_2-CH_2-CH_2-$ bridge, most preferably a $-CH_2-CH_2-$ bridge, wherein two or three, preferably two, carbon atoms are present between the amide nitrogen atom and the distal nitrogen atom.

In another embodiment, the amide nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^1$, which is joined together with $R^1$ on the amide nitrogen atom. Thus, the amide nitrogen atom, part of first linker located between the amide nitrogen atom and the atom bearing $R^1$, the backbone atom bearing $R^1$ and the second linker together form the cyclic structure. In this embodiment, the distal nitrogen atom is not included in this cyclic structure, but instead only part of the backbone of the linker is included. In a preferred embodiment, this connection between the amide nitrogen atom and a backbone atom of the linker is a $-CH_2-CH_2-$ or $-CH_2-CH_2-CH_2-$ bridge, most preferably a $-CH_2-CH_2-$ bridge, wherein two or three, preferably two, carbon atoms are present between the amide nitrogen atom and the backbone atom of the linker. Most preferably, the cyclic structure containing the amide nitrogen atom is a fully saturated ring, preferably selected from a piperidine ring, a pyrrolidine ring, a piperazine ring, an imidazolidine ring, a pyrazolidine ring and an azepane ring, more preferably a piperazine ring, a piperidine ring or a pyrrolidine ring, most preferably a piperidine ring.

In another embodiment, the distal nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^2$, which is joined together with $R^2$ on the distal nitrogen atom. Thus, the distal nitrogen atom, part of first linker located between the distal nitrogen atom and the atom bearing $R^2$, the backbone atom bearing $R^2$ and the second linker together form the cyclic structure. In this embodiment, the amide nitrogen atom is not included in this cyclic structure, but instead only part of the backbone of the linker is included. In a preferred embodiment, this connection between the distal nitrogen atom and a backbone atom of the linker is a $-CH_2-CH_2-$ or $-CH_2-CH_2-CH_2-$ bridge, most preferably a $-CH_2-CH_2-$ bridge, wherein two or three, preferably two, carbon atoms are present between the distal nitrogen atom and the backbone atom of the linker. Most preferably, the cyclic structure containing the distal nitrogen atom is a fully saturated ring, preferably selected from a piperidine ring, a pyrrolidine ring, a piperazine ring, an imidazolidine ring, a pyrazolidine ring and an azepane ring, more preferably a piperidine ring or a pyrrolidine ring, most preferably a piperidine ring. It is also possible that a connection exists between $R^1$ on the amide nitrogen atom and an $R^1$ substituent on the linker and between $R^2$ on the distal nitrogen atom and an $R^{2'}$ substituent on the linker.

Among the above-mentioned possibilities for $R^2$, it is most preferred that the distal nitrogen atom is connected to a backbone atom of the linker via a second linker wherein $R^2$ is joined with $R^{2'}$, as further defined here above.

When the distal nitrogen atom is part of an imine moiety, the linker L comprises at least one double bond located between the distal nitrogen atom and the adjacent backbone atom of the linker, or $R^2$ comprises at least one double bond located between the distal nitrogen atom and the adjacent atom of $R^2$ (i.e. $R^2$=$C_1$-$C_6$ alkenyl). In such instances, $R^3$ is absent. In case the distal nitrogen atom is part of an imine moiety, wherein a double bond is located between the distal nitrogen atom and the adjacent backbone atom of the linker, the compound of the invention may be represented by structure (Ic).

(Ic)

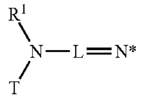

When the distal nitrogen atom is part of an imine moiety is in structure (Ic), it may either be cationic or neutral. The same options for N* as defined by structures (IIa) and (IIb), wherein $R^3$ is absent, apply. In case the distal nitrogen atom is neutral and part of an imine moiety, wherein a double bond is located between the distal nitrogen atom and the adjacent backbone atom of the linker, the compound according to the invention may also be referred to by general structure (Id). In case the distal nitrogen atom is cationic and part of an imine moiety, wherein a double bond is located between the distal nitrogen atom and the adjacent backbone atom of the linker, the compound according to the invention may also be referred to by general structure (Ie).

(Id)

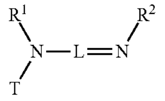

(Ie)

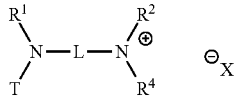

In the context of the present invention, the distal nitrogen being part of an imine moiety includes instances wherein the distal nitrogen atom is part of an heteroaromatic ring, in particular a pyrrole ring, a pyridine ring or a imidazole ring, in which instances a double bond is formally present between the distal nitrogen atom and the adjacent carbon atom either in the linker or in $R^2$. Preferred moieties comprising an imine moiety include guanidine, amidine and pyridine. For guanidine and amidine, one of the nitrogen atoms is substituted to form the connection with the amide nitrogen atom via linker L. For pyridine, one of the carbon atoms is substituted. When the distal nitrogen atom is part of an amine moiety, it is connected to the linker and $R^2$ via two single bonds, and $R^3$ is present. It is preferred that the distal nitrogen atom is part of an amine moiety, i.e. having three or four single bonds to each of $R^1$, $R^2$, $R^3$ and optionally $R^4$.

In the instance that $R^3$ is present, $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl groups or (halo) alkoxy moieties, preferably $R^3$ is H, $C_1$-$C_6$ alkyl, more preferably $R^3$ is H or $C_1$-$C_4$ alkyl, even more preferably $R^3$ is H or $C_1$-$C_2$ alkyl, wherein the alkyl moiety may be substituted with one or more halogen atoms, hydroxyl groups or (halo) alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Preferred substituents for the alkyl moieties are halogen atoms and alkoxy moieties. Suitable moieties for $R^3$ include, preferably are limited to, H, methyl (Me), trifluoromethyl (—$CF_3$), ethyl (Et), isopropyl (iPr), cyclopropyl (-cPr), methylene cyclopropyl (—$CH_2$cPr), n-propyl (n-Pr), 2,2,2-trifluoroethyl (—$CH_2CF_3$), 2-hydroxy-ethyl (—$CH_2CH_2OH$), and methoxymethyl (—$CH_2OCH_3$), more preferably $R^3$ is H or methyl (Me), most preferably $R^3$ is H. Alternatively, $R^3$ is preferably $C_1$-$C_4$ alkyl, wherein the alkyl moiety may be substituted with one or more halogen atoms or (halo) alkoxy moieties, more preferably $R^3$ is $C_1$-$C_2$ alkyl, wherein the alkyl moiety may be substituted with one or more halogen atoms or (halo) alkoxy moieties.

In case the distal nitrogen atom is in cationic form, it formally originates from protonation or alkylation, preferably protonation or methylation of a trivalent nitrogen atom. The trivalent nitrogen atom is preferably an amine moiety, either primary, secondary or tertiary, or an imine moiety, either primary or secondary. The counter ion (X) of the cationic distal nitrogen atom is a negatively charged ion, preferably a monovalent negatively charged ion, more preferably an anion as indicated herein below. The synthesis of the compounds of the invention does not need to encompass the protonation or alkylation of an amine or imine nitrogen atom. The cationic distal nitrogen atom may also be formed via a different route. As such, the cationic distal nitrogen atom only "formally" originates from the protonation or alkylation of an amine or imine nitrogen atom.

$R^4$ is the substituent on the cationic distal nitrogen atom, which originates from formal protonation or alkylation of the amine or imine moiety. Thus, the compound according to this embodiment, in view of the presence of the cationic nitrogen atom and X, is a salt, preferably a pharmaceutically acceptable salt. Pharmaceutically acceptable salts are those salts that are suitable to be administered as drugs or pharmaceuticals to humans and/or animals. The pharmaceutically acceptable salts of the amine or imine moiety of the compound according to the invention are known to those skilled in the art, and originate from formal treatment of the compound with an acid (protonation agent) or an alkylating agent. Suitable acids include organic acids or inorganic acids. Examples of inorganic acids include, but are not limited to, hydrochloric acid (HCl), hydrobromic acid (HBr), hydroiodic acid (HI), sulphuric acid ($H_2SO_4$), nitric acid ($HNO_3$), trifluoroacetic acid (TFAH or $CF_3CO_2H$) and phosphoric acid ($H_3PO_4$). Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids and salicylic acid. When an acid as exemplified here is used to formally prepare the salt, $R^4$ is hydrogen, and the type of acid determines counter ion X. Alternatively, the salt can be formed by formal treatment with an alkylating agent. Suitable alkylating agents include, but are not limited to, $C_1$-$C_6$ alkyl halides (such as methyl iodide, ethyl iodide, propyl iodide, butyl chloride, butyl fluoride, butyl bromide), dimethyl sulphate, dimethyl carbonate, methyl triflate, methyl fluorosulfonate, methyl chlorosulfonate, methyl methanesulfonate and methyl benzenesulfonate. The salt may be prepared by actual treatment of the non-salt compound with an acid or alkylation agent, as indicated above, or via other means known in the art and/or exemplified further below.

$R^4$ is selected from hydrogen (H) or $C_1$-$C_6$ alkyl, wherein the alkyl moiety may be substituted with one or more halogen atoms or (halo)alkoxy moieties, preferably $R^4$ is H or $C_1$-$C_4$ alkyl, wherein the alkyl moiety may be substituted with one or more halogen atoms or (halo)alkoxy moieties, more preferably $R^4$ is H or $C_1$-$C_2$ alkyl, wherein the alkyl moiety may be substituted with one or more halogen atoms or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Suitable moieties for $R^4$ include, preferably are limited to, H, methyl (Me), trifluoromethyl ($—CF_3$), ethyl (Et), isopropyl (iPr), cyclopropyl (-cPr), methylene cyclopropyl ($—CH_2cPr$), n-propyl (n-Pr), 2,2,2-trifluoroethyl ($—CH_2CF_3$), methoxymethyl ($—CH_2OCH_3$). Even more preferably $R^4$ is H or methyl (Me), most preferably $R^4$ is H.

X can be any anion, preferably a physiologically or pharmaceutically acceptable anion, more preferably a monovalent anion. X is preferably selected from F, Cl, Br, I, $HSO_4$, $NO_3$, TFA($CF_3CO_2$), formate, acetate, propionate, glycolate, pyruvate, oxalate, maleate, malonate, succinate, fumarate, tartarate, citrate, benzoate, cinnamate, mandelate, sulfonate and salicylate. Preferably, X is Cl, I, TFA or formate, more preferably Cl, I, TFA or formate, even more preferably X is Cl or formate, most preferably X is Cl. When the cationic nitrogen atom originates from formal protonation, this protonation is preferably accomplished with hydrogen chloride (HCl), trifluoroacetic acid (TFAH or $CF_3CO_2H$) or formic acid (HCOOH), more preferably with HCl or formic acid. Formal methylation is preferably accomplished with methyl iodide (MeI). Thus, in a preferred embodiment, $R^4$=Me when $X=I^-$, and $R^4$=H when $X=Cl^-$, $TFA^-$ or formate.

Appropriate linkers L to connect the amide nitrogen atom to the distal nitrogen atom are linkers preferably comprising 1 to 10 optionally substituted backbone atoms more preferably comprising 1 to 8 optionally substituted backbone atoms. L may thus comprise 1, 2, 3, 4, 5, 6, 7, 8, 9 or 10 optionally substituted backbone atoms. It is preferred that linker L comprises 1 to 10 optionally substituted backbone atoms selected from carbon, nitrogen and oxygen. Herein, backbone atoms are those atoms that make up the shortest chain between the amide nitrogen atom and the distal nitrogen atom. The backbone may be a linear structure, but (part of) the backbone may also be part of a cyclic structure. When the backbone is part a cyclic structure, the backbone is defined as the shortest chain between the amide nitrogen atom and the distal nitrogen atom. In one embodiment, one of the backbone atoms comprises a substituent $R^5$, and one of the backbone atoms comprises a substituent $R^{5'}$, preferably two different backbone atoms comprise the substituents $R^5$ and $R^{5'}$, wherein $R^5$ and $R^{5'}$ are joined to form a cyclic structure, preferably a 4-10-membered cyclic structure, more preferably a 5-8-membered cyclic structure, most preferably a 6-membered cyclic structure. In this embodiment, the amide nitrogen atom and the distal nitrogen atom are not included in the cyclic structure, but instead only part of the backbone of the linker is included. In a preferred embodiment, this connection between the backbone atom(s) of the linker, bearing the $R^5$ and $R^{5'}$ substituents, is a $—(CH_2)_n$-bridge, wherein n=1-6, preferably a $—CH_2—CH_2—$ or $—CH_2—CH_2—CH_2—$ bridge, wherein one to six, preferably two or three, carbon atoms are present between the substituted backbone atom(s) of the linker.

In a preferred embodiment, the backbone atoms are selected from carbon, nitrogen and oxygen, preferably from carbon and nitrogen. Such a backbone according to this preferred embodiment may be identified as $C_{n-m}N_m$, wherein n designates the total number of atoms in the backbone, and m the number of nitrogen atoms in the backbone. Each of n and m is a non-negative integer. Suitable linkers have n=1-10 and m=0-4, preferably n=2-7 and m=0-3, more preferably n=4-7 and m=0-2. Especially preferred linkers have a backbone identified as $C_{n-m}N_m$, wherein n=2 and m=0 ($C_2$); n=5 and m=1 ($C_4N$); n=3 and m=0 ($C_3$); n=4 and m=1 ($C_3N$); n=7 and m=2 ($C_5N_2$); n=4 and m=0 ($C_4$); n=6 and m=1 ($C_5N$); or n=5 and m=0 ($C_5$). Most preferably, all backbone atoms are carbon atoms (m=0).

To fulfil their valence requirements, the carbon and nitrogen backbone atoms of the linker may bear hydrogen atoms, may be substituted, or double or triple bonds may be present between adjacent backbone atoms, as will be understood by the skilled person. In the context of the invention, hydrogen is not regarded a substituent. Whenever an oxygen atom is present as backbone atom in the linker, the skilled person will understand that the oxygen backbone atom bears no hydrogen atoms, substituents or double or triple bonds. Triple bonds may be present between two carbon atoms of the backbone. The backbone atoms, together with the hydrogen atoms and/or the substituents, constitute the linker. In the context of the present invention, "optionally substituted" is used to indicate that an (backbone) atom may bear one or more substituents, or may bear no substituents and sufficient hydrogen atoms may be present instead, to fulfil the valence requirements of said (backbone) atom.

Suitable substituents include but are not limited to halogen, $NH_2$, $NHR^6$, $N(R^6)_2$, $NHNH_2$, $N_3$, $NHC(=O)R^6$, NHC(=O) $NHR^6$, $NHC(=O)NH_2$, $NHC(=O)OR^6$, OH, $OR^6$, $OC(=O)R^6$, $R^6$ (e.g. alkyl, cycloalkyl), aralkyl, alkenyl, alkynyl, aryl, heteroaryl, $OC(=O)OR^6$, $OC(=O)NHR^6$, $O(SO_2)R^6$, $O(SO_2)OH$, $O(PO_2)OH$, SH, $SR^6$, C(=O) $R^6$, alkyl-$NH_2$, alkyl-OH, alkyl-SH, $C(=O)CF_3$, $C(=O)OR^6$, C(=O)OH, C(=O)H, $C(=O)OR^6$, $C(=O)NH_2$, C(=O) $NMe_2$, $C(=O)N(R^6)_2$, $C(=S)NH_2C(=S)SH$, CN, NC, CNO, ONC, OCN, SCN, SNC, CNS, $S(=O)R^6$, $S(=O)_2R^6$, $S(=O)_2(OH)$, $P(=O)(OH)_2$ or $P(=O)(OH)(OR^6)$. Atoms having two or more remaining valencies, such as carbon backbone atoms, may bear a double bonded substituent, such as oxo (=O), imino (=NH or $=NR^6$), thioxo (=S), alkylidene ($=CH_2$ or $=CHR^6$ or $=C(R^6)_2$). Herein, each $R^6$ is independently an alkyl moiety, preferably a $C_1$-$C_6$ alkyl moiety, more preferably a $C_1$-$C_2$ alkyl moiety. Within $R^6$, one or more $CH_2$ moieties may each independently be replaced by one of O, S or NH, and/or one or more CH moieties may be replaced by N. In addition, two substituents on the same atom or on different atoms may be joined to form cyclic structures. If two substituents on a single backbone atom are joined in a cyclic structure, this cyclic structure may be regarded as being connected via a spiro junction to the backbone. If two substituents on different backbone atoms are joined in a cyclic structure, part of this cyclic structure is (part of) the backbone, and the backbone is considered to be the shortest chain of atoms between the amide nitrogen atom and the distal nitrogen atom. The cyclic structures formed as such may be all-carbon or may comprise 0-3 heteroatoms (e.g. N, O, S and/or P), and may comprise 0-3 double bonds. All atoms in these cyclic structures may optionally be substituted. Examples of suitable cyclic structures are optionally substituted cycloalkyl, optionally substituted cycloheteroalkyl, optionally substituted aryl or optionally substituted heteroaryl. As further indicated below, a cyclic structure may also be formed by joining one substituent on a backbone atom with $R^1$ on the amide nitrogen atom or with $R^2$ on the distal nitrogen atom.

In the context of the present invention, the term "alkyl" refers to saturated aliphatic groups including straight-chain, branched-chain, cyclic groups, and combinations thereof, having the number of carbon atoms specified, or if no number is specified, preferably having up to 12 carbon atoms. "Straight-chain alkyl" or "linear alkyl" group refers to alkyl groups that are neither cyclic nor branched, commonly designated as "n-alkyl" groups. One subset of alkyl groups is $C_1$-$C_6$ alkyl, which includes groups such as methyl, ethyl, n-propyl, isopropyl, butyl, n-butyl, isobutyl, sec-butyl, t-butyl, pentyl, n-pentyl, hexyl, cyclopropyl, cyclobutyl, cyclopentyl, cyclohexyl, and any other alkyl group containing between one and six carbon atoms, where the $C_1$-$C_6$ alkyl groups can be attached via any valence on the $C_1$-$C_6$ alkyl groups.

In one embodiment, the backbone atoms are optionally substituted with one or more substituents selected from the group consisting of $R^6$, carboxy, oxo, and primary amino or a backbone atom may be joined with $R^1$ to form a 4-10-membered cyclic structure and/or a backbone atom may be joined with $R^2$ to form a 4-10-membered cyclic structure, or two backbone atoms may be joined to form a cyclic structure, wherein $R^6$ is as defined above, preferably $R^6$ is $C_1$-$C_6$ alkyl, more preferably $C_1$-$C_2$ alkyl. Preferred substituents of the backbone atoms are alkyl, such as methyl (Me or $-CH_3$), carboxyl ($-C(=O)OH$), oxo ($=O$) and primary amino ($-NH_2$).

Preferred linkers are identified here below as $L^1$ to $L^{26}$:

| | | |
|---|---|---|
| $L^1$ = | 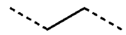 | $-CH_2-CH_2-$ or $-(CH_2)_2-$ |
| $L^2$ = | 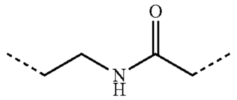 | $-CH_2-CH_2-NH-C(O)-CH_2-$ or $-(CH_2)_2NHC(O)CH_2-$ |
| $L^3$ = | 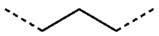 | $-CH_2-CH_2-CH_2-$ or $-(CH_2)_3-$ |
| $L^4$ = | 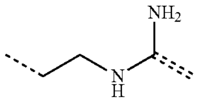 | $-CH_2-CH_2-NH-C(NH_2)=$ or $-(CH_2)_2NHC(NH_2)=$ |
| $L^5$ = | 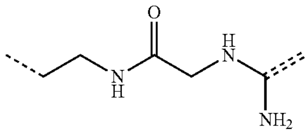 | $-CH_2-CH_2-NH-C(O)-CH_2-NH-C(NH_2)=$ or $-(CH_2)_2NHC(O)CH_2NHC(NH_2)=$ |
| $L^6$ = | 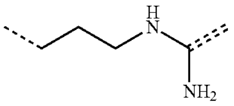 | $-CH_2-CH_2-CH_2-NH-C(NH_2)=$ or $-(CH_2)_3NHC(NH_2)=$ |
| $L^7$ = | 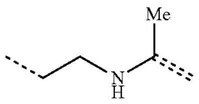 | $-CH_2-CH_2-NH-C(Me)=$ or $-(CH_2)_2NHC(Me)=$ |
| $L^8$ = | 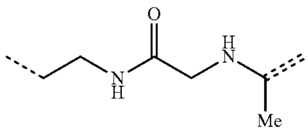 | $-CH_2-CH_2-NH-C(O)-CH_2-NH-C(Me)=$ or $-(CH_2)_2NHC(O)CH_2NHC(Me)=$ |
| $L^9$ = | 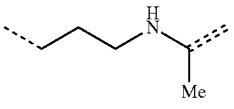 | $-CH_2-CH_2-CH_2-NH-C(Me)=$ or $-(CH_2)_3NHC(Me)=$ |
| $L^{10}$ = | 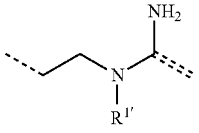 | $-CH_2-CH_2-NR^{1'}-C(NH_2)=$ or $-(CH_2)_2NR^{1'}C(NH_2)=$ |
| $L^{11}$ = | 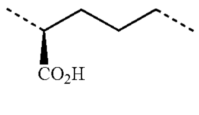 | $-C(CO_2H)-CH_2-CH_2-CH_2-$ or $-C(CO_2H)(CH_2)_3-$ |

-continued $L^{12}$ =

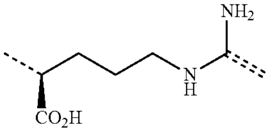

$-C(CO_2H)-CH_2-CH_2-CH_2-NH-C(NH_2)=$ or
$-C(CO_2H)(CH_2)_3NHC(NH_2)=$ $L^{13}$ =

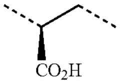

$-C(CO_2H)-CH_2-$ or $-C(CO_2H)CH_2-$ $L^{14}$ =

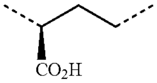

$-C(CO_2H)-CH_2-CH_2-$ or $-C(CO_2H)(CH_2)_2-$ $L^{15}$ =

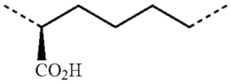

$-C(CO_2H)-CH_2-CH_2-CH_2-CH_2-$ or
$-C(CO_2H)(CH_2)_4-$ $L^{16}$ =

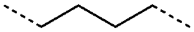

$-CH_2-CH_2-CH_2-CH_2-$ or $-(CH_2)_4-$ $L^{17}$ =

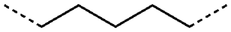

$-CH_2-CH_2-CH_2-CH_2-CH_2-$ or $-(CH_2)_5-$ $L^{18}$ =

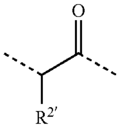

$-CHR^{2'}-C(O)-$ or $-CHR^{2'}C(O)-$ $L^{19}$ =

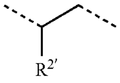

$-CHR^{2'}-CH_2-$ or $-CHR^{2'}CH_2-$ $L^{20}$ =

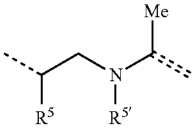

$-CHR^5-CH_2-NR^{5'}-C(Me)=$ or
$-CHR^5CH_2NR^{5'}C(Me)=$ $L^{21}$ =

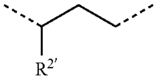

$-CHR^{2'}-CH_2-CH_2-$ or $-CHR^{2'}(CH_2)_2-$ $L^{22}$ =

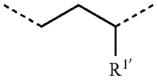

$-CH_2-CH_2-CHR^{1'}-$ or $-(CH_2)_2CHR^{1'}-$ $L^{23}$ =

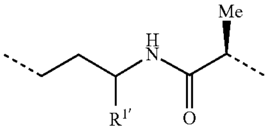

$-CH_2-CH_2-CHR^{1'}-NH-C(O)-C(Me)-$ or
$-(CH_2)_2CHR^{1'}NHC(O)C(Me)-$ $L^{24}$ =

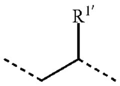

$-CH_2-CHR^{1'}-$ or $-CH_2CHR^{1'}-$

-continued

| | | |
|---|---|---|
| $L^{25}$ = | 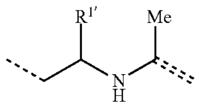 | $—CH_2—CHR^{1'}—NH—C(Me)═$ or $—CH_2CHR^{1'}NHC(Me)═$ |
| $L^{26}$ = | 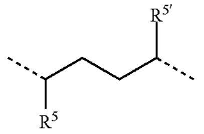 | $—CHR^5—CH_2—CH_2—CHR^{5'}—$ or $—CHR^5(CH_2)_2CHR^{5''}—$ |

Herein, it is preferred that the dashed bond at the left side of each of the structures for $L^1$ to $L^{26}$ indicates the bond between the linker and the amide nitrogen atom, and the dashed bond at the right side of each of the structures for $L^1$ to $L^{26}$ indicates the bond between the linker and the distal nitrogen atom.

Each occurrence of $R^1$ represents the connection of a second linker between the linker and the amide nitrogen atom, wherein $R^1$ is joined with $R^1$ via the second linker, thus forming a 4-10-membered cyclic structure, preferably a 5-8-membered cyclic structure, most preferably a 6-membered cyclic structure, which is built up from the amide nitrogen atom, 1-4 atoms of the backbone of the linker, and 1-4 atoms which make up the bridge joining $R^1$ and $R^{1'}$. Likewise, each occurrence of $R^{2'}$ represents the connection of a second linker between the linker and the cationic nitrogen atom, wherein $R^{2'}$ is joined with $R^2$ via the second linker, thus forming a 4-10-membered cyclic structure, preferably a 5-8-membered cyclic structure, most preferably a 6-membered cyclic structure, which is built up from the cationic nitrogen atom, 1-4 atoms of the backbone of the linker, and 1-4 atoms which make up the bridge joining $R^2$ and $R^{2'}$. Likewise, each occurrence of $R^5$ and $R^{5'}$ represent the connection of a second linker between one backbone atom of the linker, bearing $R^5$, and another backbone atom of the linker, bearing $R^{5'}$, wherein $R^{5'}$ is joined with $R^5$ via the second linker, thus forming a 4-10-membered cyclic structure, preferably a 5-8-membered cyclic structure, most preferably a 6-membered cyclic structure, which is built up from 2-5 atoms of the backbone of the linker, and 1-5 atoms which make up the bridge joining $R^5$ and $R^{5'}$. Thus, in linkers $L^{10}$, $L^{22}$, $L^{23}$, $L^{24}$ and $L^{25}$, $R^{1'}$ is joined to $R^1$ via a second linker, preferably a $—CH_2—CH_2—$ or $—CH_2—CH_2—CH_2—$ bridge, more preferably a $—CH_2—CH_2—$ bridge. Thus, in a compound comprising linker $L^{10}$, wherein $R^{1'}$ and $R^1$ are joined via a $—CH_2—CH_2—$ bridge, the amide nitrogen atom is embedded in a six-membered cyclic structure, which is built up from the amide nitrogen atom, two carbon atoms and one nitrogen atom of the backbone of the linker, and two more carbon atoms which make up the bridge of $R^1$ and $R^{1'}$. This $—CH_2—CH_2—$ bridge between the amide nitrogen atom and the central nitrogen atom in the backbone of linker $L^{10}$ may be represented as $L^1$. Likewise, in linkers $L^{18}$, $L^{19}$ and $L^{21}$, $R^{2'}$ is joined to $R^2$ via a second linker, preferably a $—CH_2—CH_2—$ or $—CH_2—CH_2—CH_2—$ bridge, more preferably a $—CH_2—CH_2—CH_2—$ bridge. Likewise, in linker $L^{20}$ and $L^{26}$, $R^{5'}$ is joined to $R^5$ via a second linker, preferably a $—CH_2—CH_2—$ or $—CH_2—CH_2—CH_2—$ bridge, more preferably a $—CH_2—CH_2—$ bridge.

Linker $L^{26}$ comprises a disubstituted cycloalkyl moiety, preferably a disubstituted cyclohexyl moiety, and may thus occur in either the cis-form or the trans-form, preferably in the trans-form.

Linkers $L^{11}$, $L^{12}$, $L^{13}$, $L^{14}$, $L^{15}$, $L^{18}$ (as long as $R^2$-$R^{2'}$ is not $—C(O)—$), $L^{19}$ (as long as $R^2$-$R^{2'}$ is not $—CH_2—$), $L^{20}$ (as long as $R^5$-$R^{5'}$ is not $—CH_2—$), $L^{21}$ (as long as $R^2$-$R^{2'}$ is not $—CH_2—CH_2—$), $L^{22}$ (as long as $R^1$-$R^{1'}$ is not $—CH_2—CH_2—$), $L^{23}$ (as long as $R^1$-$R^{1'}$ is not $—CH_2—CH_2—$), $L^{24}$ (as long as $R^1$-$R^{1'}$ is not $—CH_2—$) and $L^{25}$ (as long as $R^1$-$R^{1'}$ is not $—CH_2—$) comprise an additional stereocenter. The stereoisomer, when indicated in the structures of those linkers, above is meant as illustrative, not as limiting. As indicated further above, each stereocenter present in the compounds according to the invention may individually be present in each of its stereoisomeric forms, either S or R, or as a mixture of both isomers in any ratio. In view of the stereocenter already present at the 2-position of T, the compounds having these linkers may be (R,R); (S,R); (R,S); or (S,S). Throughout the description, the first designator (R or S) of the configuration is for the 2-position of T, and the second designator thereof defines the configuration of the additional stereocenter that may be present in the compound according to the invention.

Especially preferred linkers are $L^5$, $L^8$, $L^{11}$, $L^{12}$, $L^{16}$, $L^{17}$, $L^{19}$, $L^{21}$ and $L^{26}$. Even more preferred linkers are $L^{11}$, $L^{16}$, $L^{19}$ and $L^{26}$, and most preferably the linker is $L^{19}$. Preferably, $L^{19}$ is combined with $R^2$-$R^{2'}$=$L^1$ or $L^3$, most preferably with $R^2$-$R^{2'}$=$L^3$. Preferably, $L^{21}$ is combined with $R^2$-$R^{2'}$=$L^1$ or $L^3$, most preferably with $R^2$-$R^{2'}$=$L^1$. Preferably, $L^{26}$ is combined with $R^5$-$R^{5'}$=$L^1$ or $L^3$, more preferably with $R^5$-$R^{5'}$=$L^1$, most preferably wherein the cyclohexyl is trans-1,4-disubstituted. Especially preferred is the combination of linker $L^{19}$ with $R^2$-$R^{2'}$=$L^3$ and $R^3$=H, Me, Et, iPr, $CH_2OCH_3$ or $CH_2CF_3$, more preferably $R^3$=Me, Et, iPr or $CH_2CF_3$, most preferably $R^3$=H In case N* is according to structure (IIa), it is preferred that linker L contains 1-5 optionally substituted backbone atoms and/or linker L contains at least one backbone atom other than carbon. In case N* is according to structure (IIa), it is especially preferred that the distal nitrogen atom is connected to a backbone atom of the linker via a second linker wherein $R^2$ is joined with $R^{2'}$, more preferably wherein the cyclic structure thus formed is a piperidine ring, a pyrrolidine ring, an imidazolidine ring, a pyrazolidine ring or an azepane ring, most preferably a piperidine ring, and/or at least one of the backbone atoms is substituted with a carboxylic acid moiety. In case N* is according to structure (IIa), it is especially preferred that L is any one of $L^2$, $L^4$-$L^{21}$, $L^{23}$, $L^{25}$ and $L^{26}$, more preferably one of $L^5$, $L^8$, $L^{11}$, $L^{12}$, $L^{16}$, $L^{17}$, $L^{19}$, $L^{21}$ and $L^{26}$. In case N* is according to structure (IIb), it is preferred that $R^4$ is H or Me, more preferably $R^4$ is H, and X is Cl, I, TFA or formate, even more preferably X is Cl or formate, most preferably X is Cl. In case N* is according to structure (IIb), it is preferred that linker L contains 3-10 backbone atoms, or 2 backbone atoms of which one is connected to the distal nitrogen atom via a second linker. In case N* is according to structure (IIb), it is especially preferred that L is any one of $L^2$-$L^{26}$, more preferably one of $L^5$, $L^8$, $L^{11}$, $L^{12}$, $L^{16}$, $L^{17}$, $L^{19}$, $L^{11}$ and $L^{26}$.

In one embodiment, linker L is $L^1$ and $R^1$ and $R^2$ are joined together in a cyclic structure via a second linker $L^1$, thus forming a six-membered piperazine ring including in total four carbon atoms from the two linkers, the amide nitrogen atom and the distal nitrogen atom. In one embodiment, linker L is $L^{19}$ and $R^2$ and $R^{2'}$ are joined together in a cyclic structure via a second linker $L^3$, thus forming a six-membered piperidene ring including in total five carbon atoms from the linkers and the distal nitrogen atom.

In a preferred embodiment, the compound is represented by general structure (I), wherein:

- L is a linker between the amide nitrogen atom and the distal nitrogen atom;
- N* is according to structure (IIa);
- T is according to structure (IIIa) or (IIIb), wherein $R^7$ is a $C_1$-$C_6$ alkyl moiety;
- $R^1$ is selected from hydrogen (H), $C_1$-$C_6$ alkyl or $C_1$-$C_6$ alkenyl, or $R^1$ is joined with a backbone atom of the linker L in a cyclic structure;
- $R^2$ is joined with a backbone atom of the linker L to form a cyclic structure selected from a piperidine ring, a pyrrolidine ring, an imidazolidine ring, a pyrazolidine ring or an azepane ring; and
- $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety.

In an alternative preferred embodiment, the compound according to the invention is represented by general structure (I), wherein

- L is a linker between the amide nitrogen atom and the distal nitrogen atom comprising 3-10 backbone atoms, or 2 backbone atoms of which one is connected to the distal nitrogen atom via a second linker;
- N* is according to structure (IIb);
- T is according to structure (IIIa) or (IIIb), wherein $R^7$ is a $C_1$-$C_6$ alkyl moiety;
- $R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
- $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety;
- $R^4$ is selected from hydrogen (H) or $C_1$-$C_6$ alkyl, wherein the alkyl moiety may be substituted with one or more halogen atoms or (halo)alkoxy moieties; and
- X is an anion, preferably a pharmaceutically acceptable anion.

Particularly preferred compounds in the context of the present invention are identified here below by structures (VI)-(IX). Thus, in a preferred embodiment, the compound of general structure (I) is represented by structure (VI):

(VI)

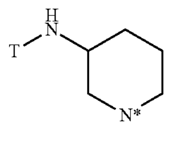

Herein, $R^2$ is joined with a backbone atom via a second linker forming a cyclic structure, thus N* is —$NR^3$ or —$N^+R^3R^4X^-$. Herein, $R^3$, $R^4$, X and T are as defined above. Preferably, T is according to structure (IIIa) or (IIIb), more preferably according to structure (IVa) or (IVb). In the compound according to structure (VI), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VI) may be (R,R); (S,R); (R,S); or (S,S), preferably it is (S,R).

In a preferred embodiment, the compound of general structure (I) is represented by structure (VIIa) or (VIIb):

(VIIa)

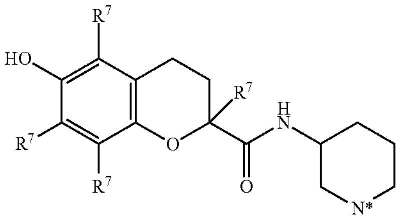

(VIIb)

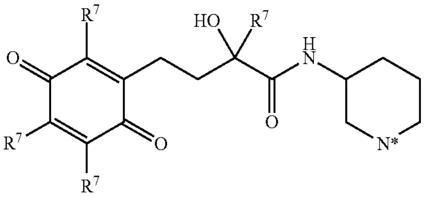

Herein, $R^2$ is joined with a backbone atom via a second linker forming a cyclic structure, thus N* is —$NR^3$ or —$N^+R^3R^4X^-$. Herein, $R^3$, $R^4$, X and $R^7$ are as defined above. In the compound according to structure (VIIa) or (VIIb), $R^7$ is preferably methyl. In the compound according to structure (VIIa) or (VIIb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VIIa) or (VIIb) may be (R,R); (S,R); (R,S); or (S,S), preferably it is (S,R). In one embodiment, the compound of general structure (I) is represented by structure (VIIa). In an alternative embodiment, the compound of general structure (I) is represented by structure (VIIb).

In a preferred embodiment, the compound of general structure (I) is represented by structure (VIIIa) or (VIIIb):

(VIIIa)

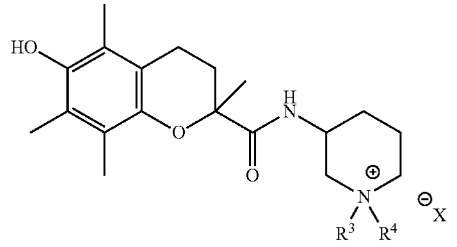

(VIIIb)

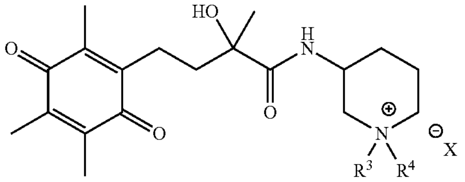

Herein, $R^2$ is joined with a backbone atom via a second linker forming a cyclic structure and N* is —$N^+R^3R^4X$—. Herein, $R^3$, $R^4$ and X are as defined above. In the compound according to structure (VIIIa) or (VIIIb), $R^3$ is preferably H or $C_1$-$C_2$ alkyl, most preferably $R^3$ is H. In the compound according to structure (VIIIa) or (VIIIb), $R^4$ is preferably H or $C_1$-$C_2$ alkyl, most preferably $R^4$ is H. In the compound according to structure (VIIIa) or (VIIIb), X is preferably Cl, I, TFA or formate, most preferably X is Cl. In the compound according to structure (VIIIa) or (VIIIb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VIIIa) or (VIIIb) may be (R,R); (S,R); (R,S); or (S,S), preferably it is (S,R). In one embodiment, the compound of general structure (I) is represented by structure (VIIIa). In an alternative embodiment, the compound of general structure (I) is represented by structure (VIIIb).

In a preferred embodiment, the compound of general structure (I) is represented by structure (IXa) or (IXb):

(IXa)

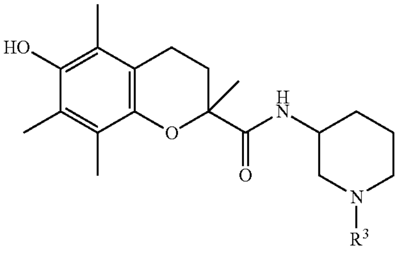

(IXb)

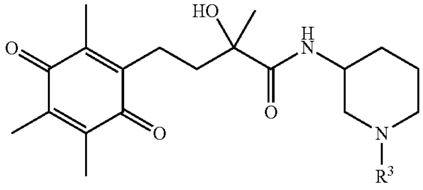

Herein, $R^2$ is joined with a backbone atom via a second linker forming a cyclic structure and N* is —$NR^3$. Herein, $R^3$ is as defined above. In the compound according to structure (VIIIa) or (VIIIb), $R^3$ is preferably H or $C_1$-$C_2$ alkyl, most preferably $R^3$ is H. In the compound according to structure (IXa) or (IXb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (IXa) or (IXb) may be (R,R); (S,R); (R,S); or (S,S), preferably it is (S,R). In one embodiment, the compound of general structure (I) is represented by structure (IXa). In an alternative embodiment, the compound of general structure (I) is represented by structure (IXb).

In a preferred embodiment, the compound is according to general structure (I), wherein T is represented by structure (IVa), N* is represented by structure (IIa) or by structure (IIb) wherein $R^4$=H and X=Cl, and wherein:

(A) L=$L^1$, $R^1$-$R^2$=$L^1$, $R^3$=H;
(B) L=$L^1$, $R^1$=H, $R^2$=H, $R^3$=H;
(C) L=$L^2$, $R^1$=H, $R^2$=H, $R^3$=H;
(D) L=$L^3$, $R^1$=H, $R^2$=H, $R^3$=H;
(E) L=$L^4$, $R^1$=H, $R^2$=H, $R^3$=absent;
(F) L=$L^5$, $R^1$=H, $R^2$=H, $R^3$=absent;
(G) L=$L^6$, $R^1$=H, $R^2$=H, $R^3$=absent;
(H) L=$L^3$, $R^1$=H, $R^2$=Me, $R^3$=Me;
(I) L=$L^1$, $R^1$=H, $R^2$=Me, $R^3$=Me;
(J) L=$L^7$, $R^1$=H, $R^2$=H, $R^3$=absent;
(K) L=$L^8$, $R^1$=H, $R^2$=H, $R^3$=absent;
(L) L=$L^9$, $R^1$=H, $R^2$=H, $R^3$=absent;
(M) L=$L^{10}$, $R^1$-$R^1$=$L^1$, $R^2$=H, $R^3$=absent;
(N) L=$L^{11}$, $R^1$=H, $R^2$=H, $R^3$=H;
(O) L=$L^{12}$, $R^1$=H, $R^2$=H, $R^3$=absent;
(P) L=$L^{13}$, $R^1$=H, $R^2$=H, $R^3$=H;
(Q) L=$L^{14}$, $R^1$=H, $R^2$=H, $R^3$=H;
(R) L=$L^{15}$, $R^1$=H, $R^2$=H, $R^3$=H;
(S) L=$L^{11}$, $R^1$=H, $R^2$=Me, $R^3$=Me
(T) L=$L^{16}$, $R^1$=H, $R^2$=H, $R^3$=H;
(U) L=$L^{17}$, $R^1$=H, $R^2$=H, $R^3$=H;
(V) L=$L^{16}$, $R^1$=H, $R^2$=Me, $R^3$=Me;
(W) L=$L^{18}$, $R^1$=H, $R^2$-$R^{2'}$=$L^3$, $R^3$=H;
(X) L=$L^{19}$, $R^1$=H, $R^2$-$R^{2'}$=$L^3$, $R^3$=H;
(Y) L=$L^{20}$, $R^1$=H, $R^2$=H, $R^5$-$R^{5'}$=$L^3$, $R^3$=absent;
(Z) L=$L^{21}$, $R^1$=H, $R^2$-$R^2$=$L^1$, $R^3$=H;
(AA) L=$L^{22}$, $R^1$-$R^1$=$L^1$, $R^2$=H, $R^3$=H;
(AB) L=$L^{23}$, $R^1$-$R^1$=$L^1$, $R^2$=H, $R^3$=H;
(AC) L=$L^{24}$, $R^1$-$R^1$=$L^3$, $R^2$=H, $R^3$=H;
(AD) L=$L^{25}$, $R^1$-$R^1$=$L^3$, $R^2$=H, $R^3$=absent;
(AE) L=$L^{26}$, $R^1$=H, $R^2$=H, $R^5$-$R^{5'}$=$L^1$, $R^3$=H.
(AF) L=$L^{19}$, $R^1$=H, $R^2$-$R^{2'}$=$L^3$, $R^3$=Me;
(AG) L=$L^{19}$, $R^1$=H, $R^2$-$R^{2'}$=$L^1$, $R^3$=H;
(AH) L=$L^{21}$, $R^1$=H, $R^2$-$R^{2'}$=$L^1$, $R^3$=Me.

It is thus preferred that the compound according to structure (I) is selected from compounds A-AH defined above. Especially preferred compounds are selected from F, K, N, O, U, V, T, X, Z, AE, AF, AG and AH, more preferably N, T, X and AE, most preferably X. Herein, N* is preferably represented by structure (IIb) wherein $R^4$=H and X=Cl.

Compound F may have the R-configuration, the S-configuration or a mixture thereof, preferably compound F is a mixture of the R- and S-enantiomers, more preferably a racemic mixture. Compound K may have the R-configuration, the S-configuration or a mixture thereof, preferably compound K is a mixture of the R- and S-enantiomers, more preferably a racemic mixture. Compound N may have the R,R-configuration, R,S-configuration, S,R-configuration, the S,S-configuration or any mixture thereof, preferably compound N has the R,R-configuration or the S,R-configuration, most preferably the R,R-configuration. Compound O may have the R,R-configuration, R,S-configuration, S,R-configuration, the S,S-configuration or any mixture thereof, preferably compound O is a mixture of the R,S- and S,S-diastereomers more preferably about 1/1 (mol/mol) mixture. Compound U may have the R-configuration, the S-configuration or a mixture thereof, preferably compound U has the R-configuration or the S-configuration. Compound V may have the R-configuration, the S-configuration or a mixture thereof, preferably compound V has the R-configuration. Compound T may have the R-configuration, the S-configuration or a mixture thereof, preferably compound T has the R-configuration or the S-configuration, most preferably the R-configuration. Compound X may have the R,R-configuration, R,S-configuration, S,R-configuration, the S,S-configuration or any mixture thereof, preferably compound X has the R,S-configuration or the S,R-configuration, most preferably the S,R-configuration. Compound Z may have the R-configuration, the S-configuration or a mixture thereof, preferably compound Z is a mixture of the R- and S-enantiomers, more preferably a racemic mixture. Compound AE may have the R, trans-configuration, R,cis-configuration, S, trans-configuration, the S,cis-configuration or any mixture thereof, preferably compound AE has the R,trans-configuration or the S,trans-configuration, most preferably the R,trans-configuration. Compound AF may have the R,R-configuration, R,S-configuration, S,R-configuration, the S,S-configuration or any mixture thereof, preferably compound AF has the S,R-configuration. Compound AG may have the R,R-configuration, R,S-configuration, S,R-configuration, the S,S-configuration or any mixture thereof, preferably compound AG has the S,S-configuration or the S,R-configuration. Compound AH may have the R-configuration, the S-configuration or a mixture thereof, preferably compound AH has the S-configuration. Herein, the first designator (R or S) of the configuration is for the 2-position of T, and in case an additional stereocenter is present in the compound according to the invention, the second designator thereof defines the configuration thereof.

The most preferred compounds include compound N in the R,R-configuration (R,R-N), compound T in the R-configuration (R-T), compound AE in the R,trans-configuration (R,trans-AE) and compound X in any configuration, most preferably the compound according to the invention is compound X in the S,R-configuration (S,R-X). In one embodiment, these most preferred compounds according to the invention are compound N in the R,R-configuration (R,R-N), compound T in the R-configuration (R-T), compound AE in the R,trans-configuration (R,trans-AE) and compound X in any configuration, wherein $R^4$=H and X=Cl, more preferably the compound according to the invention is compound X in the S,R-configuration (S,R-X), wherein $R^4$=H and X=Cl. In one embodiment, these most preferred compounds according to the invention are compound N in the R, R-configuration (R,R-N), compound T in the R-configuration (R-T), compound AE in the R,trans-configuration (R,trans-AE) and compound X in any configuration, wherein N* is represented by structure (IIa), most preferably the compound according to the invention is compound X in the S,R-configuration (S,R-X), wherein N* is represented by structure (IIa).

The invention also includes all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures.

Compounds as described herein above are members of a new class of drugs, acting as potent intracellular redox-modulating agents essential for the control of oxidative and redox pathologies. Therefore, a compound as defined herein above is for use in treating, preventing, or suppressing symptoms associated with a mitochondrial disorder or with a disease or condition associated with mitochondrial dysfunction by administration of an effective dose. The effective dose is further defined herein below. The methods of the invention, preferably comprise administering to a subject an effective dose of one or more compounds as herein defined, and an acceptable carrier, excipient or vehicle, preferably a pharmaceutically or physiologically acceptable carrier, excipient or vehicle.

Preferably, the compound (or compounds) is (are) administered in a total daily dose. It is understood that the terms "daily dose" and "total daily dose" are used interchangeably herein. In particular, the total daily dose can be administrated over one or several units (doses) per day as detailed herein below, More preferably, the total daily dose is therapeutically effective and preferably also well tolerated, e.g. does not cause a side effect as detailed herein below. A side effect is herein defined as an effect, whether therapeutic or adverse, that is secondary to the one intended. Hence, a side effect in the context of the invention is an effect, whether therapeutic or adverse, that is secondary to the treatment, prevention, or suppression of symptoms associated with a mitochondrial disorder or with a disease or condition associated with mitochondrial dysfunction. In a preferred embodiment, the side effect is an adverse effect. Furthermore, it is herein understood that a side effect preferably is an effect that is caused by the compound.

Side effects can be graded as mild (grade 1), moderate (grade 2), severe (grade 3) or potentially life threatening (grade 4). In a preferred embodiment of the invention, the administered total daily dose is well-tolerated, e.g. does not cause any side effects that are grade 1, 2, 3 and/or 4, preferably the administered total daily dose does not cause any side effects that are grade 1, 2 and/or grade 3 and more preferably the administered total daily dose does not cause any side effects that are grade 2 or 3.

In a preferred embodiment, the administered dose does not cause a side effect that is very common, common (frequent), uncommon (infrequent), rare or very rare. A very common side effect is herein defined as the probability (chance) of experiencing the side effect is >=1/10, a common (frequent) side effect is herein defined as the probability of experiencing the side effect is >=1/100 and <1/10, an uncommon (infrequent) side effect is herein defined as the probability of experiencing the side effect is >=1/1000 and <1/100, a rare side effect is herein defined as the probability of experiencing the side effect is >=1/10000 and <1/1000 and a very rare side effect is herein defined as the probability of experiencing the side effect is <1/10000.

In an embodiment of the invention, the administered total daily dose does not cause a very common, common, uncommon, rare or very rare side effect. More preferably the administered dose does not cause a very common, common, uncommon or rare side effect, even more preferably the administered total daily dose does not cause a very common, common or uncommon side effect and even more preferably the administered total daily dose does not cause a very common or common side effect. Most preferably the administered total daily dose does not cause a very common side effect.

In a preferred embodiment, the compound is administered at a total daily dose that does not cause a side effect selected from the group consisting of nausea, headache, psychiatric symptoms, dizziness, oral paraesthesia and changes in cardiac electrophysiology. Preferably, the compound is administered at a dose that does not cause a change in cardiac electrophysiology, more specifically the administered dose does not cause at least one of a prolonged QTc interval, an increased heart rate (HR) or an increased QRS interval. More preferably, the administered dose does not cause a QTc prolongation e.g. as indicated by ECG and telemetry, in particularly as indicated by the QTcB, the Bazett corrected QT interval or by the QTcF, the Frederica corrected QT interval, whereby the QTcF is the most preferred as the administered compound may also affect heart rate. In a particularly preferred embodiment, the administered total daily dose does not affect repolarization, more precisely, does not effect at least one of TpTe interval, T-wave amplitude and T-wave symmetry, under a prolonged corrected QT interval.

In a further preferred embodiment, the compound is administered at a total daily dose that does not result in a clinically relevant abnormal ECG and/or an abnormal change in cardiac functioning as defined herein below. More preferably, the subject to be treated does not have a significant change in QTc interval after administration of the compound. Even more preferably, the subject to be treated does not have an increase in QTc interval of more than 70, 60, 50, 45, 40, 35, 30 or 25 ms after administration of the compound. In a further preferred embodiment, the administered total daily dose does not result in a very common, common, uncommon, rare or very rare probability of experiencing a side effect, wherein the side effect is preferably specified as a change in cardiac electrophysiology, more preferably a QT prolongation as defined herein. Preferably, the total daily dose does not result in a very common, common or uncommon probability of experiencing a side effect, wherein the side effect is specified as a change in cardiac electrophysiology, more preferably a QT prolongation. Most preferably, the total daily dose does not result in a very common or common probability of experiencing a side effect, wherein the side effect is specified as a change in cardiac electrophysiology, more preferably a QT prolongation.

In a further embodiment of the invention, the compound disclosed herein for use in treating, preventing, or suppressing symptoms associated with a mitochondrial disorder or with a disease or condition associated with mitochondrial dysfunction is administered in a total daily dose in the range of about 10 to 800 mg. In particular, it is disclosed herein that the oral administration of a total daily dose of 800 mg or more may increase the frequency of side effects. In particular, the oral administration of a total daily dose of 800 mg or more significantly increases the frequency of nausea, headache, psychiatric symptoms, dizziness, oral paraesthesia and changes in cardiac electrophysiology. In addition, doses within this ranges specified herein have been shown to be effective. Preferred compounds for use in the method as specified herein are indicated herein above.

In a further preferred embodiment, the compound as defined herein is for use in treating, preventing, or suppressing symptoms associated with a mitochondrial disorder or with a disease or condition associated with mitochondrial dysfunction, wherein the total daily dose that is administered is in the range of about 20 to 800 mg, preferably within the range of about 30 to 800 mg or 30 to 700 mg, or within the range of about 20 to 700 mg or 20 to 600 mg.

In an even further preferred embodiment, the total daily dose that is administered is in the range of about 30 to 600 mg, more preferably in the range of about 30 to 500 mg, about 30 to 450 mg or about 30 to 400 mg.

In a further preferred embodiment, the total daily dose that is administered is in the range of between about 30 to 350 mg and wherein even more preferably the total daily dose that is administered is in the range of between about 30 to 300 mg.

In a further preferred embodiment, the total daily dose that is administered is in the range of about 50 to 600 mg, more preferably in the range of about 50 to 500 mg, about 50 to 400 mg, about 50 to 350 mg or about 50 to 300 mg.

In a further preferred embodiment, the total daily dose is in the range of about 50 to 250 mg, 100 to 250 mg or total daily dose that is administered is in the range of about 150 to 250 mg.

In the most preferred embodiment, the total daily dose that is administered is about 200 mg. The term "about" as used herein is to be understood as that there may be a certain tolerance around the specified dose. In particular, the term "about" as used herein is herein understood that there is preferably a tolerance of 0.1, 0.5 or 1% around the specified dose.

In a preferred embodiment of the invention, "subject", "individual", or "patient" is understood to be an individual organism, preferably a vertebrate, more preferably a mammal, even more preferably a primate and most preferably a human.

The dose as defined herein is preferably suitable for administration to humans. Hence, in a preferred embodiment, the invention pertains to a compound as defined herein above, for use in treating, preventing, or suppressing symptoms associated with a mitochondrial disorder or with a disease or condition associated with mitochondrial dysfunction by administration of an effective dose as defined herein, wherein the subject to be treated is a primate, wherein preferably the subject is a human.

In a further preferred embodiment of the invention, the human is an adult, e.g. a person that is 18 years or older. In addition, it is herein understood that the average weight of an adult person is 62 kg, although the average weight is known to vary between countries. In another embodiment of the invention the average weight of an adult person is therefore between about 50-90 kg. It is herein understood that the effective dose as defined herein is not confined to subjects having an average weight. Preferably, the subject has a BMI (Body Mass Index) between 18.0 to 40.0 $kg/m^2$, and more preferably a BMI between 18.0 to 30.0 $kg/m^2$.

Alternatively, the subject to be treated is a child, e.g. a person that is 17 years or younger. In addition, the subject to be treated may be a person between birth and puberty or between puberty and adulthood. It is herein understood that puberty starts for females at the age of 10-11 years and for males at the age of 11-12 year. Furthermore, the subject to be treated may be a neonate (first 28 days after birth), an infant (0-1 year), a toddler (1-3 years), a preschooler (3-5 years); a school-aged child (5-12 years) or an adolescent (13-18 years).

In a further preferred embodiment, the subject to be treated has a clinically relevant normal ECG and/or a normal cardiac functioning. A clinically relevant normal ECG is well-known. In particular, the clinical interpretation of an ECG can be performed by the person skilled in the art (e.g.

a cardiologist). Nevertheless, by way of example a "normal ECG" may herein be understood as an ECG (of an adult person) that preferably fulfils at least one of the criteria specified in table 1 below. More preferably, the subject to be treated fulfils at least 2, 3, 4, 5, 6 or, 7 criteria specified in table 1 below. More preferably, the subject to be treated fulfils 5, 6 or 7 criteria specified in table 1 below and most preferably the subject to be treated fulfils all criteria specified in table 1 below.

It is however understood that any deviations from the averages mentioned in table 1 does not imply that the subject to be treated has a clinically relevant abnormal ECG. Whether an abnormal ECG is a clinically relevant abnormal ECG may be dependent on external circumstances and may require a further assessment by e.g. a cardiologist.

TABLE 1

Normal adult 12-lead ECG

| Criterion | Details |
|---|---|
| normal sinus rhythm | each P wave is followed by a QRS<br>P waves normal for the subject<br>Normally the P wave rate is 60-100 bpm with <10% variation |
| normal P waves | upright in leads I, aVF and V3-V6<br>normal duration of less than or equal to 0.11 seconds<br>polarity is positive in leads I, II, aVF and V4-V6; diphasic in leads V1 and V3; negative in aVR<br>shape is generally smooth, not notched or peaked |
| normal PR interval | Normally between 0.12 and 0.20 seconds |
| normal QRS complex | Duration less than or equal to 0.12 seconds, amplitude greater than 0.5 mV in at least one standard lead, and greater than 1.0 mV in at least one precordial lead. Upper limit of normal amplitude is 2.5-3.0 mV.<br>small septal Q waves in I, aVL, V5 and V6 (duration less than or equal to 0.04 seconds; amplitude less than ⅓ of the amplitude of the R wave in the same lead).<br>represented by a positive deflection with a large, upright R in leads I, II, V4-V6 and a negative deflection with a large, deep S in aVR, V1 and V2<br>in general, proceeding from V1 to V6, the R waves get taller while the S waves get smaller. At V3 or V4, these waves are usually equal. This is called the transitional zone. |
| normal QT interval | Durations normally less than or equal to 0.44. |
| Normal QTc interval | Durations normally less than or equal to 0.43 seconds for males and 0.45 seconds for females. |
| normal ST segment | isoelectric, slanting upwards to the T wave in the normal ECG<br>can be slightly elevated (up to 2.0 mm in some precordial leads)<br>never normally depressed greater than 0.5 mm in any lead |
| normal T wave | T wave deflection should be in the same direction as the QRS complex in at least 5 of the 6 limb leads<br>normally rounded and asymmetrical, with a more gradual ascent than descent<br>should be upright in leads V2-V6, inverted in aVR<br>amplitude of at least 0.2 mV in leads V3 and V4 and at least 0.1 mV in leads V5 and V6<br>isolated T wave inversion in an asymptomatic adult is generally a normal variant |

Similarly, a normal cardiac functioning is well-known and the clinical evaluation can be assessed by a person skilled in the art (e.g. a cardiologist). It is herein understood that the subject to be treated may have a cardiac functioning that is not conform normal (healthy) output, and the normal cardiac functioning of the subject to be treated may be dependent on the mitochondrial disorder, condition or disease. Hence in a preferred embodiment of the invention, normal cardiac functioning is herein defined as not having at least one of symptomatic heart failure, signs of ischemic heart disease and a left ventricular ejection fraction of less than 45%. Hence in a preferred embodiment, the subject to be treated does not have at least one of symptomatic heart failure, signs of ischemic heart disease and a left ventricular ejection fraction of less than 45%. The person skilled in the art (e.g. a cardiologist) knows how to evaluate symptomatic heart failure, signs of ischemic heart disease and a left ventricular ejection fraction of less than 45%.

In a further preferred embodiment of the invention, the subject to be treated does not have an abnormal QTc interval. Preferably, the QTc as defined herein is a QTcB, the Bazett corrected QT interval or the QTcF, the Frederica corrected QT interval. More preferably, the QTc as defined herein is a QTcF. Preferably, the subject to be treated does not have a shortened or prolonged QTc interval and more preferably the subject to be treated does not have a prolonged QTc interval. More preferably the subject to be treated does not have a prolonged QTc due to a prolonged TpTe interval.

In a particularly preferred embodiment, the subject to be treated does not have an abnormal QTc of more than 500 ms. More precisely, when the subject to be treated is a male subject, the subject does not have an abnormal QTc of more than 500, 490, 480, 470, 460, 450, 440, 430, 420, 410 or 400 ms, preferably the subject does not have an abnormal QTc of more than 450, 440, 430 or 420 ms. In case the subject to be treated is a female, the female subject does not have an abnormal QTc of more than 470, 460, 450 or 440 ms, preferably the subject does not have an abnormal QTc of more than 450 or 440 ms.

In a further preferred embodiment, the subject to be treated does not have an abnormal T-wave, such as an abnormal T-wave amplitude and/or an abnormal T-wave symmetry and/or a prolonged TpTe interval.

Hence, in a most preferred embodiment, the subject to be treated does not have an abnormal QTc of more than 500 ms and/or an abnormal T-wave morphology.

Preferably, the compound for a use as defined herein should not be given to a subject having a risk of developing torsades de pointes. Risk factors include the presence of (concomitant) medications that prolong QT, such as clarithromycin, levofloxacin and haloperidol as well as certain conditions/disorders. For example, inherited long QT syndrome significantly increases the risk of episodes of torsades de pointes. Similarly, the subject to be treated does preferably not have a condition selected from the group consisting of cardiovascular disease, alcoholic liver disease, obesity, hypertension and electrolyte disturbances.

In a further embodiment of the invention, the mitochondrial disorder and/or the disease or condition associated with mitochondrial dysfunction preferably is a condition characterised by an OXPHOS deficiency, preferably as characterized by a decreased content or activity of the individual or combined multi-protein enzyme complexes and/or decrease oxygen consumption, and/or decreased pyruvate oxidation rates, and/or decreased ATP production rates. Every cell needs energy. Shortage of energy therefore affects the activity of every cell. Thus in principle every cell is affected by a sub-optimal amount and/or activity of one or more of the OXPHOS complexes. However, the actual amount that is sub-optimal varies from cell to cell. Cells that have a relatively high energy consumption such as brain and muscle cells typically require a higher amount of OXPHOS system complexes than cells that have a low energy consumption, such as resting T-cells. Thus, the cells that are affected by said deficiency associated with an oxidative phosphorylation deficiency are typically, but not necessarily muscle cells or brain cells. Mitochondrial disorders are pleiotropic in their clinical manifestation. Various tissues can be affected like for instance pancreas, heart, liver, eye, inner ear, blood, colon and kidney. In addition, also cells from non-clinically affected tissues like fibroblasts often show a mitochondrial defect. Cells affected by an OXPHOS deficiency can be treated and provided with a higher amount of OXPHOS complex by providing the cell with a compound as defined herein. A cell is affected by an OXPHOS deficiency when the OXPHOS capacity is lower than normal (i.e. a comparable cell of the same species from a healthy individual). The capacity is typically lower over a prolonged period of time. Apart from being derived from an individual with an OXPHOS deficiency there are several methods to determine whether a cell has an OXPHOS deficiency, such test encompass but are not limited to oxygen consumption, ATP production capacity, and enzymatic activities of individual OXPHOS complexes (Chretien and Rustin J Inherit Metab Dis. 2003;_26_(2-3): 189-98). It now has surprisingly been found that a compound of the invention is well-tolerated in humans when administered at total daily dose below 800 mg.

In a preferred embodiment of the invention, the mitochondrial disorder preferably, but not exclusively, is a mitochondrial disorder with affected oxidative phosphorylation function. A preferred mitochondrial disorder with affected oxidative phosphorylation function is a disorder selected from the group consisting of: Myoclonic epilepsy; Myoclonic Epilepsy with Ragged Red Fibers (MERRF); Leber's Hereditary Optic Neuropathy (LHON); neuropathy, ataxia and retinitis pigmentosa (NARP); Mitochondrial Myopathy, Encephalopathy, Lactic acidosis, Stroke-like episodes (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); SURF1 Leigh syndrome; myopathy; mitochondrial myopathy; cardiomyopathy; and encephalomyopathy and isolated or combined oxidative phosphorylation disorders.

Mitochondrial diseases may be associated with specific mutations in nuclear DNA (nDNA) and/or mitochondrial DNA (mDNA). In a preferred embodiment of the invention, the mitochondrial disorder or disease or condition associated with mitochondrial dysfunction is therefore associated with one or several specific mutations in nuclear DNA and/or mitochondrial DNA. Non-limiting examples of such causative genes are MT-ND1 (mtDNA gene), NDUFS1 (nDNA gene), POLG (nDNA gene), MT-TL1 (mtDNA gene) and C10ORF2 (nDNA gene) (Niyazov et al, Mol. Syndromol (2016) 7 (3): 122-137). In a further preferred embodiment of the invention, the mitochondrial disorder is associated with a mutation in the MT-TL1 (mitochondrially encoded tRNA leucine 1) gene. More preferably, the mutation in the MT-TL1 gene is at least one of m.3243A>G, m.3271T>C and m.3251A>G. In a most preferred embodiment, the mitochondrial disorder is associated with a m.3242A>G mutation of the mitochondrial tRNA(Leu) gene.

In a preferred embodiment of the invention, the disease or condition associated with mitochondrial dysfunction preferably is a disease or condition selected from, but not exclusively, the group consisting of: Friedreich's Ataxia (FRDA); renal tubular acidosis; Parkinson's disease; Alzheimer's disease; amyotrophic lateral sclerosis (ALS); Huntington's disease; Barth syndrome (also known as 3-Methylglutaconic aciduria type II); macula degeneration, preferably age-related macula degeneration; developmental pervasive disorders; hearing loss, deafness; diabetes; ageing; adverse drug effects hampering (normal) mitochondrial function, including e.g. mitochondrial dysfunction caused by nucleoside analog reverse transcriptase inhibitors (NRTIs), certain antibiotics, statins and anti-epileptic drugs; and ischemia and reperfusion injury, preferably ischemic reperfusion injury after acute myocardial infarction (AMI), after stroke, including perinatal stroke, after hemorrhagic shock, after intestinal ischemia, after emergency coronary surgery for failed percutaneous transluminal coronary angioplasty (PCTA), after vascular surgery with blood vessel cross clamping (e.g. of aorta, leading to skeletal muscle ischemia), after pancreatitis after manipulation of pancreatic or bile duct (ERCP), and/or after organ transplantation.

"Treating" a disorder, disease or condition with the compounds, methods and doses/dosages discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total.

Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, using a dose/dosage as defined above.

An "effective amount" of a compound is an amount of a compound which, when administered to a subject, is sufficient to reduce or eliminate either one or more symptoms of a disease, or to retard the progression of one or more symptoms of a disease, or to reduce the severity of one or more symptoms of a disease, or to suppress the manifestation of a disease, or to suppress the manifestation of adverse symptoms of a disease. An effective amount can be given in one or more administrations.

The "effective amount" of that may be combined with the carrier materials to produce a single dosage form will vary depending upon the host to which the active ingredient is administered and the particular mode of administration. The unit dosage chosen is usually fabricated and administered to provide a defined final concentration of the compound in the blood as specified below.

The effective amount (i.e. the effective total daily dose), preferably for adults, is herein defined as a total daily dose of about 20 to 800 mg, or about 30 to 800 mg or about 30 to 700 mg, or about 20 to 700 mg or about 20 to 600 mg, or about 30 to 600 mg, or about 30 to 500 mg, about 30 to 450 mg or about 30 to 400 mg, or about 30 to 350 mg or about 30 to 300 mg or about 50 to 600 mg, or about 50 to 500 mg, or about 50 to 450 mg, or about 50 to 400 mg or about 50 to 300 mg, or about 50 to 250 mg, or about 100 to 250 mg or about 150 to 250 mg. In the most preferred embodiment, the effective amount is about 200 mg.

Alternatively, the effective amount of the compound, preferably for adults, preferably is administered per kg body weight. The total daily dose, preferably for adults, is therefore about 0.2 mg/kg to about 15 mg/kg, or about 0.3 mg/kg to about 15 mg/kg or about 0.4 mg/kg to about 15 mg/kg or about 0.5 mg/kg to about 14 mg/kg or about 0.3 mg/kg to about 14 mg/kg or about 0.3 mg/kg to about 13 mg/kg or about 0.5 mg/kg to about 13 mg/kg or about 0.5 mg/kg to about 11 mg/kg.

More preferably, the total daily dose is about 1.5 mg/kg to about 9 mg/kg or about 1.5 mg/kg to about 8 mg/kg or about 1.5 mg/kg to about 7 mg/kg or about 1.5 mg/kg to about 5 mg/kg or about 2 mg/kg to about 9 mg/kg or about 2 mg/kg to about 8 mg/kg or about 2 mg/kg to about 7 mg/kg or about 2 mg/kg to about 5 mg/kg or about 2 mg/kg to about 4 mg/kg, or more preferably about 2.5-3 mg/kg. In the most preferred embodiment, the total daily dose is about 3 mg/kg.

The total daily dose for children is preferably at most 200 mg. More preferably the total daily dose is about 5 to 200 mg, about 10 to 200 mg, about 20 to 200 mg about 30 to 200 mg about 40 to 200 mg, or about 50 to 200 mg. Preferably, the total daily dose for children is about 5 to 150 mg, about 10 to 150 mg, about 20 to 150 mg about 30 to 150 mg about 40 to 150 mg, or about 50 to 150 mg. More preferably, the total daily dose is about 5 to 100 mg, about 10 to 100 mg, about 20 to 100 mg about 30 to 100 mg about 40 to 100 mg, or about 50 to 100 mg. Even more preferably, the total daily dose is about 5 to 75 mg, about 10 to 75 mg, about 20 to 75 mg about 30 to 75 mg about 40 to 75 mg, or about 50 to 75 mg.

Alternatively, the total daily dose is administered per kg body weight as indicated above, wherein most preferably the total daily dose is about 2.5-3 mg/kg.

Preferably, the effective total daily dose does not cause any of the side effects as defined herein above.

It has been surprisingly been found that a low total daily dose of 200 mg is effective when administered. In particular, in vitro studies using primary fibroblasts isolated from patients with different mitochondrial disorders demonstrated an $EC_{50}$ of e.g. 182 nM (around 60 ng/ml) for a compound as defined herein and 16 nM (around 5.8 ng/ml) for its metabolite. At 200 mg as a total daily dose, applicants discovered that the average concentrations of the compound are a factor 3-5 above $EC_{50}$'s and average concentrations of its metabolite are a factor 10-20 above $EC_{50}$'s. Low levels of the administered compound as defined herein are thus effective for treatment, prevention or suppression of symptoms as defined herein.

Several readily measurable biomarkers are used to assess the metabolic state of patients with mitochondrial disorders. These markers can also be used as indicators of the efficacy of the therapy using the compounds and dose/dosage as defined herein, as the level of a marker is moved from the pathological value to the healthy value. In a preferred embodiment, the invention therefore pertains to a compound as defined herein above for use in treating, preventing, or suppressing symptoms associated with a mitochondrial disorder or with a disease or condition associated with mitochondrial dysfunction by administration of an effective dose as defined herein, wherein preferably a measurable biomarker is used to assess the efficacy of the therapy.

These biomarkers include, but are not limited to, one or more of the energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; amino acids, in particular alanine, citrulline and proline either in whole blood, plasma, cerebrospinal fluid, organic acids in body fluids, FGF21 in serum and skeletal muscle, phosphocreatine levels, NADH ($NADH+H^+$) or NADPH ($NADPH+H^+$) levels; NAD or NADP levels; ATP levels; anaerobic threshold; reduced coenzyme Q ($CoQ^{red}$) levels; oxidized coenzyme Q ($CoQ^{ox}$ levels; total coenzyme Q ($CoQ^{tot}$) levels; oxidized cytochrome C levels; reduced cytochrome C levels; oxidized cytochrome C/reduced cytochrome C ratio; acetoacetate levels, beta-hydroxy butyrate levels, acetoacetate/betahydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these biomarkers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, dominant optic atrophy, Leigh syndrome, SURF1, MERRF, MELAS, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, dominant optic atrophy, Leigh syndrome, SURF1, MERRF, MELAS, or KSS is improved to within one standard deviation of the average level in a healthy subject. Exercise intolerance can also be used as an indicator of the efficacy of a given therapy, where an improvement in exercise tolerance (i.e. a decrease in exercise intolerance) indicates efficacy of a given therapy.

Several metabolic biomarkers have already been used to evaluate efficacy of $CoQ_{10}$, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial OXPHOS. Dysfunction of the OXPHOS may lead to inadequate removal of lactate and pyruvate from the circulation and elevated lactate/pyruvate ratios are observed in mitochondrial cytopathies (see Scriver CR, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409 (2): 287-91 (1997); Honda et al., Leuk. Res. 24(6):461-8 (2000); Pilger et al., Free Radic. Res. 35(3):273-80 (2000); Kim et al., Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS ($^1$H-MRS) (Kaufmann et al., Neurology 62(8):1297-302 (2004)). Phosphorous MRS ($^{31}$P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V 02 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+$H^+$, NADPH+$H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, mt.3243A>G and mt.8344A>G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH (NADH+$H^+$) or NADPH (NADPH+$H^+$) can be measured by a variety of fluorescent, enzymatic, or electrochemical techniques, e.g., the electrochemical assay described in US2005/0067303.

Oxygen consumption ($vO_2$ or VO2), carbon dioxide output ($vCO_2$ or VCO2), and respiratory quotient (VCO2/VO2): $vO_2$ is usually measured either while resting (resting $vO_2$) or at maximal exercise intensity ($VO_2$ max). Optimally, both values will be measured. However, for severely disabled patients, measurement of v $O_2$ max may be impractical. Measurement of both forms of v $O_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt Cox), reduced cytochrome C levels (Cyt $C^{red}$), and the ratio of oxidized cytochrome C/reduced cytochrome C ratio (Cyt $C^{ox}$)/(Cyt $C^{red}$), can be measured by in vivo near infrared spectroscopy. See, e. g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Pina et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, beta-hydroxy butyrate levels, acetoacetate/betahydroxy butyrate ratio, 8-hydroxy-2'-deoxyguanosine (8-OHdG) levels, 4-hydroxynonenal levels, malondialdehyde levels, oxidized glutathione/reduced glutathione ratio, isoprostanes levels, prostaglandins, NO2-fatty acids levels, lyso-phosphatidic acids levels, lyso-shingolipids levels and levels of reactive oxygen species are known in the art and can be used to evaluate efficacy of the compounds, dose/dosages and methods of the invention. (For the purposes of the invention, modulation, normalization, or enhancement of energy biomarkers includes modulation, normalization, or enhancement of anaerobic threshold).

Table 2, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 2

| Site of dysfunction | Biochemical event | Measurable Energy Biomarker | Physical Effect |
|---|---|---|---|
| OXPHOS | ↑ NADH | Δ lactate, Δ lactate:pyruvate ratio, Δ acetoacetate:β-hydroxybutyrate ratio | Metabolic dyscrasia & fatigue |
| OXPHOS | ↑ NADH | Amino acids | Metabolic dyscrasia & fatigue |
| OXPHOS | ↑ NADH | Organic acids | Metabolic dyscrasia & fatigue |
| OXPHOS | ↑ NADH | FGF21 | Metabolic dyscrasia & fatigue |
| OXPHOS | ↓ $H^+$ gradient | Δ ATP | Organ dependent dysfunction |
| OXPHOS | ↓ Electron flux | Δ $VO_2$, RQ, BMR, ΔT, AT, pH | Metabolic dyscrasia & fatigue |
| Mitochondria & cytosol | ↓ ATP, ↓ $VO_2$ | Δ Work, ΔHR (CO) | Exercise intolerance |
| Mitochondria & cytosol | ↓ ATP | Δ PCr | Exercise intolerance |
| Respiratory Chain | ↓ Cyt $C^{Ox/Red}$ | Δ ~700-900 nm (NIR spectroscopy) | Exercise intolerance |
| Intermediary metabolism | ↓ Catabolism | Δ $C^{14}$-labeled substrates | Metabolic dyscrasia & fatigue |
| Respiratory Chain | ↓ Electron flux | Δ Mixed venous $VO_2$ | Metabolic dyscrasia & fatigue |
| Mitochondria & cytosol | ↑ Oxidative stress | Δ Tocopherol & Tocotrienols, CoQ10 docosahexanoic acid | Uncertain |
| Mitochondria & cytosol | ↑ Oxidative stress | Δ $Glutathione^{red}$ | Uncertain |
| Mitochondria & cytosol | Nucleic acid oxidation | Δ 8-hydroxy 2-deoxy guanosine | Uncertain |
| Mitochondria & cytosol | Lipid oxidation | Δ Isoprostane(s), eicasanoids | Uncertain |
| Cell membranes | Lipid oxidation | Δ Ethane (breath) | Uncertain |
| Cell membranes | Lipid oxidation | Δ Malondialdehyde | Uncertain |

In a further preferred embodiment, the biomarker is selected from the group consisting of FGF21, GDF15, PRDX1 and oxidized glutathione/reduced glutathione ratio. Fibroblast growth factor 21 (FGF-21) is a growth factor with regulatory roles in lipid metabolism and the starvation response. Serum FGF21 (S-FGF21) is a specific biomarker for muscle-manifesting defects of mitochondrial translation, including mitochondrial transfer-RNA mutations and primary and secondary mtDNA deletions, the most common causes of mitochondrial disease (Lehtonen J M et al, *Neurology* (2016) 87 (22): 2290-2299). GDF-15 is a serum quantitative biomarker for the diagnosis of mitochondrial diseases in children. GDF-15 is produced by skeletal muscle cells in response to mitochondrial dysfunction and its levels correlate in vitro with FGF-21 levels (Montero R et al, PLOS One (2016) 11 (2): e0148709).

Peroxiredoxin-1 (PRDX1) acts as a hydrogen peroxide scavenger and can therefore function as a biomarker for oxidative stress. Similarly, the ratio oxidized glutathione/reduced glutathione may function as a biomarker for oxidative stress.

As specified herein above, the biomarker may be detected in any body fluid or tissue and the skilled person straightforwardly understands the preferred body fluid or tissue for detection of the biomarker as specified herein. In a preferred embodiment, the biomarker is detected ex vivo, preferably in a body fluid obtained from the subject as defined herein. The body fluid may for example be selected from the group consisting of whole blood, plasma, serum, urine, saliva, cerebrospinal fluid and cerebral ventricular fluid. The tissue may for example be selected from skeletal muscle or skin in the case of cultured skin fibroblasts. In a preferred embodiment, the biomarker is measured ex vivo in serum. Treatment of a subject afflicted by a mitochondrial disease in accordance with the methods (and hence dose/dosage) of the invention may result in the inducement of a reduction or alleviation of symptoms in the subject, e.g. to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one energy biomarker or any combination of the energy biomarkers described herein provide conveniently measurable benchmarks by which to gauge the effectiveness of treatment or suppressive therapy. In particular, the biomarker(s) as defined herein can be used to assess the efficacy of the compound when administrated at the effective total daily dose as described herein.

In addition, evaluation of the biomarker(s) as defined herein may result in the adjustment of the total daily dose. As a non-limiting example, when a biomarker indicates an absence or a limited effect of the compound when administrated at a specific dosage (e.g. the effect is significantly below the established threshold for the biomarker), the dosage may be increased. However, it now has been shown that surprisingly a total daily dose of 800 mg or more may cause side effects. When adjusting the dosage to increase the effective amount, preferably the total daily dose should therefore preferably remain below 800 mg, 750 mg, 700 mg, 650 mg, 600 mg, 550 mg or 500 mg. A total daily dose of 400 mg or less is particularly well tolerated.

As a second (non-limiting) example, when the biomarker(s) indicate(s) that the total daily dose is very effective (e.g. significantly above the established threshold for the biomarker), the daily dose may be reduced. However, it has now been surprisingly shown that a low total daily dose of 200 mg is effective. Therefore the total daily dose preferably should be at least 20 mg, 50 mg, 100 mg, 150 mg, 170 mg, 180 mg, 190 mg or 200 mg.

Additionally, other energy biomarkers are known to those skilled in the art and can be monitored to evaluate the efficacy of treatment or suppressive therapy. Mitochondrial dysfunction is a common cause of inherited multisystem disease that often involves the nervous system. Despite major advances in our understanding of the pathophysiology of mitochondrial diseases, clinical management of these conditions remains largely supportive.

In a preferred embodiment, the efficacy of treatment or suppressive therapy with the treatment methods of the invention can be determined using one or more of the outcome measures of the toolbox as listed in Table 1 of Koene et al., (Koene et al, 2013, Dev, Med. Child Neurol. 55:698-706), more preferably the efficacy is determined using one or more of the outcome measures of the "Common core set" in Table 1 of Koene et al (2013, supra).

In yet another aspect the invention relates to the cosmetic use of the compounds of the invention by administration of an effective total daily dose. The effective total daily dose is defined herein above. Preferably, the effective total daily dose does not cause any side effects as defined herein above. More preferably, the effective total daily dose is in the range of about 10 to 1000 mg.

The methods as defined herein may thus revive the skin of a treated individual, particularly in individuals with aged skin, either due to aging or due to excessive exposure to sun. Both conditions are related to the production of free radicals in skin. By at least one of induction of mitochondrial filamentation, prevention or reduction of mitochondrial fragmentation, and increased expression of OXPHOS enzymes in a cell of said individual it is possible to lower the action of free radicals in the skin and at least delay further aging in the skin. As such, one can also use the methods of the invention as prophylactic, i.e. to at least reduce free radicals that would be capable to act on the skin, if left untreated. Thus preferably in this aspect of the invention, administration of an effective amount of the compounds results in the effect of which includes one or more of induction of mitochondrial filamentation, prevention or reduction of mitochondrial fragmentation, and increased expression of OXPHOS enzymes. Preferred compounds having these effects are indicated herein above.

The methods of the invention can also be used in research applications, such as in vivo experiments in order to modulate one or more energy biomarkers in organisms, e.g. primates. Such research applications can include, but are not limited to, the effects of other agents on the metabolic state of the organism in the presence/absence of one or more compounds defined herein.

A compound for use as defined herein (i.e. for use in treating, preventing, or suppressing symptoms associated with a mitochondrial disorder or with a disease or condition associated with mitochondrial dysfunction by administration of an effective total daily dose) may be administered as a composition.

The compositions comprising the compounds as described above, can be prepared as a medicinal or cosmetic preparation or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube (referred to as enteral administration). A "dietary supplement" shall mean a product that is intended to supplement the human diet and is typically provided in the form of a pill, capsule, and tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food, including, but not limited to, food bars, beverages, powders, cereals, cooked foods, food additives and candies; or other functional foods designed to promote cerebral health or to prevent or halt the progression of a neurodegenerative disease involving mitochondrial dysfunction.

The subject compositions thus may be compounded with other physiologically acceptable materials which can be ingested including, but not limited to, foods. In addition or alternatively, the compositions for use as described herein may be administered orally in combination with (the separate) administration of food.

The compositions may be administered alone or in combination with other pharmaceutical or cosmetic agents and can be combined with a physiologically acceptable carrier thereof. In particular, the compounds described herein can be formulated as pharmaceutical or cosmetic compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-P-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003), $21^{st}$ edition (2005) and $22^{nd}$ edition (2012), incorporated herein by reference.

Pharmaceutical or cosmetic compositions containing the compounds for use according to the invention may be in any form suitable for the intended method of administration, including, for example, a solution, a suspension, or an emulsion. In a preferred embodiment, the compound is administered in a solid form or in a liquid form.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water or saline. Such compositions may also comprise adjuvants, such as wetting agents, emulsifying and suspending agents, cyclodextrins, and sweetening, flavoring, and perfuming agents.

Liquid carriers are typically used in preparing solutions, suspensions, and emulsions. In a preferred embodiment, liquid carriers/liquid dosage forms contemplated for use in the practice of the present invention include, for example, water, saline, pharmaceutically acceptable organic solvent(s), pharmaceutically acceptable oils or fats, and the like, as well as mixtures of two or more thereof. In a preferred embodiment, the compound for use as defined herein is admixed with an aqueous solution prior to administration, The aqueous solution should be suitable for administration and such aqueous solutions are well known in the art. It is further known in the art that the suitability of an aqueous solution for administration may be dependent on the route of administration.

In a preferred embodiment, the aqueous solution is an isotonic aqueous solution. The isotonic aqueous solution preferably is almost (or completely) isotonic to blood plasma. In an even more preferred embodiment, the isotonic aqueous solution is saline. The liquid carrier may contain other suitable pharmaceutically acceptable additives such as solubilizers, emulsifiers, nutrients, buffers, preservatives, suspending agents, thickening agents, viscosity regulators, stabilizers, flavorants and the like. Preferred flavorants are sweeteners, such as monosaccharides and/or disaccharides. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like.

For parenteral administration, the carrier can also be an oily ester such as ethyl oleate, isopropyl myristate, and the like. Compositions for use in the present invention may also be in the form of microparticles, microcapsules, liposomal encapsulates, and the like, as well as combinations of any two or more thereof.

Time-release, sustained release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound as defined herein, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N. Y., p. 33 et seq (1976).

A pharmaceutical or cosmetic composition can comprise a unit dose formulation, where the unit dose is a dose sufficient to have a therapeutic or suppressive effect of a disorder or condition as defined herein, and/or an amount effective to modulate, normalize, or enhance an energy biomarker. The unit dose may be sufficient as a single dose to have a therapeutic or suppressive effect of a disorder or condition as defined herein and/or an amount effective to modulate, normalize, or enhance an energy biomarker. Alternatively, the unit dose may be a dose administered periodically in a course of treatment or suppression of a disorder or condition as defined herein, and/or to modulate, normalize, or enhance an energy biomarker. During the course of the treatment, the concentration of the subject compositions may be monitored to insure that the desired level is maintained.

In a preferred embodiment the invention pertains to a compound as defined herein for use in treating, preventing, or suppressing symptoms associated with a mitochondrial disorder or with a disease or condition associated with mitochondrial dysfunction by administration of an effective total daily dose, and wherein preferably the compound reaches a blood steady state level within 5 days. More preferably steady state levels are reached within 4 days, even more preferably within 3 days and most preferably steady state levels are reached within 2 days after the first administration.

Steady state is herein understood that the overall intake of a compound as defined above is (roughly) in dynamic equilibrium with its elimination. During steady state, the plasma levels of the compound preferably maintained within the effective therapeutic range. Put differently, the levels of the compound in the blood are maintained between the minimum therapeutically effective concentration and the maximum therapeutically effective concentration. Below the minimum concentration, the compound does not have sufficient therapeutic effect to be considered efficacious. Above the maximum concentration, side effects increase eventually leading to toxicity.

To maintain an effective therapeutic range during treatment, the average plasma concentrations (Cav) of the compound as defined herein is maintained between about 30 ng/ml to about 5000 ng/ml, or between about 30 ng/ml to about 4000 ng/ml, or between about 30 ng/ml to about 3000 ng/ml, or between about 30 ng/ml to about 2000 ng/ml, or about 30 ng/ml to about 1000 ng/ml, or between about 50 ng/ml to about 5000 ng/ml, or between about 100 ng/ml to about 5000 ng/ml, or between about 50 ng/ml to about 4000 ng/ml, or between about 50 ng/ml to about 3000 ng/ml, or between about 50 ng/ml to about 2000 ng/ml, or between about 50 ng/ml to about 1000 ng/ml. In a more preferred embodiment, the average plasma concentration of the compound is maintained between about 50 ng/ml-500 ng/ml or 100 ng/ml-500 ng/ml.

The average plasma concentrations may be determined using any conventional method known in the art. However in a preferred embodiment, the plasma concentrations are determined by extracting the compound as defined herein from human plasma by protein precipitation, followed by Liquid Chromatography-Tandem Mass Spectrometry (LC-MS/MS). The concentration of the compound may subsequently be determined using calibration standards.

The compound as defined herein may be metabolized and instead of, or in addition to the non-metabolized compound, the effective therapeutic range of the metabolized compound may be maintained during treatment. In a preferred embodiment of the invention, the average plasma concentrations ($C_{av}$) of the metabolized compound is maintained between about 20 ng/ml to about 1000 ng/ml, or between about 20 ng/ml to about 800 ng/ml, or between about 20 ng/ml to about 600 ng/ml, or between about 20 ng/ml to about 400 ng/ml, or about 20 ng/ml to about 200 ng/ml, or between about 30 ng/ml to about 1000 ng/ml, or between about 50 ng/ml to about 1000 ng/ml, or between about 30 ng/ml to about 800 ng/ml, or between about 30 ng/ml to about 600 ng/ml, or between about 30 ng/ml to about 400 ng/ml, or between about 30 ng/ml to about 200 ng/ml. In a more preferred embodiment, the average plasma concentration of the compound is maintained between about 40 ng/ml-500 ng/ml or 50 ng/ml-200 ng/ml.

During or after administration of the compound as defined herein, the maximum plasma concentrations ($C_{max}$) remain below about 5000 ng/ml or below about 4000 ng/ml or below about 3000 ng/ml or below about 2000 ng/ml or below about 1000 ng/ml. In the most preferred embodiment, the maximum plasma concentrations remain below about 500 ng/ml.

Similarly, the maximum plasma concentrations of the metabolized compound remain below about 1000 ng/ml, or below about 800 ng/ml or below about 600 ng/ml or below about 400 ng/ml. In the most preferred embodiment, the maximum plasma concentrations of the metabolized compound remain below about 250 ng/ml To maintain an effective range during treatment, the compound may be administered once a day, or once every two, three, four or five days. However preferably, the compound may be administered at least once a day. Hence in a preferred embodiment, the invention pertains to a compound as defined herein above, for use in treating, preventing, or suppressing symptoms associated with a mitochondrial disorder or with a disease or condition associated with mitochondrial dysfunction by administration of an effective total daily dose, wherein the effective dose is defined herein above. The total daily dose may be administered as a single daily dose. Alternatively, the compound is administered at least twice daily. Hence, the compound as defined herein may be administered once, twice, three, four or five times a day. As such, the total daily dose may be divided over the several doses (units) resulting in the administration of the total daily dose as defined herein. In a preferred embodiment, the compound is administered twice daily. It is further understood that the terms "twice daily", "bid" and "bis in die" can be used interchangeable herein.

In a preferred embodiment, the total daily dose is divided over several doses per day. These separate doses may differ in amount. For example for each total daily dose, the first dose may have a larger amount of the compound than the second dose or vice versa. However preferably, the compound is administered in similar or equal doses. Therefore in a most preferred embodiment, the compound is administered twice daily in two similar or equal doses.

In a further preferred embodiment of the invention, the total daily dose of the compound as defined herein above is administered in at least two separate doses. The interval between the administration of the at least two separate doses is at least about 0.5, 1, 2, 3, 4, 5, 6, 7, 8, 9, 10, 11 or 12 hours, preferably the interval between the at least two separate doses is at least about 4, 5, 6, 7, 8, 9, 10, 11 or 12 hours and more preferably the interval between the at least two separate doses is at least about 8, 9, 10, 11 or 12 hours.

The composition can be administered in an effective total daily dose as defined herein, either as a prophylaxis or treatment, to a patient in any of a number of methods. In particular, the method of administration can vary based on the individual subject, the condition or the stage of disease, and other factors evident to one skilled in the art.

The compounds for a use as defined herein may be administered enterally, orally, parenterally, sublingually, by inhalation (e. g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e. g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques.

The compounds are mixed with pharmaceutically acceptable carriers, adjuvants, and vehicles appropriate for the desired route of administration. Oral administration is a preferred route of administration, and formulations suitable for oral administration are preferred formulations. Alternatively, the compounds may be administered by supplementation via gastric or percutaneous tubes.

Hence, in a preferred embodiment the invention pertains to a compound as defined herein above, for use in treating, preventing, or suppressing symptoms associated with a mitochondrial disorder or with a disease or condition associated with mitochondrial dysfunction by administration of an effective total daily dose, wherein compound is administered orally.

The oral route is the preferred means of administration and (at least for adults) preferably the dosage form used is a solid oral dosage form. The class of solid oral dosage forms consists primarily of tablets and capsules, although other forms are known in the art and can be equally suitable. When used as a solid oral dosage form, the compound as defined herein may e.g. be administered in the form of an immediate release tablet (or a capsule and the like) or a sustained release tablet (or a capsule and the like). Any suitable immediate release or sustained release solid dosage forms can be used in the context of the invention as will be evident for the skilled person.

The compounds described for use as described herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

While the compounds for use as described herein can be administered as the sole active pharmaceutical (or cosmetic) agent, they can also be used in combination with one or more other agents used in the treatment or suppression of disorders. Representative agents useful in combination with the compounds of the invention for the treating, preventing, or suppressing symptoms associated with a mitochondrial disorder or with a disease or condition associated with mitochondrial dysfunction include, but are not limited to, Coenzyme Q, vitamin E, idebenone, MitoQ, EPI-743, vitamin K and analogues thereof, naphtoquinones and derivatives thereof, other vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

In a preferred embodiment, the subject to be treated does not have a concomitant medication that may increase the plasma concentrations of the compound as defined herein. Preferably, the subject to be treated does not have a concomitant medication that is known to inhibit at least one member of the cytochrome p450 enzyme superfamily (CYP). Preferably, the subject to be treated does not have a concomitant medication that is known to inhibit a member of the CYP family selected from the group consisting of CYP1, CYP2, CYP3, CYP4, CYP5, CYP7, CYP8, CYP11, CYP17, CYP19, CYP20, CYP21, CYP24, CYP26, CYP27, CYP39, CYP46, and CYP51. More preferably, the subject to be treated does not have a concomitant medication that is known to inhibit a member of the CYP3 family (CYP3A4, CYP3A5, CYP3A7 and CYP3A43), and most preferably the subject to be treated does not have a concomitant medication that is known to inhibit CYP3A4.

In a further preferred embodiment, the subject to be treated does not have a concomitant medication that is known to inhibit a member of the super family of ATP-binding cassette (ABC) transporters. More specifically, the subject to be treated does not have a concomitant medication that is known to inhibit a member of the subfamily selected from the group consisting of ABC1, MDR/TAP, MRP, ALD, OABP, GCN20 and White. More preferably, the subject to be treated does not have a concomitant medication that is known to inhibit a member of the MDR/TAP subfamily and most preferably the subject to be treated does not have a concomitant medication that is known to inhibit PgP (P-glycoprotein 1).

Hence in the most preferred embodiment, the compound for use as defined herein is preferably not be used in combination with an agent that is known to inhibit at least one of CYP3A4 and PgP. Hence in the most preferred embodiment, the subject to be treated does not have a concomitant medication that is known to inhibit CYP3A4 and/or PgP.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

A. Example of an ECG adapted on the Global Superimposed Median Beat (GSMB). B. T wave symmetry index was computed by modeling the T wave in two independent half-Gaussian curves. The standard deviations of these functions ($\sigma 1$ and $\sigma 2$) and indicators of the ascending/descending speed.

Figure 4A:
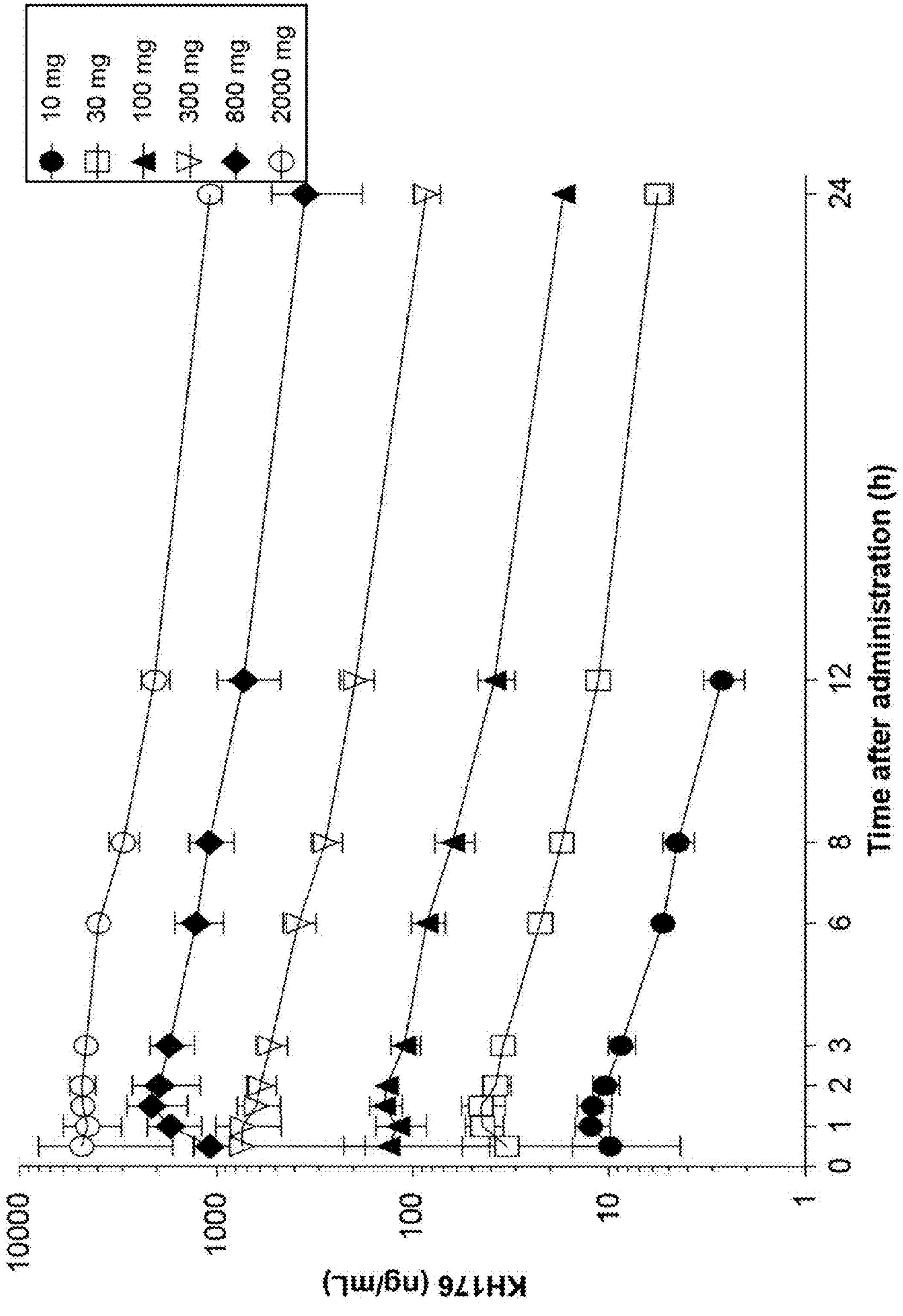
Figure 4B:
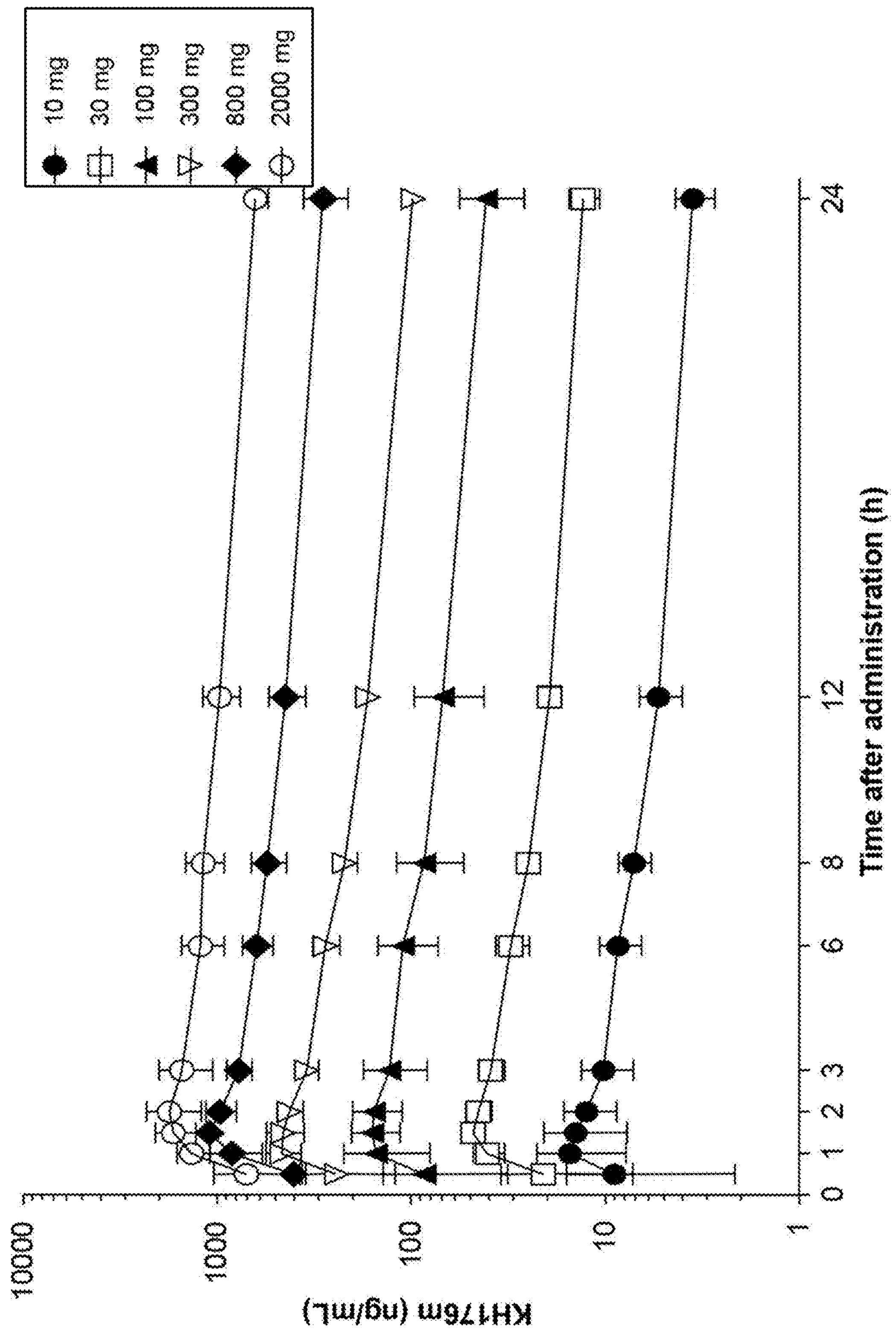
Figure 4C:
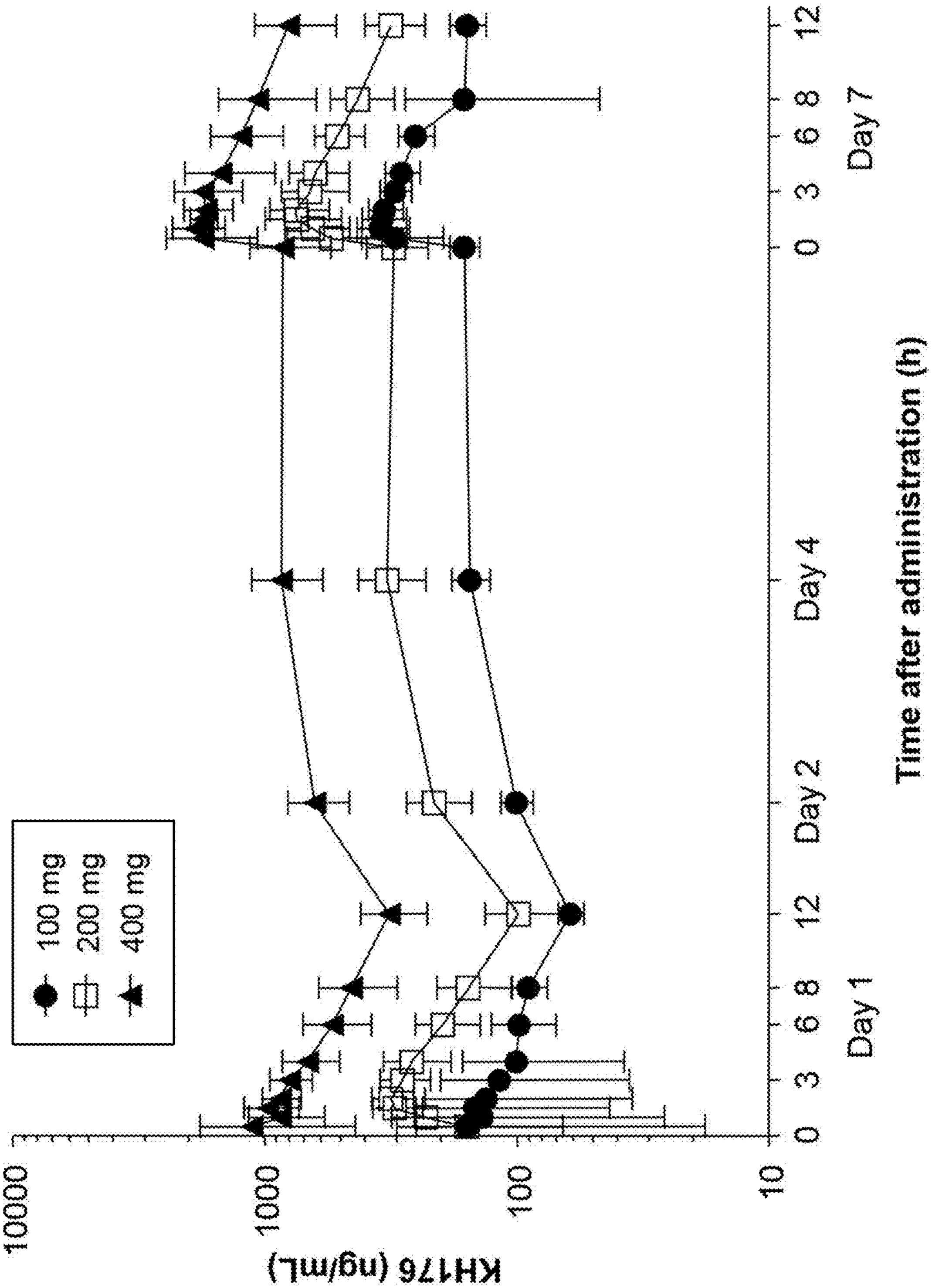

FIGS. 4A-4D. Mean plasma concentrations of KH176 and its metabolite KH176m after single and multiple dose administration to healthy subjects. FIG. 4A. Plasma-concentration/time curve of KH176 for the SAD study (fasted state), loglinear scale. FIG. 4B. Plasma-concentration/time curve of KH176m for the SAD study (fasted state), loglinear scale. FIG. 4C. Plasma-concentration/time curve of KH176 for the MAD study, loglinear scale and FIG. 4D. Plasma-concentration/time curve of KH176m for the MAD study, loglinear scale.

Figure 5A:
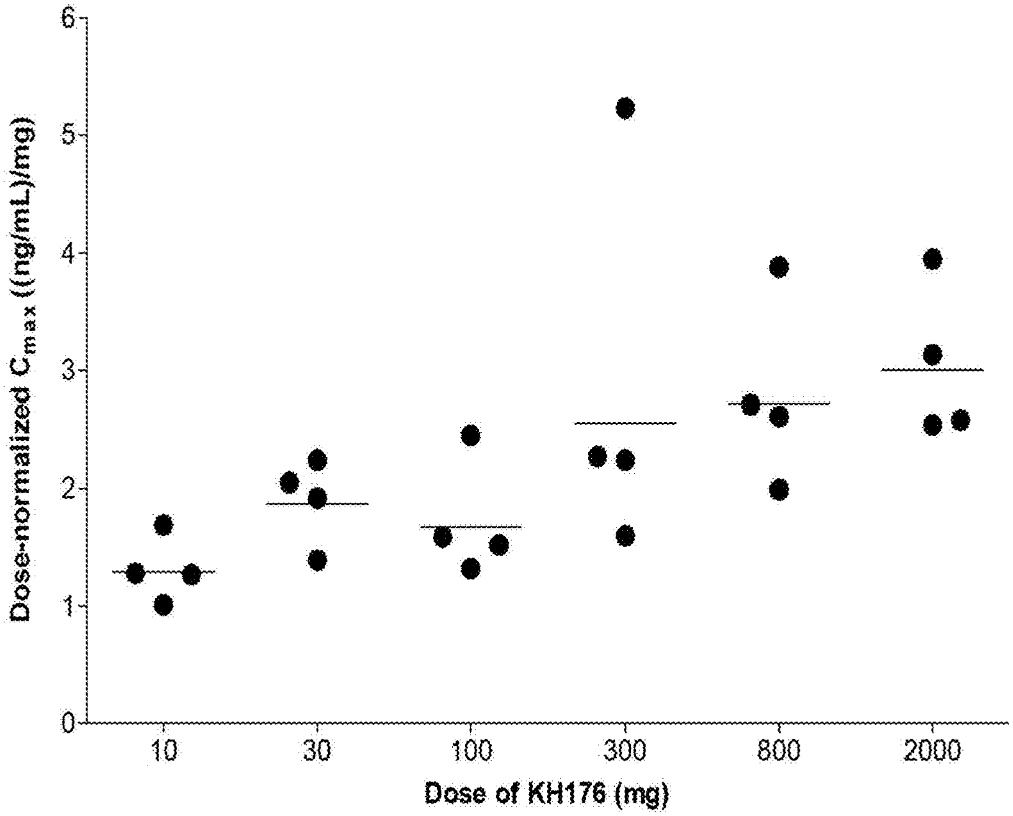
Figure 5B:
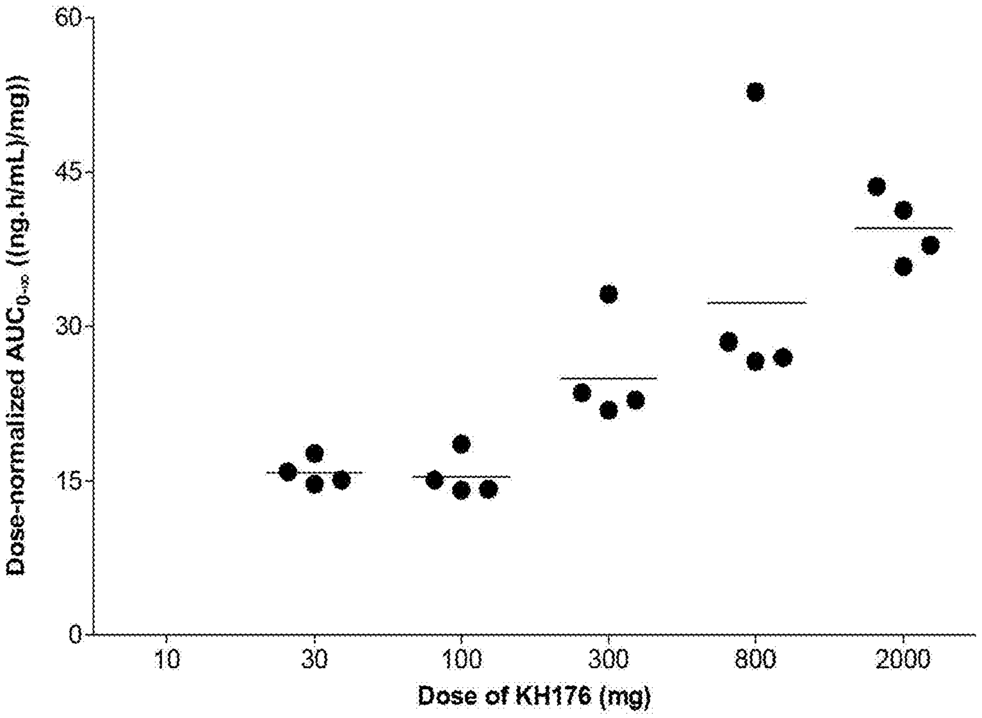
Figure 5C:
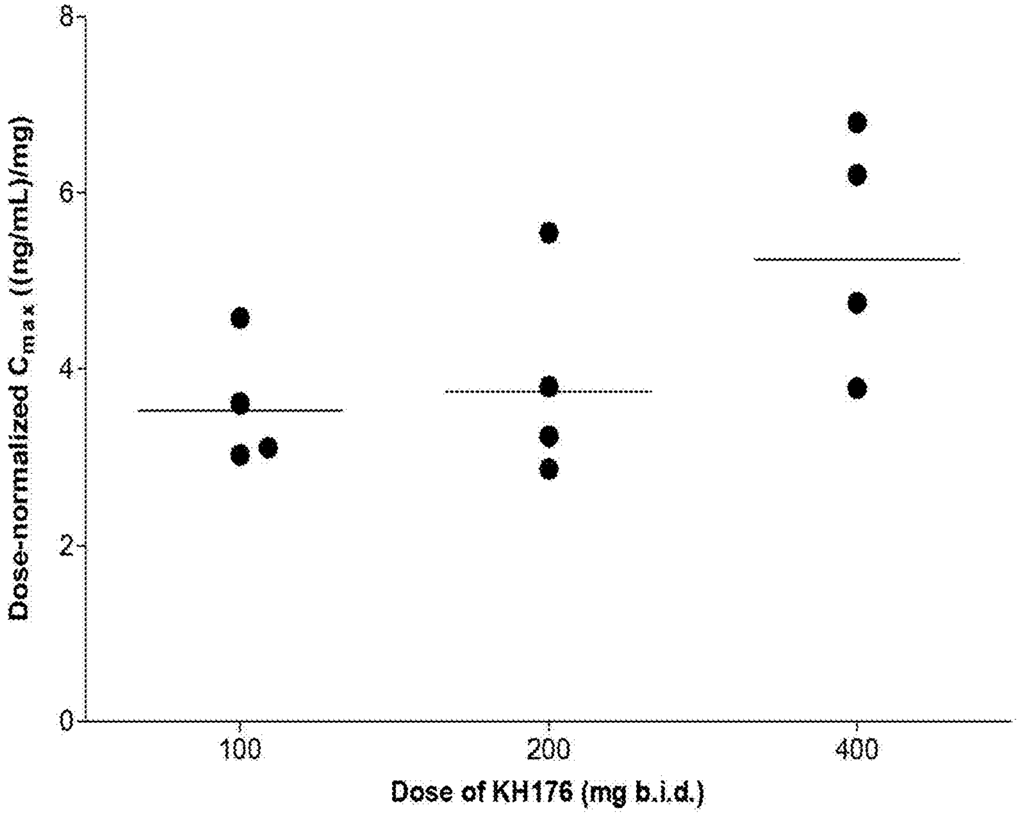
Figure 5D:
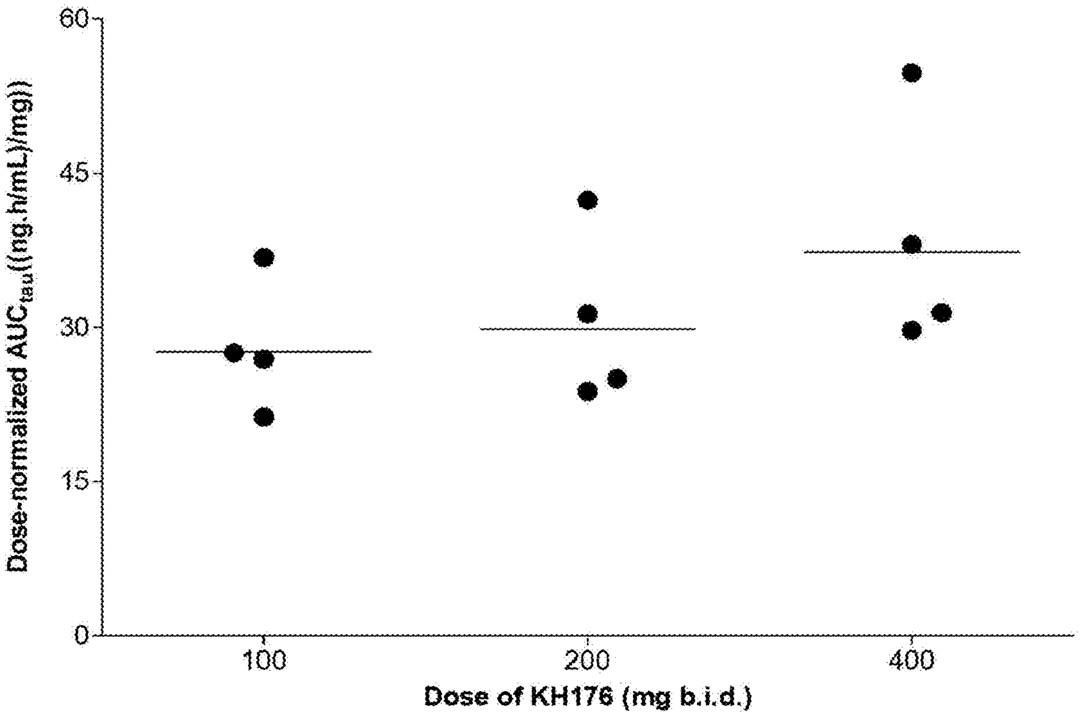

FIGS. 5A-5D. Dose-normalized individual values for Cmax and AUC0-inf of KH176 for the SAD and the MAD study. FIG. 5A. Dose normalized Cmax for the SAD study, the horizontal lines depict the geometric mean value. FIG. 5B. Dose normalized AUC0-inf for the SAD study, the horizontal lines depict the geometric mean value. FIG. 5C. Dose normalized Cmax for the MAD study, the horizontal lines depict the geometric mean value and FIG. 5D. Dose normalized AUC0-inf for the MAD study, the horizontal lines depict the geometric mean value.

Figure 6A:
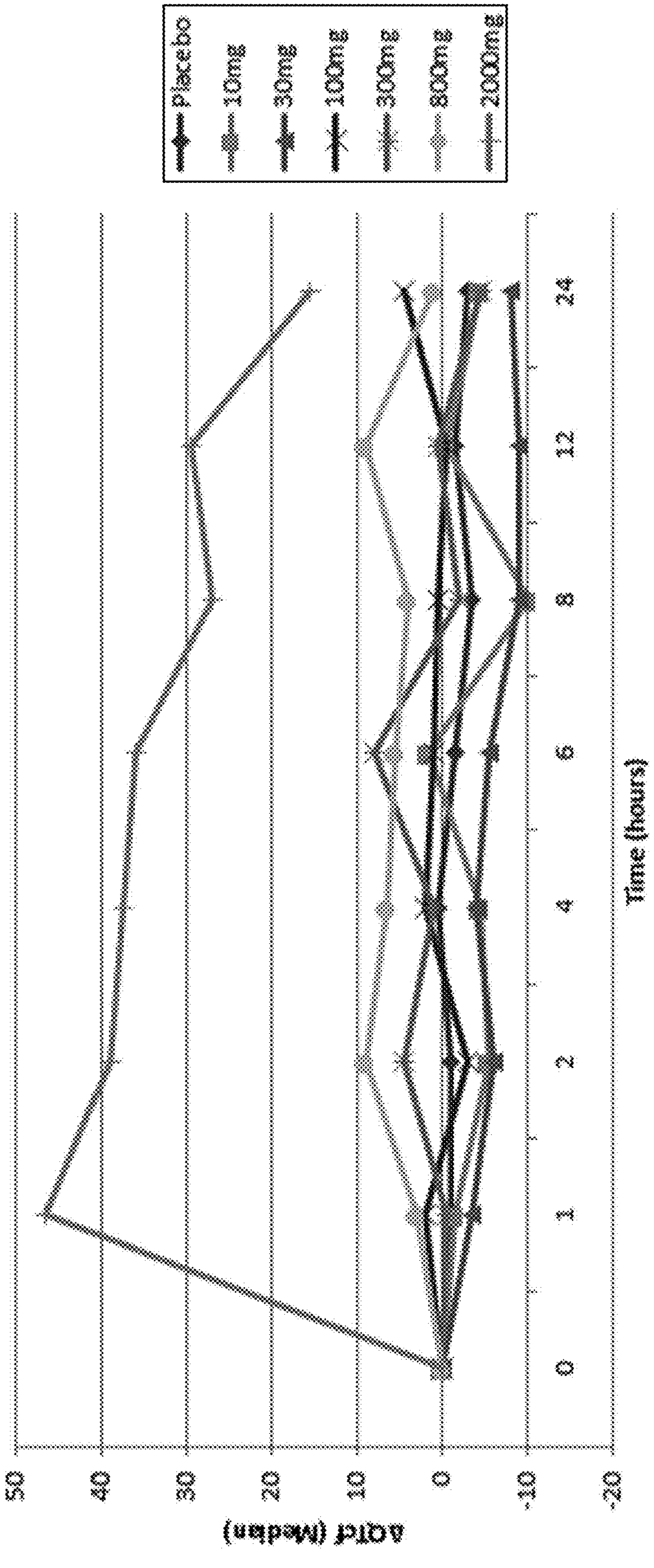
Figure 6B:
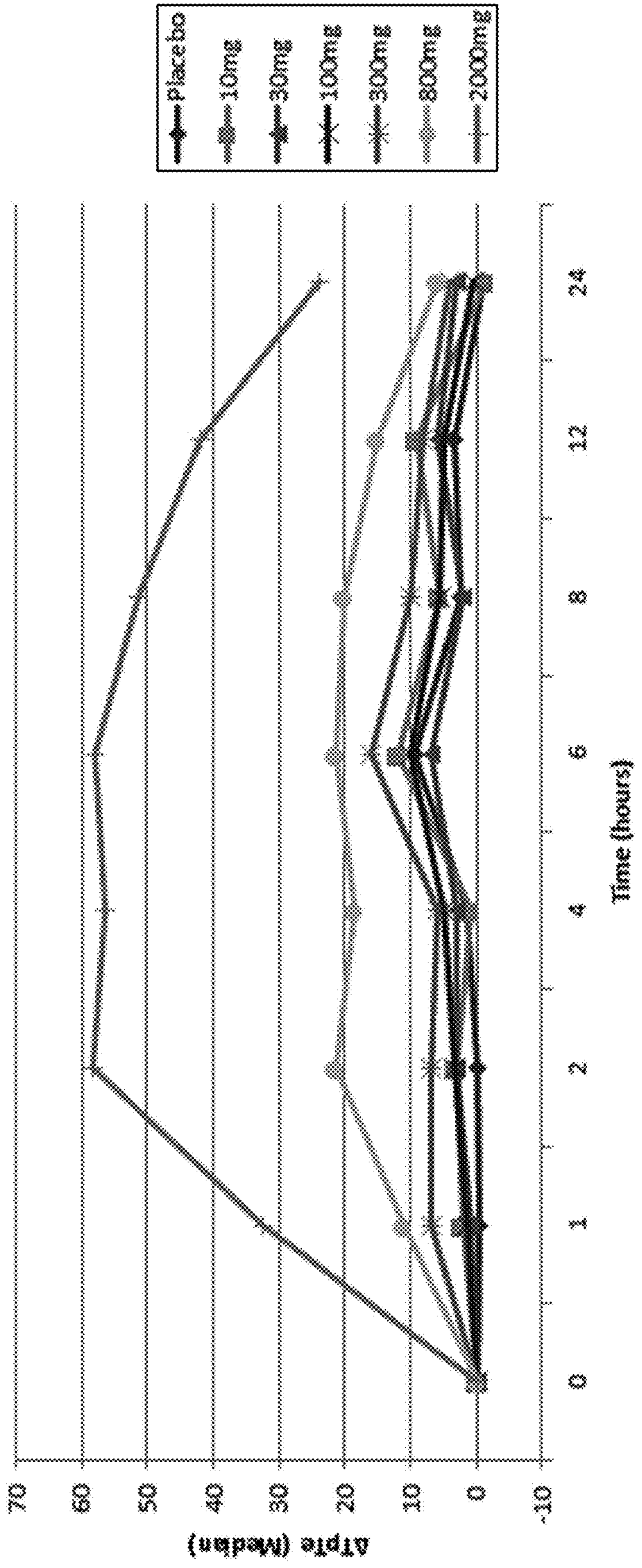
Figure 6C:
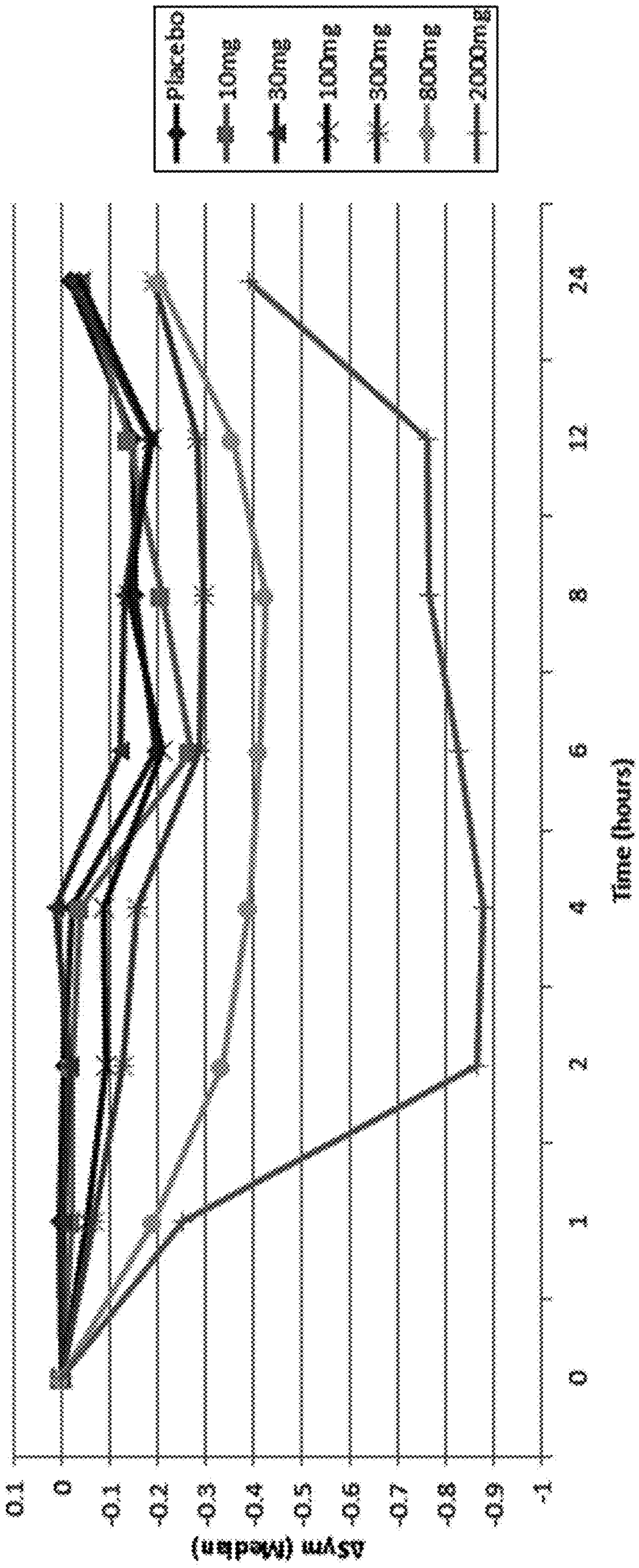
Figure 6D:
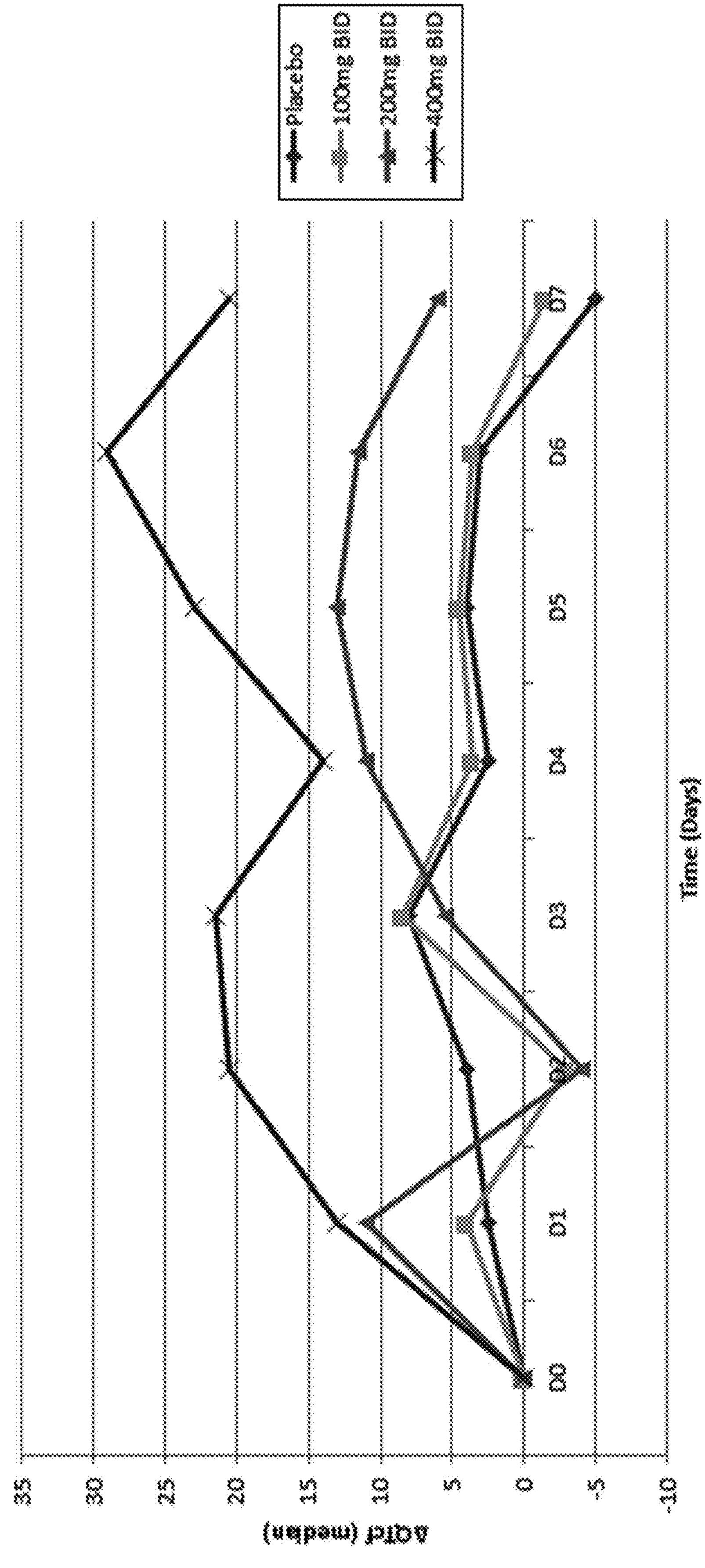
Figure 6E:
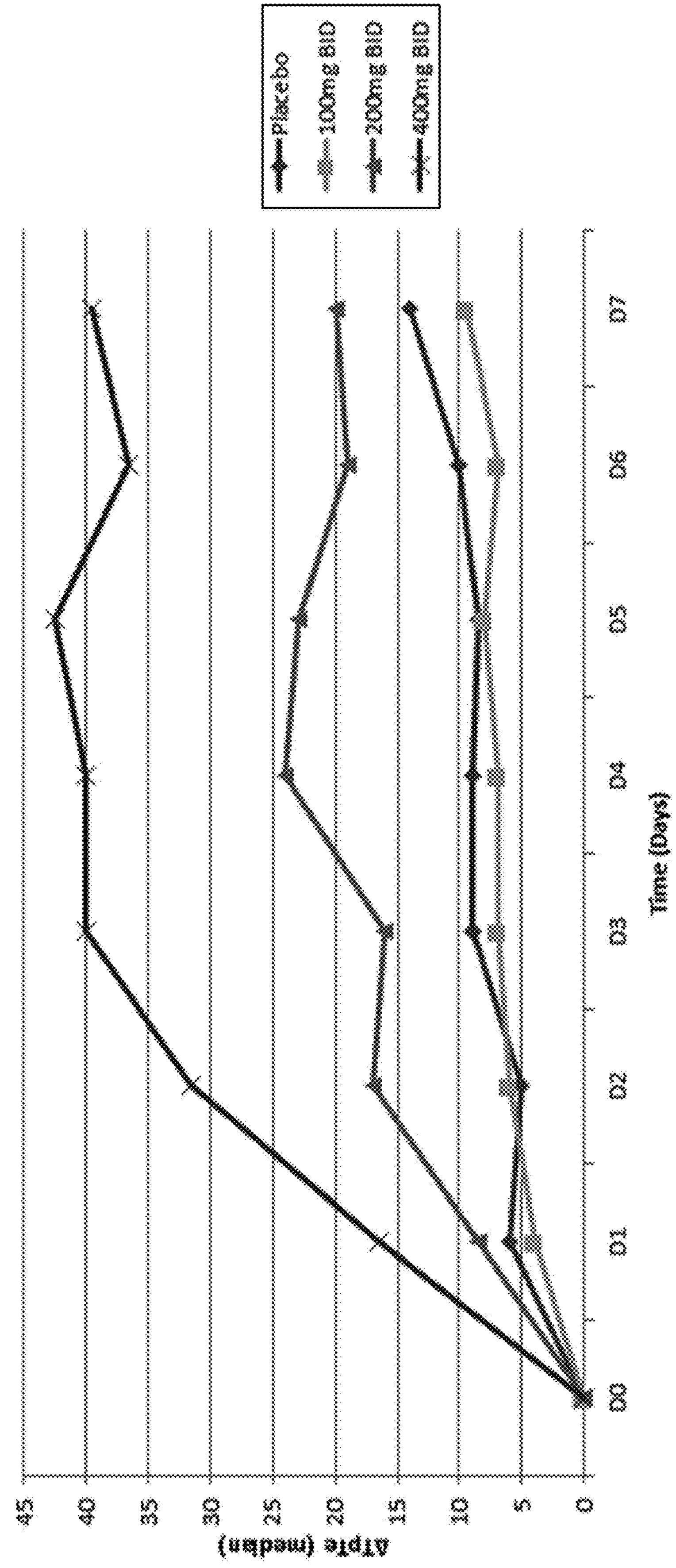
Figure 6F:
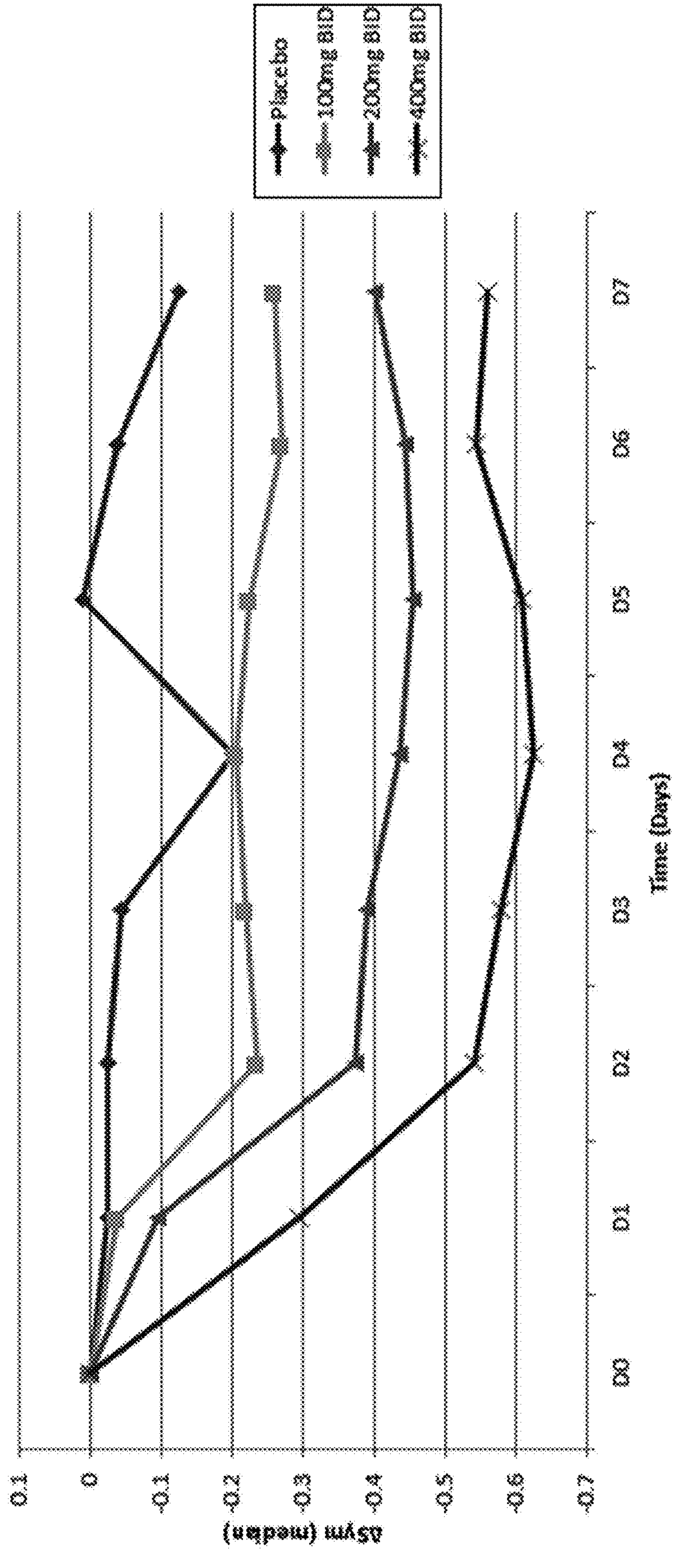

FIGS. 6A-6F. Posthoc ECG assessment results. FIG. 6A. Change in QTcF (median increase from baseline; SAD study). FIG. 6B. Change in TpTe (median increase from baseline; SAD study). FIG. 6C. Change in the T-wave symmetry index (median increase from baseline; SAD study). FIG. 6D. Change in QTcF (median increase from baseline; MAD study). FIG. 6E. Change in TpTe (median increase from baseline; MAD study). FIG. 6F. Change in the T-wave symmetry index (median increase from baseline; MAD study).

Figure 7:
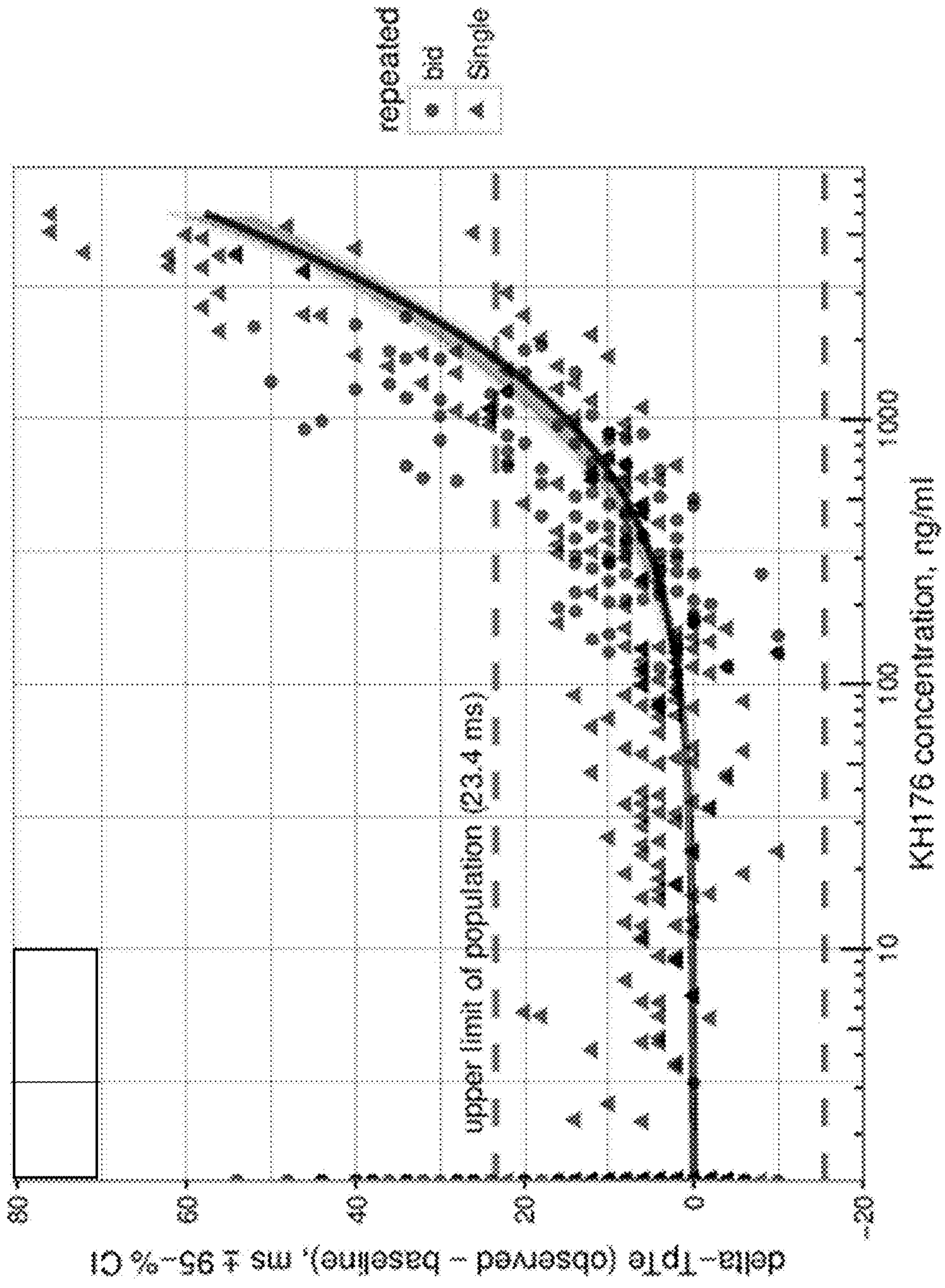

FIG. 7. Exposure-response analysis of KH176 plasma concentrations and a change from baseline for ECG derived TpTe intervals. The upper limit of normal (23.4 ms) is derived from the 95% confidence interval of the predose values. In healthy subjects a dose of 100 mg BID resulted in maximum concentrations ranging from 303-458 ng/mL.

Figure 8:
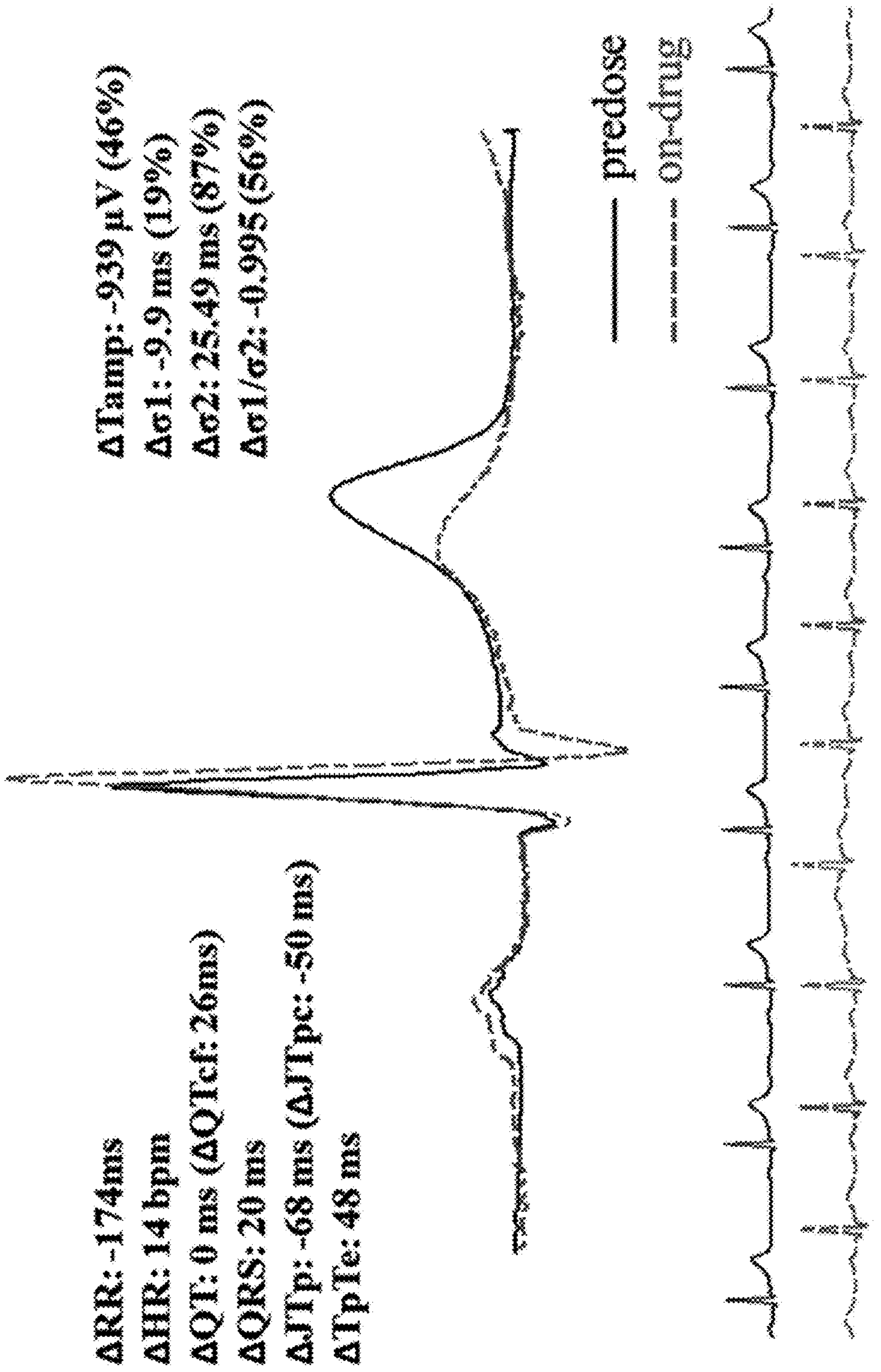

FIG. 8. Representative example of the changes in the QRS interval, QT-time and the T-wave morphology in an individual in the 2000 mg group.

EXAMPLES

Methods

In Vitro: Oxidative Stress-Induced Cell Death

Figure 1:
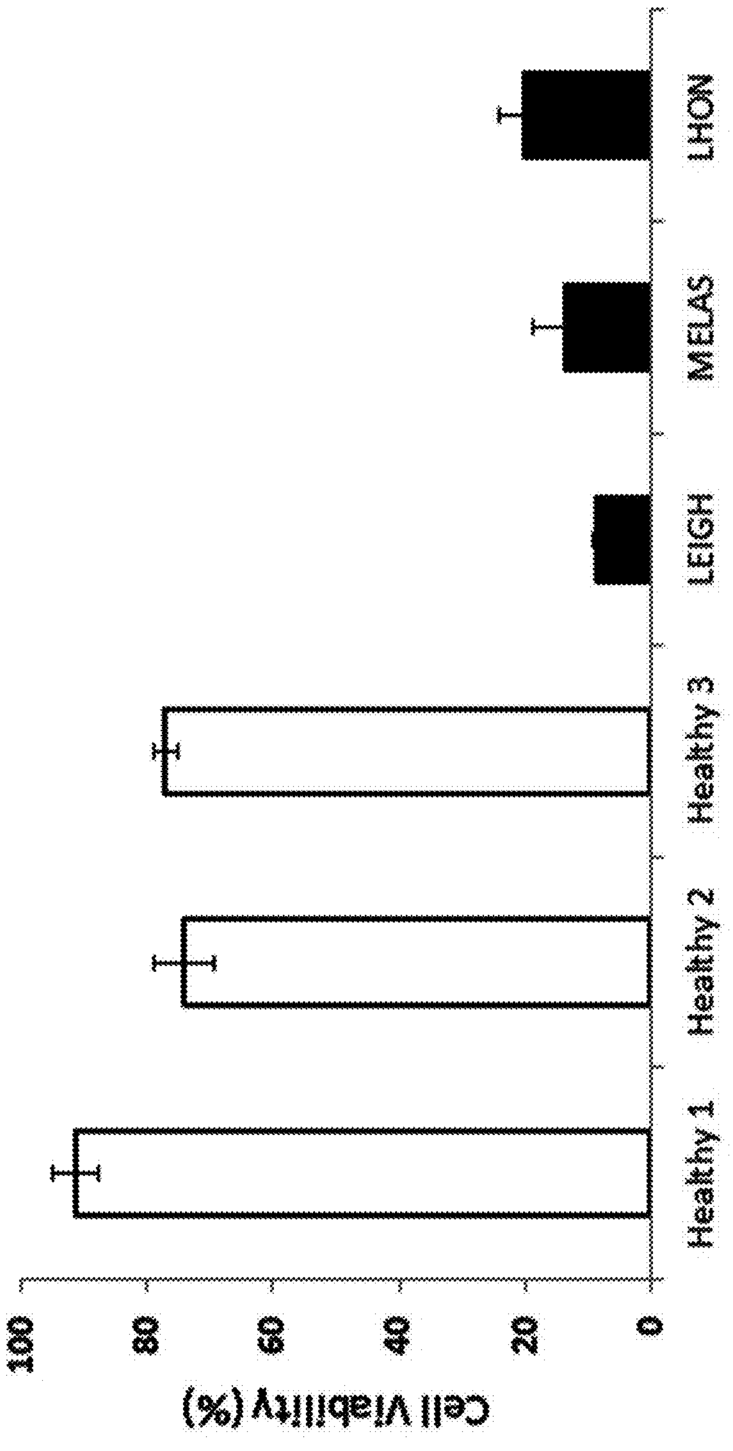
FIG. 1. Effect of L-buthionine-(S,R)-sulfoximine (BSO), an inhibitor of glutathione synthesis, on the viability of primary human fibroblasts derived from healthy individuals or derived from patients with Leigh syndrome, MELAS or LHON diseases. One day after treatment with 100 μM BSO, cells were washed and stained with Calcein-AM. Cell viability was determined as a function of fluorescence intensity.

To determine the effective concentration of the compounds (the concentrations that protect patient cells against oxidative stress-induced cell death) the applicant established an assay using stressed primary human fibroblasts from patients with Leigh syndrome, MELAS or LHON diseases. Utilising the inherent oxidative stress of fibroblasts from patients with mitochondrial disease, their oxidative burden was further increased by depleting cellular glutathione with an inhibitor of glutathione synthesis, L-buthionine-(S,R)-sulfoximine (BSO). As a result, while fibroblasts from healthy individuals retained full viability, patient fibroblasts exhibited complete cell death within 24 hr of the BSO insult (100 μM) (FIG. 1). Cells were seeded at a density of 3000 cells/well in a 96-well format and incubated with increasing concentrations of compounds in combination with BSO (100 μM, Sigma-aldrich). One day after treatment, the cells were washed twice and stained with a solution of 5 μM calcein-AM (Life technologies C3100MP) during 25 min in 199 medium without phenol red (Life technologies, 11043-023) at room temperature. After 2 washes with PBS (Phosphate buffered saline) the plate was read on a fluorescence plate reader (Fluostar Omega, BMG labtech) and the percentage of cell viability determined as a function of fluorescence intensity.

In Vivo: Placebo-Controlled, Single-Centre Study

The compounds as described herein were tested in a double-blinded, randomized, placebo-controlled, single-centre study in healthy male volunteers. The single ascending dose (SAD) part has a partial alternating crossover design and the multiple-ascending dose (MAD) part has a sequential group design. Randomization was 2:1 (2 active for each placebo).

Study Population

For both the SAD and MAD study, healthy men between 18 and 55 years of age with a body mass index (BMI) of 18.0-30.0 kg/$m^2$ were recruited. Good physical and mental health was established by medical history, physical examination, electrocardiogram (ECG) and vital signs recording, and results of clinical chemistry, hematology and urinalysis testing within 4 weeks prior to the first dose. Participants agreed to stay in the clinic during the first 24 hours after dosing (SAD) and during Day 8 (MAD) and refrain from multivitamins and dietary supplements and grapefruit juice at least 14 Days prior to the first dosing, from alcohol 7 Days prior to the first dosing, from strenuous exercise, beverages containing quinine and from xanthine-derivates (e.g. caffeine) 48 hours prior to the clinical admission and during the study. Only non-smokers (at least 3 months) were eligible for inclusion. Exclusion criteria included: clinically significant allergies, positive serology for hepatitis B surface antigen, hepatitis C antibodies, HIV1 of HIV2, history of alcohol or drug abuse in the past 2 years, history of cancer, surgery or active illness of the gastro-intestinal tract that might interfere with absorption, intake of any enzyme-affecting drugs in the 30 days prior to the first dosing period, use of any medication, herbal medicine or dietary supplement from 14 days prior to the first dosing (except for occasional paracetamol intake), participation in a trial of an investigational product in the 2 months prior to the first dosing, blood donation in the 2 months prior to the first dosing, history of hypersensitivity or idiosyncrasy to any of the components of the investigational drug, positive drug, alcohol or cotinine test at screening or admission, clinically relevant abnormal laboratory findings, ECG recordings, vital signs or physical or mental findings at screening, and/or major surgery and/or prolonged immobilisation (more than 2 weeks) within the 3 months prior to the screening.

Study Drug

A representative compound was used for testing in humans. More precisely, KH176 (or ((S)-6-hydroxy-2,5,7,8-tetramethyl-N-((R)-piperidin-3-yl)chroman-2-carboxamide hydrochloride; Patent application WO2014011047 A1) was available as a powder for reconstitution with saline. Placebo was a NaCl salt/bitrex powder for reconstitution with saline.

Study Design

The trial had a double-blinded, randomized, placebo-controlled, single-centre design. For the SAD part, a partial alternating crossover design and for the MAD part a sequential group design was applied.

In the SAD part the effects of 6 single orally administered ascending doses of KH176 or placebo were investigated alternately dosed to two groups of 6 healthy male subjects (4 active; 2 placebo per group). Dose escalation to the next dose level was done after evaluation of the safety and the first 24-hour pharmacokinetic results of the previous dose. The single dose part included a food effect investigation; the 100-mg dose was administered following the intake of a high calorie/high fat breakfast to the same subjects as who received this dose in fasting conditions. In the MAD study 3 multiple ascending doses of KH176 were administered for 7 Days to 3 sequential groups of 6 healthy male subjects each (4 active; 2 placebo per group).

Formulation and Administration

KH176 (solution) was administered orally. Single doses of 10, 30, 100, 300, 800 and 2000 mg were administered in the SAD part. Multiple oral doses of 100, 200 and 400 mg were administered b.i.d. for 7 Days in the MAD part. The starting dose for the SAD was ~150 fold lower than the no observable adverse effect level (NOAEL) of both dogs and rats. Anticipated exposures at this starting dose were just below the Minimum Anticipated Biological Effect Level (MABEL). Placebo (an in taste and appearance matching oral liquid) was also administered orally on one occasion in the single-ascending dose part and b.i.d. for 7 Days in the MAD part.

Safety Assessment

Safety was assessed using standard vital signs, clinical laboratory results for blood chemistry, haematology and urinalysis, continuous cardiac telemetry and a 12-lead ECG at 1, 2, 4, 6, 8, 12 and 24 h post dosing. The changes from baseline (pre-dose assessment on Day 1) for body weight, physical examinations, vital signs, ECG-variables and clinical laboratory variables were determined for each time point. Treatment-emergent laboratory and ECG abnormalities as well as adverse events were monitored throughout the study, up to 28 Days after the last study drug intake.

Preclinical studies of the compounds of the invention in rats demonstrated the occurrence of phospholipidosis (data not shown). Therefore, the presence of phospholipidosis was determined by the concentration of di-docosahexaenoyl (22:6)-bis(monoacylglycerol) phosphate (di-22:6-BMP) in a midstream urine sample and by electron microscopy of peripheral leucocytes at Day 1 and 7 in the MAD study (Pospischil A. et al, Exp. Toxicol Pathol 2010, 62:567-571).

Pharmacokinetic Analysis

Plasma samples for pharmacokinetic analyses were taken pre-dose and at 0.5, 1, 1.5, 2, 3, 6, 8, 12, and 24 h after dosing (SAD) and pre-dose at Day 1, 2, 4, 7, and post-dose at Day 1 and Day 7 at 0.5, 1, 1.5, 2, 3, 4, 6, 8, 12 h after dosing (MAD). All samples were stored at <−70° C. until analysis. Quantification of KH176 and its metabolite KH176m were performed using a validated LC-MS/MS method with good (max 15-20% CV) selectivity, precision and accuracy, little carry over effect, good stability of both the solutions and the samples. For mean value calculations, all values below the limit of quantification (LOQ) were set to zero. If <50% of the values at a given time point were below the LOQ (BLQ), these values were set to zero for calculation of the mean value. If >50% of the values at a given time point were BLQ, no mean value was calculated. The non-compartmental pharmacokinetic analysis was performed using Phoenix, Version 6.3 (Pharsight Corporation, Mountain View, CA, USA). Plasma concentration-time profiles of KH176 and its metabolite KH176m were determined for the SAD and MAD part and for trough concentrations in the MAD part. The PK parameters were calculated on the basis of the actual blood sampling time points relative to dosing. Selected pharmacokinetic parameters ($C_{max}$, $t_{max}$, $t_{1/2}$, $AUC_{last}$ and $AUC_{0-inf}$) following single-dose administration and selected pharmacokinetic parameters $C_{max}$, $t_{max}$, $t_{1/2}$, $AUC_{tau}$, the accumulation factor ($R_{acc}$) and time to reach steady state) following multiple dose administration were determined. In urine, the percentage of dose excreted in urine was determined for the single- and multiple-dose administration.

Pharmacodynamic Analysis

Blood samples for pharmacodynamic analyses were taken pre-dose and at 3, 6 and 24 h post dosing at Day 7 (MAD). All samples were stored in −80° C. until analysis. Quantification of oxidized and reduced glutathione was performed at York Bioanalytical solutions using a previously described validated method (Moore T et al, *J Chromatogr B Analyt Technol Biomed Life Sci* 2013, 929:51-55). Change from baseline in the concentrations of oxidized and reduced glutathione (GSH/GSSG) was calculated.

ECG Post-Hoc Analysis

During the interim evaluations at dose escalation, machine-read ECGs and telemetry in the clinic indicated a QT prolongation of KH176, as indicated by QTcB, the Bazett corrected QT interval, particularly strong at high dosages of the compound. The goal of this post-hoc optimization study was to repeat the ECG assessment with an highly automated computer-assisted approach where in addition to the re-evaluation of standard intervals (PR, QRS and QT intervals), a set of parameters describing repolarization morphology were considered. The morphology indices were the TpTe interval (interval from the T wave apex to the end of the T wave), the TpTe/QT index (the ratio between the TpTe interval and the QT interval), Tamp (the amplitude in microvolt units of the T wave) and TSym (an index of repolarization morphology based on the symmetry of the T wave).

ECGs were digitally recorded using a Schiller AT104 ECG machine (500 Hz, 1 μV). Cardiac interval measurements were performed on the Global Superimposed Median Beat (GSMB), a methodology that allows measurements that consider each of the 12 individual median beats [15]. This measurement methodology ensures that the PR, QRS, and QT interval are measured from the earliest onset in any lead to the latest deflection in any lead. Cardiologist overview of the computer-based measurements is based on the superimposed (overlapped) display of the individual median beats, to assure measurements are performed at the earliest onset of any viable lead to the latest offset of any viable lead.

The RR interval used for heart-rate correction of the QT interval (QTcB) was based on all the beats in the ten second recording.

Figure 3:
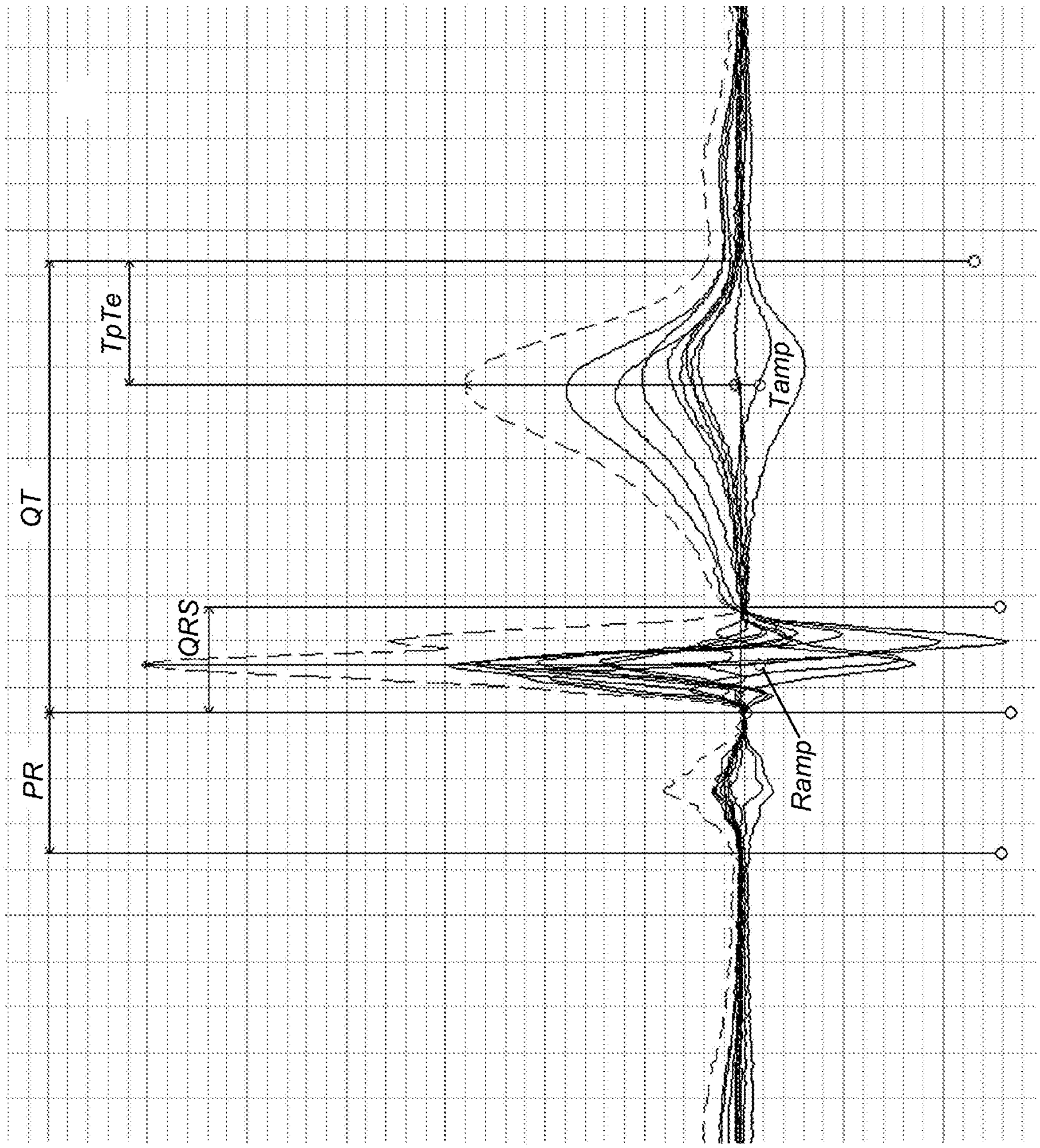
FIG. 3. Posthoc ECG assessment methodology.

Other cardiac parameters were computed from the 12-lead vector magnitude VM (e.g. the square root of the sum of squares at each digital sample) computed from the individual median beats. On the VM lead, the apex of the T wave is placed and used to compute the TpTe interval (using the end of the T wave from the GSMB) and the T wave amplitude (height in microvolt of the VM T peak from the isoelectric line). FIG. 3A shows an example with all the calipers involved: the GSMB leads are drawn in black and the VM lead is drawn in green. T wave symmetry index was computed using a proprietary approach based on Gaussian Mesa function modeling (GMF) of the repolarization waves (Badilini F et al. *J Electrocardiol* 2008, 41:588-594). Briefly, the ascending and descending phases of the VM T wave are modeled by two independent half-Gaussian curves (see FIG. 3). The standard deviations of these functions (σ1 and σ2) and indicators of the ascending/descending speed and their ratio is an index of symmetry (TSym=σ1/σ2; TSym=1 for a perfectly symmetric T wave, TSym<1 for slow-ascending/fast-descending T waves, T>1 for fast-ascending/slow-decending T waves).

For the pre-dose (baseline) ECGs, all parameters per time point were calculated as the averages of the triplicate ECGs. Computation of QTcB and QTcF was performed using the RR interval averaged from the total ECG acquisition duration (10 seconds) and in the case of the triplicate ECGs is based on the average QT and average HR of the replicate ECGs.

The over-reading cardiologist provided a clinical interpretation for each ECG at each time point. Each ECG was classified as Normal, Abnormal Clinically Insignificant (ACI), or Abnormal Clinically Significant (ACS). Results of this post-hoc analysis were used for an exposure-response evaluation for the changes in the electrophysiological parameters as a function of the concentration of KH176.

Ethics

All studies were conducted at the Drug Research Unit Ghent in accordance with the Declaration of Helsinki and the Good Clinical Practice guidelines established by the International Conference on Harmonization (ICH). An independent medical ethical committee approved the protocol (University Hospital of Ghent). All participants have signed informed consent prior to their enrolment.

Statistical Analysis

The tolerability and safety data were compared between KH176 and placebo using descriptive summary statistics. Pharmacokinetic and pharmacodynamic parameters were analyzed by treatment group on the per-protocol set and summarized using descriptive statistics. Dose proportionality of log transformed $C_{max}$ and AUC values was explored graphically. The effect of food on the pharmacokinetics was explored by calculating the geometric means and 90% confidence interval of the ratio (fed/fasted) for AUC and $C_{max}$. The pharmacodynamic endpoints were analyzed descriptively by treatment group on the per-protocol set as a change from baseline. Pharmacokinetic-effect modelling of PK/ECG data was explored visually and by an exposure-response evaluation for the changes in the electrophysiological parameters as a function of the concentration of KH176.

Results

In Vitro: Oxidative Stress-Induced Cell Death

Figure 2A:
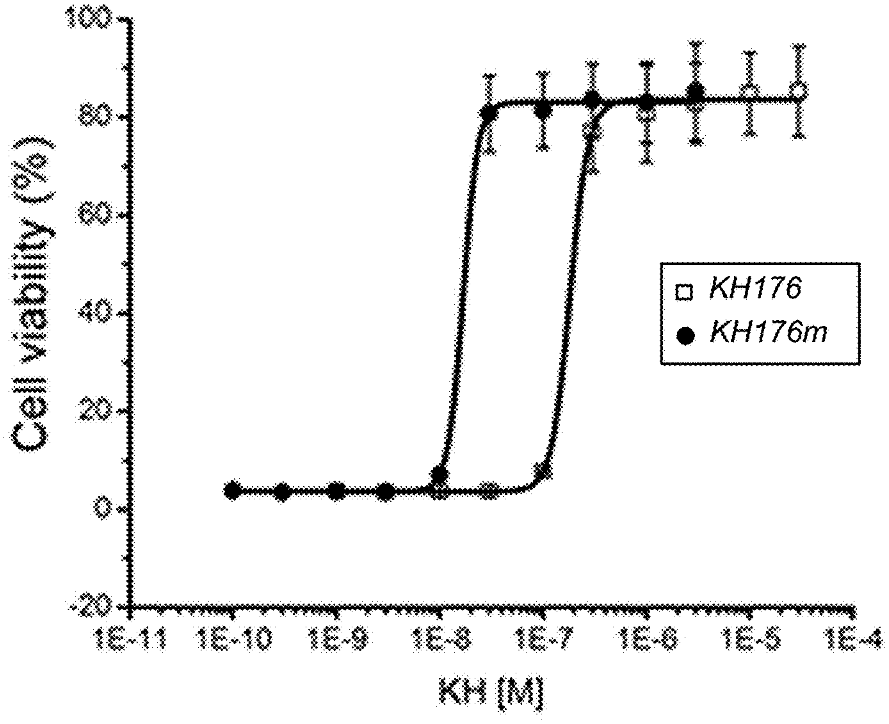
FIGS. 2A-2C. Effect of the compounds on oxidative stress-induced cell death. Primary human fibroblasts derived from patients with Leigh syndrome (2A), MELAS (2B) or LHON (2C) diseases, were treated with increasing concentrations of the compounds in combination with 100 μM BSO. The following day the cells were washed, stained with Calcein-AM and the fluorescence was measured. Cell viability is depicted as normalized against untreated cells. Each graph depicts the potency of the compound (filled square) and the corresponding metabolite (open square) to prevent cell death at selected concentrations.
Figure 2B:
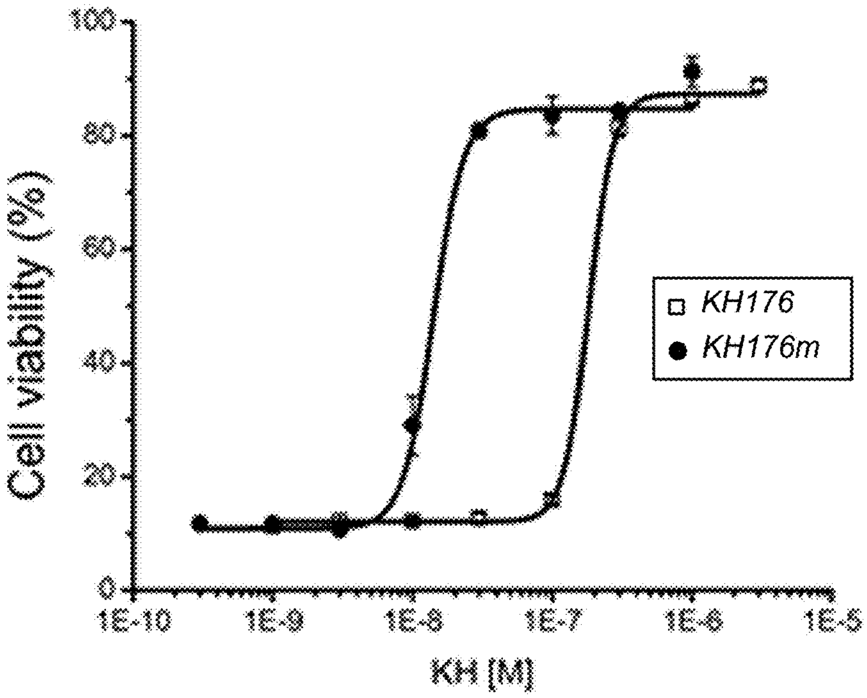
Figure 2C:
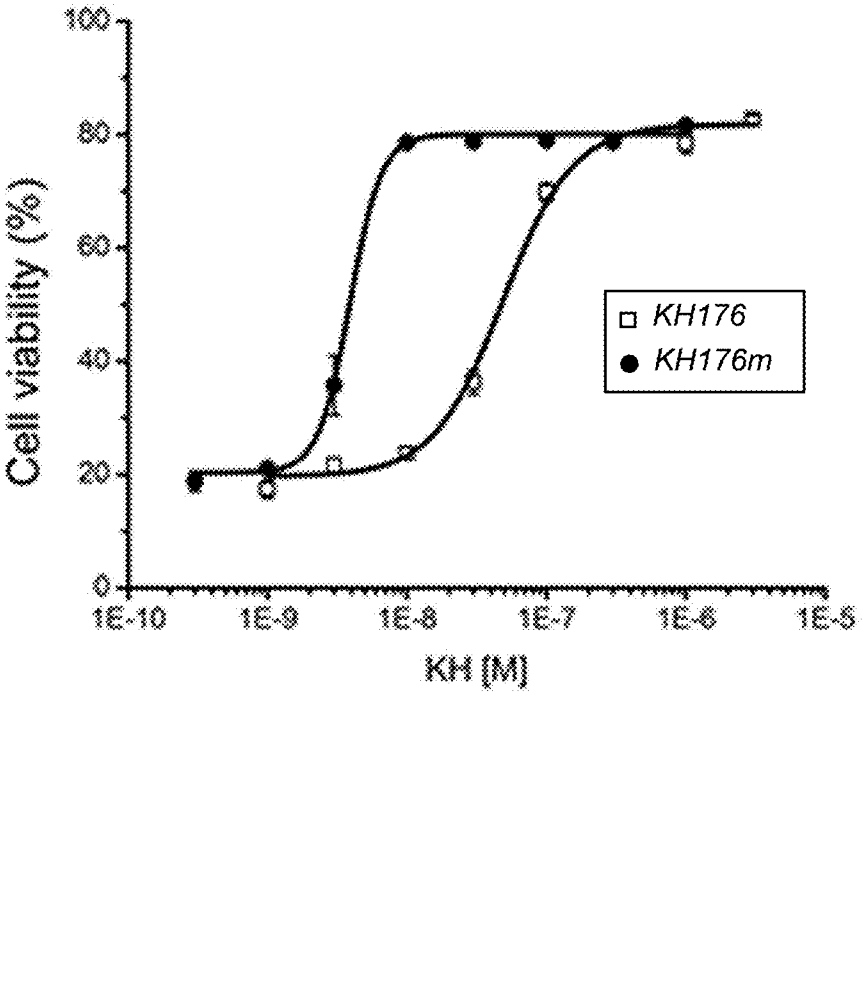

The cellular oxidative-stress protectant potency of KH176 and its metabolite KH176m was assessed in 3 different mitochondrial disease patient-derived fibroblasts (FIG. 2). As shown in FIG. 2, the compound KH176 and its metabolite KH176m were able to protect fibroblasts of mitochondrial patients from redox-induced toxicity. For fibroblasts derived from Leigh patients, the $EC_{50}$ (half maximum effective concentration) was 182 nM for KH176 and 16 nM for KH176m. Similarly, the $EC_{50}$ for KH176 and KH176m in fibroblasts derived from MELAS patients was respectively 182 nm and 14 nM, The $EC_{50}$ for KH176 and KH176m in fibroblasts derived from LHON patients was respectively 49 nM and 4 nM, In Vivo: Placebo-Controlled, Single-Centre Study Study Population For the SAD part of the study, 14 healthy male subjects divided in two groups of 7 subjects were included. For the MAD part of the study, 18 healthy male subjects divided in 3 groups of 6 subjects were included. Two subjects prematurely withdrew from the study for non-medical reasons and were replaced. There were no protocol violations in either part of the study that excluded subjects from the analysis set(s) and, therefore, all subjects included in this study were evaluable for pharmacokinetics, pharmacodynamics, safety, and tolerability. For demographics, see Table 3 below.

TABLE 3

Summary of demographic characteristics for subjects included in the SAD and MAD study.

| | SAD | | MAD | | | |
|---|---|---|---|---|---|---|
| | | | Group III | Group IV | Group V | |
| | Group I (N = 7)* | Group II (N = 7)* | 100 mg BID (N = 4) | 200 mg BID (N = 4) | 400 mg BID (N = 4) | Placebo (N = 6) |
| **Age (years)** | | | | | | |
| Mean (SD) | 30.4 (10.5) | 32.0 (11.3) | 40.8 (13.0) | 34.5 (11.6) | 44.0 (8.2) | 44.7 (9.8) |
| Median | 28.0 | 31.0 | 44.0 | 35.0 | 43.0 | 48.5 |
| Range | (22-52) | (18-45) | (24-51) | (23-45) | (37-53) | (28-54) |
| **Height (cm) at screening** | | | | | | |
| Mean (SD) | 178.07 (6.56) | 176.01 (8.11) | 184.63 (2.81) | 181.75 (5.25) | 175.70 (3.18) | 175.55 (8.25) |
| Median | 177.50 | 177.00 | 184.90 | 183.75 | 176.70 | 171.60 |
| Range | (165.7-184.5) | (163.0-187.5) | (181.5-187.2) | (174.0-185.5) | (171.1-178.3) | (170.4-191.5) |
| **Weight (kg) at screening** | | | | | | |
| Mean (SD) | 82.86 (10.56) | 74.29 (12.61) | 89.05 (11.84) | 77.85 (11.96) | 81.10 (4.82) | 72.03 (6.06) |
| Median | 80.00 | 78.60 | 89.30 | 80.30 | 82.80 | 72.30 |
| Range | (69.8-100.0) | (55.2-88.6) | (77.2-100.4) | (61.2-89.6) | (74.2-84.6) | (62.6-78.8) |
| **BMI ($kg/m^2$) at screening** | | | | | | |
| Mean (SD) | 26.09 (2.51) | 24.01 (4.01) | 26.10 (2.74) | 23.60 (3.82) | 26.28 (1.67) | 23.43 (1.98) |
| Median | 26.10 | 22.80 | 26.25 | 24.90 | 26.70 | 23.50 |
| Range | (22.5-29.4) | (19.0-29.6) | (23.1-28.8) | (18.2-26.4) | (23.9-27.8) | (21.2-26.6) |
| **Race** | | | | | | |
| White | 7 (100.0%) | 7 (100.0%) | 4 (100.0%) | 4 (100.0%) | 4 (100.0%) | 6 (100.0%) |

*6 subjects were enrolled of whom 1 withdrew and has been replaced

Safety and Tolerability

Following administration of a single dose of KH176 to subjects in the fasted state (SAD study), a total of 43 adverse events (AEs) were reported by 14 subjects (56%; Table 4A). The majority of AEs (35) was rated as mild in severity whereas there were 6 moderate and 2 severe AEs. Up to and including the 800 mg dose, no relationship to dose in the number of reported AEs or severity could be discerned. However, 28 of the 43 reported AEs were reported by subjects in the highest dose group of which 6 and 2 were of moderate and severe severity, respectively. The 2 severe AEs were nausea and headache. Following administration of placebo, a total of 7 AEs were reported by 3 subjects (25%). Of note, 4 of these AEs were rated as moderate in severity. Headache was the most frequently reported AE with a total of 7 subjects including 2 placebo subjects. The majority of AEs occurred incidentally, i.e., was reported by only 1 or 2 subjects. Adverse events reported by more than 2 subjects and not by placebo subjects were psychiatric symptoms, dizziness, oral paraesthesia and prolonged QT at the electrocardiogram and telemetry. All these events occurred in the highest dose group (2000 mg dose) and were reported by 3 subjects each.

Following administration of a multiple doses of KH176 (MAD study), a total of 29 AEs were reported by 10 subjects (83.3%; Table 4B). The majority of AEs (27) was rated as mild in severity whereas there were 2 moderate AEs, one each in the 200- and 400-mg dose groups. No relationship to dose in the number of reported AEs or severity could be discerned. Headache was the most frequently reported AE with a total of 11 subjects including 5 placebo subjects reporting this AE. Except for skin irritation, all AEs occurred incidentally, i.e., were reported by only 1 or 2 subjects in the KH176 treated subjects. Skin irritation was also reported by 2 placebo subjects and, therefore, no AE was reported by more than 2 KH176-treated subjects and not by placebo subjects.

Table 4. Summary of Treatment-Emergent Adverse Events by System Organ Class and Preferred Term

TABLE 4A

| SAD study | | | | | |
|---|---|---|---|---|---|
| System organ class<br>Preferred term | Group I<br>Placebo<br>(N = 6)<br>n (%) | Group II<br>Placebo<br>(N = 6)<br>n (%) | Group I<br>10 mg<br>(N = 4)<br>n (%) | Group II<br>30 mg<br>(N = 4)<br>n (%) | Group I<br>100 mg<br>(N = 4)<br>n (%) |
| Any TEAE | 2 (33.3%) | 1 (16.7%) | 2 (50.0%) | 3 (75.0%) | 4 (100.0%) |
| Blood and lymphatic system disorders | 0 | 0 | 0 | 1 (25.0%) | 0 |

TABLE 4A-continued

| SAD study | | | | | |
|---|---|---|---|---|---|
| Lymphadenopathy | 0 | 0 | 0 | 1 (25.0%) | 0 |
| Psychiatric disorders | 0 | 0 | 0 | 0 | 0 |
| Bradyphrenia | 0 | 0 | 0 | 0 | 0 |
| Depersonalisation | 0 | 0 | 0 | 0 | 0 |
| Hallucination, visual | 0 | 0 | 0 | 0 | 0 |
| Nervous system disorders | 2 (33.3%) | 0 | 0 | 2 (50.0%) | 3 (75.0%) |
| Dizziness | 0 | 0 | 0 | 0 | 0 |
| Dysgeusia | 0 | 0 | 0 | 0 | 0 |
| Headache | 2 (33.3%) | 0 | 0 | 1 (25.0%) | 3 (75.0%) |
| Presyncope | 0 | 0 | 0 | 1 (25.0%) | 0 |
| Cardiac Disorders | 0 | 0 | 0 | 0 | 0 |
| Bundle branch block right | 0 | 0 | 0 | 0 | 0 |
| Respiratory, thoracic and mediastinal disorders | 0 | 0 | 1 (25.0%) | 0 | 1 (25.0%) |
| Oropharyngeal discomfort | 0 | 0 | 0 | 0 | 1 (25.0%) |
| Rhinorrhoea | 0 | 0 | 1 (25.0%) | 0 | 1 (25.0%) |
| Gastrointestinal disorders | 1 (16.7%) | 1 (16.7%) | 0 | 1 (25.0%) | 1 (25.0%) |
| Abdominal pain | 0 | 1 (16.7%) | 0 | 0 | 1 (25.0%) |
| Diarrhoea | 0 | 1 (16.7%) | 0 | 0 | 0 |
| Nausea | 1 (16.7%) | 0 | 0 | 0 | 0 |
| Odynophagia | 0 | 0 | 0 | 1 (25.0%) | 0 |
| Paraesthesia oral | 0 | 0 | 0 | 0 | 0 |
| Retching | 0 | 0 | 0 | 0 | 0 |
| Vomiting | 0 | 0 | 0 | 0 | 0 |
| Musculoskeletal and connective tissue disorders | 1 (16.7%) | 0 | 1 (25.0%) | 1 (25.0%) | 0 |
| Arthralgia | 0 | 0 | 0 | 1 (25.0%) | 0 |
| Musculoskeletal stiffness | 0 | 0 | 1 (25.0%) | 0 | 0 |
| Pain in extremity | 1 (16.7%) | 0 | 0 | 0 | 0 |
| General disorders and administration site conditions | 1 (16.7%) | 0 | 0 | 0 | 1 (25.0%) |
| Catheter site pain | 0 | 0 | 0 | 0 | 0 |
| Chills | 0 | 0 | 0 | 0 | 0 |
| Fatigue | 0 | 0 | 0 | 0 | 1 (25.0%) |
| Influenza like illness | 1 (16.7%) | 0 | 0 | 0 | 0 |
| Malaise | 0 | 0 | 0 | 0 | 0 |
| Investigations | 0 | 0 | 0 | 0 | 0 |
| Blood pressure diastolic increased | 0 | 0 | 0 | 0 | 0 |
| Blood pressure systolic increased | 0 | 0 | 0 | 0 | 0 |
| Electrocardiogram QT prolonged | 0 | 0 | 0 | 0 | 0 |
| Eosinophil count increased | 0 | 0 | 0 | 0 | 0 |

| System organ class Preferred term | Group II 300 mg (N = 4) n (%) | Group I 800 mg (N = 4) n (%) | Group II 2000 mg (N = 4) n (%) | Group I Placebo + Food (N = 2) n (%) | Group I 100 mg + Food (N = 4) n (%) |
|---|---|---|---|---|---|
| Any TEAE | 1 (25.0%) | 0 | 4 (100.0%) | 1 (50.0%) | 1 (25.0%) |
| Blood and lymphatic system disorders | 0 | 0 | 0 | 0 | 0 |
| Lymphadenopathy | 0 | 0 | 0 | 0 | 0 |
| Psychiatric disorders | 0 | 0 | 3 (75.0%) | 0 | 0 |
| Bradyphrenia | 0 | 0 | 1 (25.0%) | 0 | 0 |
| Depersonalisation | 0 | 0 | 1 (25.0%) | 0 | 0 |
| Hallucination, visual | 0 | 0 | 1 (25.0%) | 0 | 0 |
| Nervous system disorders | 1 (25.0%) | 0 | 3 (75.0%) | 0 | 0 |
| Dizziness | 0 | 0 | 3 (75.0%) | 0 | 0 |
| Dysgeusia | 1 (25.0%) | 0 | 0 | 0 | 0 |
| Headache | 0 | 0 | 1 (25.0%) | 0 | 0 |
| Presyncope | 0 | 0 | 0 | 0 | 0 |
| Cardiac Disorders | 0 | 0 | 2 (50.0%) | 0 | 0 |
| Bundle branch block right | 0 | 0 | 2 (50.0%) | 0 | 0 |
| Respiratory, thoracic and mediastinal disorders | 0 | 0 | 0 | 0 | 0 |
| Oropharyngeal discomfort | 0 | 0 | 0 | 0 | 0 |
| Rhinorrhoea | 0 | 0 | 0 | 0 | 0 |
| Gastrointestinal disorders | 0 | 0 | 4 (100.0%) | 0 | 0 |
| Abdominal pain | 0 | 0 | 0 | 0 | 0 |
| Diarrhoea | 0 | 0 | 0 | 0 | 0 |
| Nausea | 0 | 0 | 2 (50.0%) | 0 | 0 |
| Odynophagia | 0 | 0 | 0 | 0 | 0 |
| Paraesthesia oral | 0 | 0 | 3 (75.0%) | 0 | 0 |

TABLE 4A-continued

| SAD study | | | | | |
|---|---|---|---|---|---|
| Retching | 0 | 0 | 1 (25.0%) | 0 | 0 |
| Vomiting | 0 | 0 | 2 (50.0%) | 0 | 0 |
| Musculoskeletal and connective tissue disorders | 0 | 0 | 0 | 0 | 0 |
| Arthralgia | 0 | 0 | 0 | 0 | 0 |
| Musculoskeletal stiffness | 0 | 0 | 0 | 0 | 0 |
| Pain in extremity | 0 | 0 | 0 | 0 | 0 |
| General disorders and administration site conditions | 0 | 0 | 2 (50.0%) | 0 | 1 (25.0%) |
| Catheter site pain | 0 | 0 | 0 | 0 | 1 (25.0%) |
| Chills | 0 | 0 | 1 (25.0%) | 0 | 0 |
| Fatigue | 0 | 0 | 0 | 0 | 0 |
| Influenza like illness | 0 | 0 | 0 | 0 | 0 |
| Malaise | 0 | 0 | 1 (25.0%) | 0 | 0 |
| Investigations | 0 | 0 | 3 (75.0%) | 1 (50.0%) | 0 |
| Blood pressure diastolic increased | 0 | 0 | 1 (25.0%) | 0 | 0 |
| Blood pressure systolic increased | 0 | 0 | 1 (25.0%) | 0 | 0 |
| Electrocardiogram QT prolonged | 0 | 0 | 3 (75.0%) | 0 | 0 |
| Eosinophil count increased | 0 | 0 | 0 | 1 (50.0%) | 0 |

n = number of subjects;
TEAE = Treatment-Emergent Adverse Event

TABLE 4B

| MAD study | | | | |
|---|---|---|---|---|
| | Group III 100 mg BID (N = 4) n (%) | Group IV 200 mg BID (N = 4) n (%) | Group V 400 mg BID (N = 4) n (%) | Placebo (N = 6) n (%) |
| Any TEAE | 3 (75.0%) | 3 (75.0%) | 4 (100.0%) | 5 (83.3%) |
| Infections and infestations | 1 (25.0%) | 0 | 0 | 0 |
| Nasopharyngitis | 1 (25.0%) | 0 | 0 | 0 |
| Psychiatric disorders | 0 | 0 | 1 (25.0%) | 0 |
| Nightmare | 0 | 0 | 1 (25.0%) | 0 |
| Nervous system disorders | 2 (50.0%) | 2 (50.0%) | 1 (25.0%) | 3 (50.0%) |
| Dizziness | 0 | 0 | 0 | 1 (16.7%) |
| Head discomfort | 0 | 1 (25.0%) | 0 | 1 (16.7%) |
| Headache | 2 (50.0%) | 1 (25.0%) | 1 (25.0%) | 3 (50.0%) |
| Eye disorders | 1 (25.0%) | 1 (25.0%) | 0 | 0 |
| Conjunctival haemorrhage | 1 (25.0%) | 0 | 0 | 0 |
| Eye irritation | 1 (25.0%) | 0 | 0 | 0 |
| Vision blurred | 0 | 1 (25.0%) | 0 | 0 |
| Gastrointestinal disorders | 1 (25.0%) | 0 | 2 (50.0%) | 2 (33.3%) |
| Abdominal pain | 1 (25.0%) | 0 | 0 | 0 |
| Diarrhoea | 0 | 0 | 1 (25.0%) | 0 |
| Nausea | 0 | 0 | 1 (25.0%) | 2 (33.3%) |
| Skin and subcutaneous tissue disorders | 0 | 1 (25.0%) | 2 (50.0%) | 2 (33.3%) |
| Rash macular | 0 | 1 (25.0%) | 0 | 0 |
| Skin irritation | 0 | 1 (25.0%) | 2 (50.0%) | 2 (33.3%) |
| Renal and urinary disorders | 0 | 0 | 1 (25.0%) | 0 |
| Polyuria | 0 | 0 | 1 (25.0%) | 0 |
| General disorders and administration site conditions | 1 (25.0%) | 0 | 0 | 1 (16.7%) |
| Feeling cold | 0 | 0 | 0 | 1 (16.7%) |
| Feeling hot | 1 (25.0%) | 0 | 0 | 0 |
| Investigations | 0 | 0 | 4 (100.0%) | 0 |
| Blood creatine phosphokinase increased | 0 | 0 | 1 (25.0%) | 0 |
| Electrocardiogram QT prolonged | 0 | 0 | 1 (25.0%) | 0 |
| Lipase increased | 0 | 0 | 2 (50.0%) | 0 |
| Injury, poisoning and procedural complications | 0 | 0 | 1 (25.0%) | 1 (16.7%) |
| Wound | 0 | 0 | 1 (25.0%) | 1 (16.7%) |

n = number of subjects;
TEAE = Treatment-Emergent Adverse Event

The level of di-22:6-BMP was variable at baseline. There was no increase in di-22:6-BMP for the treatment groups versus placebo (change from Day 1 to Day 7 0.74-2.50;-1.44-1.32 and −0.69-1.46 ng/mg creatinine for group III, IV and V respectively and −0.92-4.31 ng/mg creatinine for placebo). No increased prevalence of the presence of phospholipidosis in either granulocytes or monocytes as evaluated by electron microscopy was present in the KH176-treated group versus the placebo-treated group. Hence, in contrast to preclinical studies in rats, we did not observe an increased prevalence of the presence of phospholipidosis.

Pharmacokinetic Analysis

SAD study: The plasma concentrations-time profiles of KH176 (FIG. 4A) showed that the median $t_{max}$ was between 0.75 and 1.5 h after administration and varied little with dose. Thereafter, the KH176 concentrations decreased in a biphasic way. The $t_{1/2}$ was approximately 10 h and varied little among dose groups (Table 5). The elimination phase following administration of a dose of 10 mg was not well characterized and, therefore, $t_{1/2}$ could not be estimated for this dose only.

The shape of the plasma concentration-time profiles of KH176m (FIG. 4B) resembled that of the parent compound but concentrations were lower. $C_{max}$ was reached at the same time or slightly later when compared to KH176 (table 6). Thereafter, KH176m plasma concentrations decreased in a biphasic way and the elimination was characterized by a $t_{1/2}$ of approximately 16 h without any notable effect of dose.

In the presence of food, the absorption of KH176 was slower as indicated by a median $t_{max}$ that shifted from approximately 1 h in fasted condition to 2.5 h in fed condition for both analytes (Table 5). Exposure under fed conditions in terms of $AUC_{0-inf}$ increased slightly for KH176 whereas that to KH176m decreased slightly ($AUC_{0-inf}$ 1.28 (90% Cl 1.12-1.45) for KH176 and 0.90 (90% Cl 0.57-1.41) for KH176m). The $t_{1/2}$ was not affected by food.

A graphical exploration for dose-proportionality of the pharmacokinetics of KH176 indicated that with increasing single dose there was a more than proportional increase in $C_{max}$ and $AUC_{0-inf}$ (FIG. 5).

Regardless of the dose and when combining KH176 and KH176m, approximately 16% of the administered dose was excreted in urine. Unchanged KH176 accounted for approximately 12%.

TABLE 5A

Summary of plasma pharmacokinetic variables of KH176.

| | | | SAD study | | | |
|---|---|---|---|---|---|---|
| Dose Food status | | | 10 mg (N = 4) fasted | 30 mg (N = 4) fasted | 100 mg (N = 4) fasted | 100 mg (N = 4) fed |
| $C_{max}$ | (ng/mL) | Geomean | 12.9 | 56.2 | 167 | 165 |
| | | CV % geomean | 21.3 | 21.0 | 27.2 | 7.40 |
| $t_{max}$* | (h) | Geomean | 1.25 | 1.25 | 1.00 | 2.50 |
| | | CV % geomean | (0.500-1.50) | (0.500-1.50) | (0.500-2.00) | (2.00-3.00) |
| $AUC_{last}$ | (h*ng/mL) | Geomean | 75.0 | 389 | 1310 | 1650 |
| | | CV % geomean | 14.8 | 8.16 | 16.7 | 1.67 |
| $AUC_{0-inf}$ | (h*ng/mL) | Geomean | | 474 | 1540 | 1970 |
| | | CV % geomean | | 8.39 | 13.1 | 1.04 |
| $t_{1/2}$ | (h) | Geomean | NA | 10.3 | 9.10 | 9.09 |
| | | CV % geomean | | 14.6 | 15.2 | 3.83 |

| Dose Food status | | | 300 mg (N = 4) fasted | 800 mg (N = 4) fasted | 2000 mg (N = 4) fasted |
|---|---|---|---|---|---|
| $C_{max}$ | (ng/mL) | Geomean | 766 | 2170 | 5990 |
| | | CV % geomean | 53.9 | 27.9 | 20.9 |
| $t_{max}$* | (h) | Geomean | 0.992 | 1.50 | 0.750 |
| | | CV % geomean | (0.500-3.00) | (1.00-1.50) | (0.500-3.00) |
| $AUC_{last}$ | (h*ng/mL) | Geomean | 6320 | 21000 | 61200 |
| | | CV % geomean | 20.2 | 27.5 | 9.07 |
| $AUC_{0-inf}$ | (h*ng/mL) | Geomean | 7500 | 25800 | 79100 |
| | | CV % geomean | 19.1 | 33.9 | 8.82 |
| $t_{1/2}$ | (h) | Geomean | 9.64 | 9.80 | 11.5 |
| | | CV % geomean | 4.29 | 19.1 | 4.73 |

Geomean = geometric mean;

h = hour;

NA = not assessable;

R = accumulation ratio;

*median (range)

TABLE 5B

MAD study

| | | | MAD study Dose | | |
|---|---|---|---|---|---|
| | | | 100 mg b.i.d (n = 4) | | 200 mg b.i.d (n = 4) |
| | | | Day | | |
| | | | 1 | 7 | 1 |
| $C_{max}$ | (ng/mL) | Geomean | 184 | 353 | 313 |
| | | CV % geomean | 57.0 | 19.1 | 20.0 |
| $t_{max}$* | (h) | Geomean | 1.25 | 1.00 | 1.75 |
| | | CV % geomean | (0.500-8.00) | (0.500-1.50) | (1.50-2.00) |
| $AUC_{tau}$ | (h * ng/mL) | Geomean | 1090 | 2760 | 2250 |
| | | CV % geomean | 49.3 | 22.6 | 26.1 |
| Racc | | Geomean | | 2.52 | |
| | | CV % geomean | | 31.2 | |

| | | | MAD study Dose | | |
|---|---|---|---|---|---|
| | | | 200 mg b.i.d (n = 4) | 400 mg b.i.d (n = 4) | |
| | | | Day | | |
| | | | 7 | 1 | 7 |
| $C_{max}$ | (ng/mL) | Geomean | 748 | 1330 | 2100 |
| | | CV % geomean | 29.3 | 27.3 | 27.2 |
| $t_{max}$* | (h) | Geomean | 2.00 | 1.00 | 1.50 |
| | | CV % geomean | (1.50-2.00) | (0.500-1.50) | (0.500-3.00) |
| $AUC_{tau}$ | (h * ng/mL) | Geomean | 5960 | 6890 | 14900 |
| | | CV % geomean | 26.8 | 19.2 | 28.2 |
| Racc | | Geomean | 2.65 | | 2.17 |
| | | CV % geomean | 2.5 | | 14.4 |

Geomean = geometric mean;
h = hour;
R = accumulation ratio;
*median (range)

Table 6. Summary of Plasma Pharmacokinetic Variables of KH176m

TABLE 6A

SAD study

| | | | SAD study | | | |
|---|---|---|---|---|---|---|
| | | | 10 mg (N = 4) fasted | 30 mg (N = 4) fasted | 100 mg (N = 4) fasted | 100 mg (N = 4) fed |
| $C_{max}$ | (ng/mL) | Geomean | 14.2 | 49.4 | 168 | 117 |
| | | CV % geomean | 49.5 | 9.00 | 29.6 | 20.0 |
| $t_{max}$* | (h) | Geomean | 1.25 | 1.50 | 1.25 | 2.50 |
| | | CV % geomean | (1.00-2.00) | (1.00-2.00) | (1.00-2.00) | (2.00-3.00) |
| $AUC_{last}$ | (h* ng/mL) | Geomean | 151 | 547 | 1810 | 1590 |
| | | CV % geomean | 26.7 | 12.4 | 37.4 | 26.1 |
| $AUC_{0-inf}$ | (h* ng/mL) | Geomean | 234 | 881 | 2690 | 2410 |
| | | CV % geomean | 26.7 | 19.6 | 38.4 | 29.1 |
| $t_{1/2}$ | (h) | Geomean | 16.6 | 17.8 | 15.4 | 14.9 |
| | | CV % geomean | 5.86 | 19.0 | 8.44 | 7.86 |

| | | | SAD study | | |
|---|---|---|---|---|---|
| Dose Food status | | | 300 mg (N = 4) fasted | 800 (N = 4) fasted | 2000 mg (N = 4) fasted |
| $C_{max}$ | (ng/mL) | Geomean | 497 | 1100 | 1780 |
| | | CV % geomean | 17.6 | 9.58 | 26.3 |

TABLE 6A-continued

| SAD study | | | | | |
|---|---|---|---|---|---|
| $t_{max}$* | (h) | Geomean<br>CV % geomean | 1.24<br>(1.00-2.00) | 1.50<br>(1.50-2.00) | 1.75<br>(1.00-2.00) |
| $AUC_{last}$ | (h* ng/mL) | Geomean<br>CV % geomean | 4830<br>11.8 | 11700<br>20.2 | 23900<br>22.2 |
| $AUC_{0-inf}$ | (h* ng/mL) | Geomean<br>CV % geomean | 6890<br>11.0 | 18700<br>26.7 | 41300<br>10.5 |
| $t_{1/2}$ | (h) | Geomean<br>CV % geomean | 14.3<br>18.9 | 17.2<br>18.5 | 18.9<br>18.7 |

Geomean = geometric mean;
h = hour;
R = accumulation ratio;
*median (range)

TABLE 6B

MAD study

| | | | MAD study Dose | | | | | |
|---|---|---|---|---|---|---|---|---|
| | | | 100 mg b.i.d (n = 4) | | 200 mg b.i.d (n = 4) Day | | 400 mg b.i.d (n = 4) | |
| | | | 1 | 7 | 1 | 7 | 1 | 7 |
| $C_{max}$ | (ng/mL) | Geomean | 99.4 | 152 | 251 | 250 | 550 | 450 |
| | | CV % geomean | 20.9 | 37.5 | 18.0 | 10.6 | 14.1 | 28.3 |
| $t_{max}$* | (h) | Geomean | 1.50 | 1.00 | 1.75 | 1.50 | 1.25 | 1.50 |
| | | CV % geomean | (1.00-8.00) | (1.00-2.03) | (1.00-2.00) | (1.00-2.00) | (1.00-1.50) | (1.00-3.00) |
| $AUC_{tau}$ | (h*ng/mL) | Geomean | 702 | 1310 | 1680 | 2220 | 3600 | 4270 |
| | | CV % geomean | 29.2 | 29.5 | 21.0 | 12.7 | 11.1 | 30.5 |
| Racc | | Geomean | | 1.86 | | 1.32 | | 1.19 |
| | | CV % geomean | | 46.7 | | 13.1 | | 24.7 |

Geomean = geometric mean;
h = hour;
R = accumulation ratio;
*median (range)

MAD study: Visual inspection of the mean trough concentration-time curves indicated that steady concentrations of KH176 were reached by Day 4 of dosing (of note: Day 4 was the first time point of measurement of trough values; FIG. 4C).

The plasma concentration-time profiles of KH176 after single- and multiple-dose administration were similar. Peak concentrations were attained between 1 and 2 h after drug administration (Table 5). Following attainment of $C_{max}$, the KH176 plasma concentrations declined rapidly. KH176 accumulated as shown by values for the accumulation index between doses varying from 2.17 to 2.65.

Figure 4D:
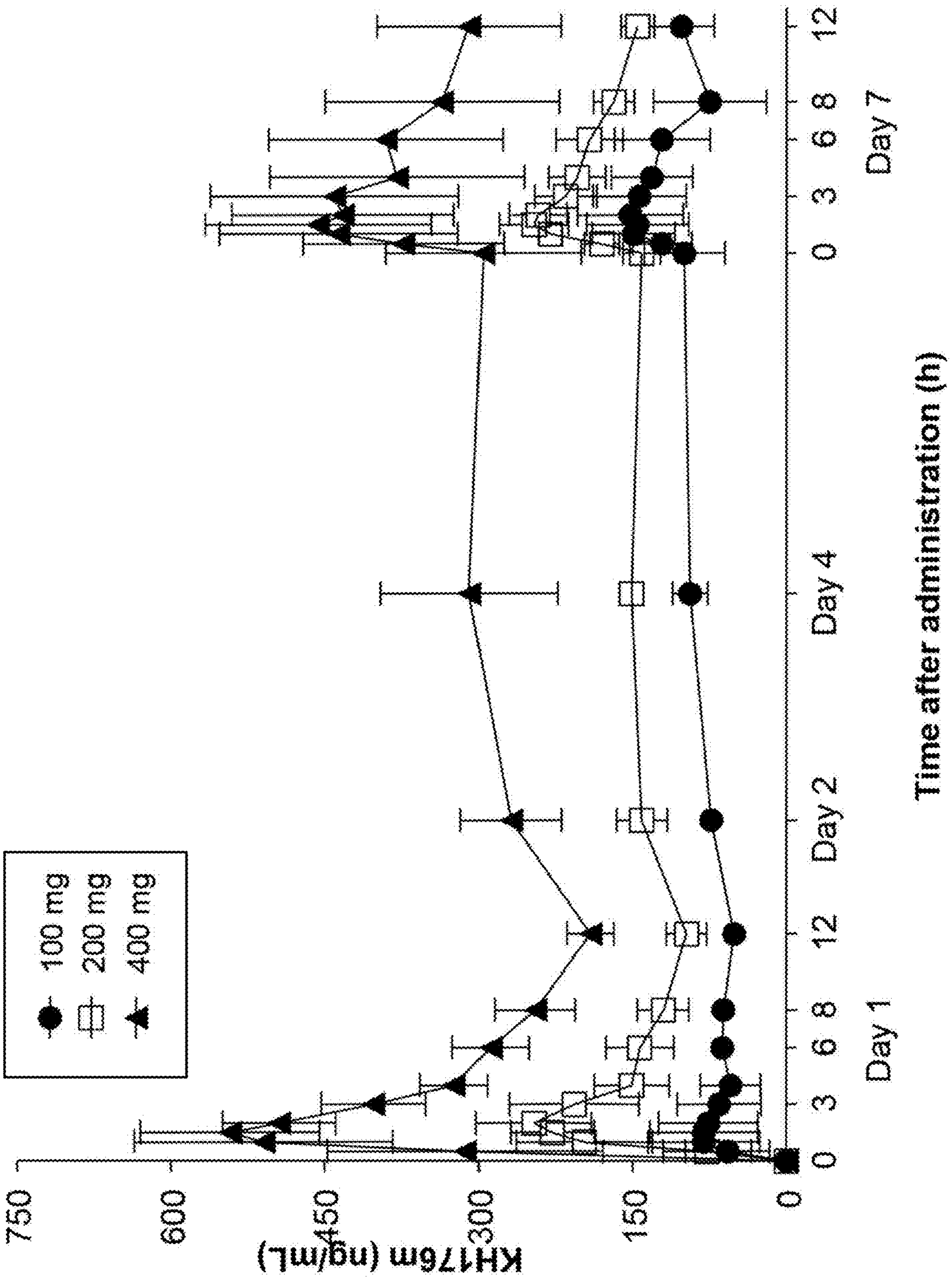

After multiple dosing, the shape of the plasma concentration-time profiles of KH176m resembled that of parent compound but concentrations were lower (FIG. 4D). On Day 7, $C_{max}$ was reached at approximately the same time when compared to KH176. After multiple dosing, the accumulation of the metabolite KH176m was less pronounced when compared to that of KH176 as indicated by values for the accumulation index varying from 1.19 to 1.86.

A graphical exploration for dose-proportionality of the pharmacokinetics of KH176 after multiple dosing indicated that with increasing multiple doses there was a more than proportional increase in $C_{max}$ and $AUC_{tau}$, which was most pronounced at the 400 mg dose (FIG. 5).

On Day 7 and when combining KH176 and KH176m, the % dose excreted in urine varied from 18.0 to 25.1% between doses. Unchanged KH176 accounted for 14.0 to 18.1%.

Pharmacodynamic Analysis

No significant alterations in the GSH/GSSG ratio were observed.

Posthoc Analysis QT Prolongation

A QTcF prolongation was present after single-dose administration of 800 and 2000 mg KH176 (see FIG. 8 for a representative example). The largest median baseline increase observed was 46.8 ms (1 h post-dose), whereas the largest individual change was 64.7 ms (2000 mg group; FIG. 6). This QTcF prolongation was associated with moderate but clear changes of morphology, namely a reduction of the T wave amplitude, a prolongation of the TpTe interval (in both absolute terms and relatively to the QT interval), and the symmetry (shape) of the T wave. At lower doses, KH176 does not seem to affect repolarization. Changes were also observed on other cardiac intervals: the QRS interval increased but only at a dose of 2000 mg, whereas the PR interval increased progressively also at lower doses of KH176.

The MAD part of the study showed the same effects, particularly for the 400 mg dose group (FIG. 6). A dose of 100 mg b.i.d. had no effect on QTcF and the time curve for this dose was indistinguishable from placebo. On Day 4 and later, administration of 200 mg b.i.d. increased QTcF and a median maximum change from baseline was observed on Day 5 of 13 msec. A further increase in QTcF was observed with a dose of 400 mg b.i.d. and the median maximum change from baseline at trough of 29 msec was observed on Day 6. Table 7 shows the largest median an largest individual increase in the ECG parameters for the SAD and the MAD study.

Clinically relevant changes were observed in at the peak concentrations in 2 individuals in the 2000 mg subgroup and did not include appearance of notched and/or bumps on any of the T-waves (all leads).

When the change in the TpTe interval is correlated to the KH176-exposure, a clear dose-dependency is observed (FIG. 7). In exposures lower than 500 ng/ml, no significant prolongation of the TpTe interval compared to placebo was observed. When increasing the dose and the plasma concentration, the TpTe interval increases. When the highest (non-tolerated) dose was administered (2000 mg), all subjects have a prolonged TpTe interval.

b.i.d. Headache was the most frequently reported AE in both the KH176—and the placebo treated groups. Although there was no clear dose-response relationship for any of the adverse events after single and multiple dose administration, unforeseen markedly more severe adverse events were reported after a single dose of 2000 mg. At this dose, nausea, vomiting, dizziness and psychiatric disturbances were reported, along with a prolonged corrected QT time.

The shape of the plasma concentration-time profiles of KH176 and its metabolite KH176m were similar after single- and multiple-dose administration. The pharmacokinetics of KH176 showed several surprising aspects. In particular, the pharmacodynamics of KH176 were characterized by a i) median $t_{max}$ between 0.75 and 2.0 h, ii) terminal $t_{1/2}$ of about 10 h, iii) biphasic elimination, and a iv) more than dose proportional increases in both $C_{max}$ and AUC. These pharmacodynamics could not have been predicted. In particular, the unexpected more than dose proportional increases in both $C_{max}$ and AUC should be considered when administrating the compound. We discovered that when a threshold concentration of the compound is reached, an increasing amount of the compound becomes available in the blood stream, which may cause side effects as described herein. Hence, a particular safe dose of the compound is a dose that does not show a more than dose-proportional increase in at least one of $C_{max}$ and AUC (see FIG. 5), e.g. a single dose should preferably stay below 300 mg.

In vitro, KH176 is metabolized by CYP3A4 and excreted by the PgP efflux pump. We did not observe signs for auto-induction in this study such as a decline in pre-dose concentrations. Without wishing to be bound by any theory, the more than proportional increase with dose could be caused by saturation of the PgP efflux pump for which KH176 is a substrate, as evidenced by the fact that half-life and clearance doesn't change with dose, but rather the availability seems to change with dose.

TABLE 7

Largest median an largest individual increase in the ECG parameters for the SAD and the MAD study

| | | SAD study | | | | MAD study | | | |
|---|---|---|---|---|---|---|---|---|---|
| | | 800 mg | | 2000 mg | | 200 mg | | 400 mg | |
| | | Largest median baseline increase | Largest individual increase | Largest median baseline increase | Largest individual increase | Largest median baseline increase | Largest individual increase | Largest median baseline increase | Largest individual increase |
| QTcF | | 9 | 26 | 46.8 | 64.7 | 13.3 | 28.3 | 29.2 | 43.7 |
| HR | bpm | | | 10.3 | 23.3 | | | | |
| PR interval | ms | 10.3 | 19.3 | 15.3 | 20.7 | 12 | | 19 | |
| QRS interval | ms | 5.3 | 8 | 25.7 | 30 | | | 9.7 | 15.3 |
| TpTe interval | ms | 21.7 | 36.7 | 58.7 | 76 | 24 | 46 | 42.3 | 62.7 |
| T-wave amplitude | MV | 600 | 706 | 734 | 994 | | | | |
| T-wave symmetry index | | 0.42 | 0.85 | 0.87 | 1.1 | 0.45 | 0.6 | 0.63 | 0.99 |

Conclusions

Mitochondrial disorders are a devastating group of disorders for which there is an urgent need for treatment development. We demonstrated that the compound KH176 showed promising properties in ameliorating the viability and phenotype of cells and mice affected by mitochondrial disease. In particular, in vitro assays with KH176 and KH176m demonstrated a low $EC_{50}$ of 182 nM (around 60 ng/mL) for KH176 and 16 nM (around 5.8 ng/ml) for KH176m. In the same in vitro setting, the $EC_{50}$ of the well-known drug Idebenone (a $CoQ_{10}$ variant) was 1470 nM.

We further evaluated the tolerability, safety, pharmacokinetics and pharmacodynamics of single- and multiple-ascending doses of KH176 in healthy male subjects. KH176 was well tolerated in doses up to 800 mg SD and 400 mg Up to 25.1% of an administered dose is excreted via urine after multiple dosing. Based on the results of the multiple-dose administration, steady state was reached at the first time point of measurement of trough concentrations (Day 4). Based on the estimated $t_{1/2}$, it is expected that steady state will be reached after 2 to 3 Days of dosing.

In steady state conditions at 100 mg BID dosing the maximum concentration reached ranged within 303-458 ng/ml for KH176 and 89.4-204 ng/ml for KH167m (hence the maximum concentrations of the active moieties ranged within 392.4-662 ng/ml). The area under the curve for one dosing interval (i.e. 12 hours) at steady state (AUCtau) ranged within 2130-3680 h·ng/ml for KH176 and 851-1570 h·ng/ml for KH183, meaning that average concentrations ranged within 177.5-306.6 ng/mL for KH176 and 70.9-130.8 ng/ml for KH176m.

KH176 was well tolerated in the presence of food, and the tolerability and safety profile in the presence and absence of food was similar. Although the point estimates (as well as the sample covariance) for both $C_{max}$ and $AUC_{0\text{-}inf}$ did not completely remain within the usually accepted range of 0.8 to 1.25 (Table 5), no special measures are warranted regarding the intake of KH176.

KH176 clearly modifies cardiac repolarisation in a dose-dependent manner. QTcF prolongation was present after single-dose administration of 800 and 2000 mg and after multiple doses of 400 mg of KH176 b.i.d. Post-hoc studies showed that this QTcF prolongation was associated with changes in morphology and other cardiac intervals. Detailed analysis of the ECGs during the single-dose administration of 200, 100, 30 and 10 mg and multiple oral doses of 100 and 200 mg b.i.d. showed no cardiac electrophysiological abnormalities. The KH176 related changes in cardiac repolarisation include a reduction of T wave amplitude, a prolongation of the TpTe interval and a reduction of the T wave symmetry index. The reduction in T wave amplitude is largely explained by changes in heart rate and also seen in the placebo group. The prolongation of the TpTe interval and the reduction on the symmetry index indicate a prolongation of the descending phase of the T wave. With pure hERG blockade, there is a direct relationship between increasing plasma drug concentrations and the risk for torsades. Importantly, although the specific T wave morphology changes observed in this study have been associated with the hERG potassium channel blockade (Johannesen L, et al. *Clin Pharmacol Ther* 2014, 96:549-558). The $IC_{50}$ of hERG blocking for KH176 was 3 times higher than the $C_{max}$ for the highest dose.

Notably, there were 2 subjects with a potentially clinically relevant change (>60 ms) at the peak concentration after administration of 2000 mg but no signs of arrhythmias or severe morphologic changes (such as T wave bumps, notches, etc) were observed. Since the sensitivity to torsades de pointes also depends on factors including cardiovascular disease, alcoholic liver disease, obesity, hypertension, and/or electrolyte disturbances (Drew B J et al, *Circulation* 2010, 121:1047-1060; Isbister G K et al. *Br J Clin Pharmacol* 2013, 76:48-57), high concentrations (e.g. more than a total daily dose of 1000 mg) of KH176 preferably should not be given to patients with any of these risk factors. Moreover, until dose adjustments for patients with concomitant medication (also metabolized by CYP3A4) are determined, high concentrations (e.g. more than a total daily dose of 1000 mg) of KH176 should preferably not be given to these patients either since unpredictable pharmacokinetics will possibly lead to plasma concentrations of KH176 above the currently defined safety threshold.

Since the mechanism of KH176 is based on correction of an abnormal redox balance, as expected, we did not observed any pharmacodynamics changes in the healthy male volunteers.

Benchmarking human exposure to in vitro activity of KH176 and metabolites indicates that 100 mg b.i.d. dosing results in an efficacious exposure.

We conclude that administration of single doses up to and including 800 mg or multiple doses up to 400 mg b.i.d. for 7 days of KH176, a new small redox-modulating molecule developed to treat mitochondrial(-related) diseases and conditions, is safe and well tolerated. Although doses above the anticipated human efficacious dose could lead to prolongation of the QTc interval with T-wave abnormalities, the administration of the anticipated efficacious doses (100 mg b.i.d.) did not lead to changes in cardiac electrophysiology. More precisely, an exposure-response analysis demonstrated that there is a concentration range available without effects on repolarization, and the 100 mg BID dose with maximum concentrations ranging within 303-458 ng/ml is within that range. Furthermore, effects on repolarization seem to start at plasma concentrations roughly a factor 2 higher and upwards (500-1000 ng/ml, see FIG. 7).

Compared to Idebenone (approved for the treatment of Friedreich's ataxia), we show that KH176 has a favourable pharmacokinetic profile with higher exposures at 100 mg BID, while KH176 is also more active in the fibroblast assays. Compared to EPI-743 (100 mg tid is a pediatric study in Leigh's disease), KH176 100 mg BID has a slightly higher exposure (due to a slightly longer half live). Fibroblast assays (Redox assay) with KH176 and KH176m demonstrate an EC50 of 182 nM (around 60 ng/ml) for KH176 and 16 nM (around 5.8 ng/ml) for KH176m. Therefore at 100 mg BID of KH176, average concentrations of the parent KH176 are a factor 3-5 above EC50's and average concentrations of KH176m are a factor 10-20 above EC50's. Of note, protein binding of KH176 is limited, around 50-60% and has limited influence on the calculation, however, free concentrations are half of the total.

The invention claimed is:

1. A method of treating or suppressing symptoms associated with a mitochondrial disorder or with a disease or condition associated with mitochondrial dysfunction by administration of a total daily dose in the range of about 10 to 800 mg of a compound represented by general structure (VIIIa) or (VIIIb) or (IXa) or (IXb):

(VIIIa)

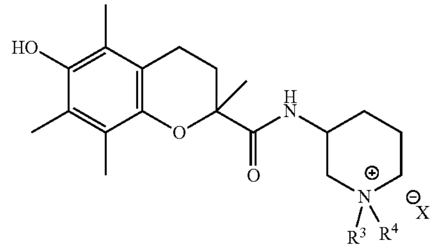

(VIIIb)

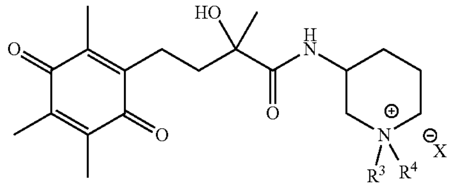

(IXa)

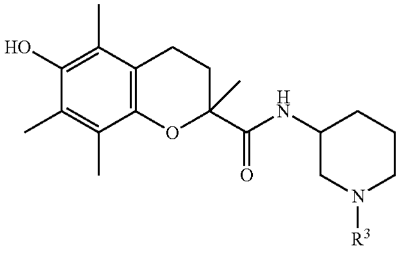

-continued (IXb)

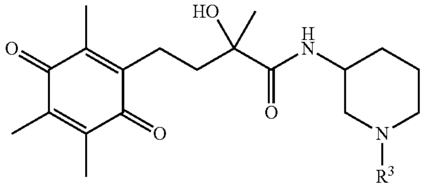

$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties; and $R^4$ is selected from hydrogen (H) or $C_1$-$C_6$ alkyl, wherein the alkyl moiety may be substituted with one or more halogen atoms or (halo)alkoxy moieties;

X is an anion;

wherein the mitochondrial disorder is a disorder selected from the group consisting of: Myoclonic epilepsy; Myoclonic Epilepsy with Ragged Red Fibers (MERRF); Leber's Hereditary Optic Neuropathy (LHON); neuropathy ataxia and retinitis pigmentosa (NARP); Mitochondrial Myopathy, Encephalopathy, Lactic acidosis, Stroke-like episodes (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); myopathy; mitochondrial myopathy; cardiomyopathy; and encephalomyopathy, SURF1 (COX deficient Leigh syndrome due to complex IV surfeit protein deficiency) and isolated or combined OXPHOS deficiencies with so far unsolved genetic defect including disturbed pyruvate oxidation and ATP plus PCr production rates; and wherein the disease or condition associated with mitochondrial dysfunction is a disease or condition selected from the group consisting of: Friedreich's Ataxia (FRDA); renal tubular acidosis; Parkinson's disease; Alzheimer's disease; amyotrophic lateral sclerosis (ALS); Huntington's disease; developmental pervasive disorders; hearing loss; deafness; diabetes; ageing; and adverse drug effects hampering mitochondrial function.

2. The method of claim 1, wherein a measurable biomarker is used to assess the efficacy of the therapy.

3. The method of claim 1, wherein the compound is administered orally.

4. The method of claim 1, wherein the compound is administered in a solid form or in a liquid form.

5. The method of claim 1, wherein the compound is administered at least twice daily.

6. The method of claim 5, wherein the interval between two administrations is at least about 1, 2, 3, 4, 5, 6, 7, 8, 9, 10, 11 or 12 hours.

7. The method of claim 1, wherein the subject to be treated is a primate.

8. The method of claim 1, wherein the subject to be treated has a clinically relevant normal ECG and/or a normal cardiac functioning.

9. The method of claim 1, wherein the subject to be treated does not have a concomitant medication that is known to inhibit CYP3A4 and/or PgP.

10. The method of claim 1, wherein the subject to be treated is a human of 17 years or younger.

11. The method of claim 1, wherein X is a pharmaceutically acceptable anion.

12. The method of claim 2, wherein the biomarker is selected from the group consisting of FGF21, GDF15, PRDX1 and oxidized glutathione/reduced glutathione ratio.

13. The method of claim 4, wherein the compound is admixed with an aqueous solution prior to administration.

14. The method of claim 13, wherein the aqueous solution is an isotonic aqueous solution.

15. The method of claim 5, wherein the compound is administered twice daily.

16. The method of claim 7, wherein the subject is human.

17. The method of claim 8, wherein the subject to be treated does not have an abnormal QTc of more than 500 ms and/or an abnormal T-wave morphology.

18. The method of claim 8, wherein the subject to be treated does not have a condition selected from the group consisting of cardiovascular disease, alcoholic liver disease, obesity, hypertension and electrolyte disturbances.

* * * * *